United States Patent
Sharma et al.

(10) Patent No.: US 12,108,983 B2
(45) Date of Patent: *Oct. 8, 2024

(54) DEVICE, SYSTEM AND METHOD TO ABLATE CARDIAC TISSUE

(71) Applicant: Biosense Webster (Israel) Ltd., Yokneam (IL)

(72) Inventors: Reecha Sharma, Irvine, CA (US); Robert B. Stagg, Irvine, CA (US); Zhong Wang, Irvine, CA (US); Betzi Zafra, Irvine, CA (US); Lee Ming Boo, Irvine, CA (US); Assaf Govari, Haifa (IL); Thomas V. Selkee, Irvine, CA (US); Christopher Thomas Beeckler, Brea, CA (US); Andres Claudio Altmann, Irvine, CA (US); Joseph Thomas Keyes, Sierra Madre, CA (US); Athanassios Papaioannou, Irvine, CA (US); Kristine B. Fuimaono, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 208 days.

This patent is subject to a terminal disclaimer.

(21) Appl. No.: 17/526,299

(22) Filed: Nov. 15, 2021

(65) Prior Publication Data

US 2022/0151693 A1 May 19, 2022

Related U.S. Application Data

(62) Division of application No. 16/864,704, filed on May 1, 2020, now Pat. No. 11,172,984.

(Continued)

(51) Int. Cl.
*A61B 18/14* (2006.01)
*A61B 18/00* (2006.01)

(52) U.S. Cl.
CPC ...... *A61B 18/1492* (2013.01); *A61B 2018/00351* (2013.01); *A61B 2018/00577* (2013.01);
(Continued)

(58) Field of Classification Search
CPC ... A61B 2018/00351; A61B 2018/00714; A61B 18/1492
See application file for complete search history.

(56) References Cited

U.S. PATENT DOCUMENTS

| 4,566,467 A | 1/1986 | DeHaan |
| 4,649,937 A | 3/1987 | DeHaan et al. |

(Continued)

FOREIGN PATENT DOCUMENTS

| CN | 1638700 A | 7/2005 |
| CN | 101484083 A | 7/2009 |

(Continued)

OTHER PUBLICATIONS

Calkins, H., et al. "2017 HRS/EHRA/ECAS/APHRS/SOLAECE expert consensus statement on catheter and surgical ablation of atrial fibrillation." Ep Europace 20, No. 1 (2018): e1-e160.
(Continued)

*Primary Examiner* — Linda C Dvorak
*Assistant Examiner* — Ryan T Clark
(74) *Attorney, Agent, or Firm* — Troutman Pepper Hamilton Sanders LLP

(57) ABSTRACT

A method that includes selectively positioning an ablation catheter system at a treatment site; and ablating tissue at the treatment site with the ablation catheter system using a power setting of approximately 90W applied to tissue for approximately four (4) second increments with a break period of approximately 4 seconds between applications.

19 Claims, 39 Drawing Sheets

Related U.S. Application Data

(60) Provisional application No. 62/892,464, filed on Aug. 27, 2019, provisional application No. 62/843,213, filed on May 3, 2019.

(52) U.S. Cl.
CPC ............... *A61B 2018/00678* (2013.01); *A61B 2018/00714* (2013.01); *A61B 2018/00755* (2013.01); *A61B 2218/002* (2013.01)

(56) References Cited

U.S. PATENT DOCUMENTS

| | | |
|---|---|---|
| 5,005,147 A | 4/1991 | Krishen et al. |
| 5,122,137 A | 6/1992 | Lennox |
| 5,180,896 A | 1/1993 | Gibby et al. |
| 5,286,944 A | 2/1994 | Li |
| 5,391,199 A | 2/1995 | Ben-Haim |
| 5,464,485 A | 11/1995 | Hall, Jr. |
| 5,499,631 A | 3/1996 | Weiland |
| 5,540,681 A | 7/1996 | Strul et al. |
| 5,542,916 A | 8/1996 | Hirsch et al. |
| 5,573,533 A | 11/1996 | Strul |
| 5,579,764 A | 12/1996 | Goldreyer |
| 5,626,140 A | 5/1997 | Feldman et al. |
| 5,688,267 A | 11/1997 | Panescu et al. |
| 5,702,386 A | 12/1997 | Stern et al. |
| 5,735,846 A | 4/1998 | Panescu et al. |
| 5,743,903 A | 4/1998 | Stern et al. |
| 5,755,715 A | 5/1998 | Stern et al. |
| 5,769,847 A | 6/1998 | Panescu et al. |
| 5,800,432 A | 9/1998 | Swanson |
| 5,833,688 A | 11/1998 | Sieben et al. |
| 5,835,693 A | 11/1998 | Lynch et al. |
| 5,893,884 A | 4/1999 | Tu |
| 5,906,614 A | 5/1999 | Stern et al. |
| 5,921,924 A | 7/1999 | Avitall |
| 5,931,836 A | 8/1999 | Hatta et al. |
| 5,935,124 A | 8/1999 | Klumb et al. |
| 5,956,464 A | 9/1999 | Madni et al. |
| 5,957,961 A | 9/1999 | Maguire et al. |
| 5,971,980 A | 10/1999 | Sherman |
| 6,022,346 A | 2/2000 | Panescu et al. |
| 6,030,379 A | 2/2000 | Panescu et al. |
| 6,036,687 A | 3/2000 | Laufer et al. |
| 6,045,550 A | 4/2000 | Simpson et al. |
| 6,049,737 A | 4/2000 | Simpson et al. |
| 6,053,912 A | 4/2000 | Panescu et al. |
| 6,056,745 A | 5/2000 | Panescu et al. |
| 6,092,033 A | 7/2000 | Uhlmann |
| 6,106,524 A | 8/2000 | Eggers et al. |
| 6,139,546 A | 10/2000 | Koenig et al. |
| 6,144,870 A | 11/2000 | Griffin, III |
| 6,162,184 A | 12/2000 | Swanson et al. |
| 6,203,541 B1 | 3/2001 | Keppel |
| 6,210,406 B1 | 4/2001 | Webster |
| 6,217,573 B1 | 4/2001 | Webster |
| 6,217,574 B1 | 4/2001 | Webster |
| 6,226,542 B1 | 5/2001 | Reisfeld |
| 6,231,569 B1 | 5/2001 | Bek et al. |
| 6,239,724 B1 | 5/2001 | Doron et al. |
| 6,293,943 B1 | 9/2001 | Panescu et al. |
| 6,301,496 B1 | 10/2001 | Reisfeld |
| 6,332,089 B1 | 12/2001 | Acker et al. |
| 6,356,790 B1 | 3/2002 | Maguire et al. |
| 6,409,722 B1 | 6/2002 | Hoey et al. |
| 6,436,096 B1 | 8/2002 | Hareyama |
| 6,484,118 B1 | 11/2002 | Govari |
| 6,558,378 B2 | 5/2003 | Sherman et al. |
| 6,575,969 B1 | 6/2003 | Rittman, III et al. |
| 6,582,425 B2 | 6/2003 | Simpson |
| 6,618,612 B1 | 9/2003 | Acker et al. |
| 6,652,513 B2 | 11/2003 | Panescu et al. |
| 6,690,417 B1 | 2/2004 | Yoshida et al. |
| 6,690,963 B2 | 2/2004 | Ben-Haim et al. |
| 6,799,064 B1 | 9/2004 | Hassett |
| 6,814,733 B2 | 11/2004 | Schwartz et al. |
| 6,829,568 B2 | 12/2004 | Julier et al. |
| 6,892,091 B1 | 5/2005 | Ben-Haim et al. |
| 6,898,848 B2 | 5/2005 | Ohkubo et al. |
| 6,898,849 B2 | 5/2005 | Trejo |
| 6,909,997 B2 | 6/2005 | Chen et al. |
| 6,952,616 B2 | 10/2005 | Wessman et al. |
| 6,997,924 B2 | 2/2006 | Schwartz et al. |
| 7,047,068 B2 | 5/2006 | Haissaguerre |
| 7,065,465 B2 | 6/2006 | Chen et al. |
| 7,077,840 B2 | 7/2006 | Altshuler et al. |
| 7,084,859 B1 | 8/2006 | Pryor |
| 7,104,987 B2 | 9/2006 | Biggs et al. |
| 7,156,816 B2 | 1/2007 | Schwartz et al. |
| 7,207,989 B2 | 4/2007 | Pike, Jr. et al. |
| 7,293,400 B2 | 11/2007 | Taware et al. |
| 7,300,438 B2 | 11/2007 | Falwell et al. |
| 7,306,594 B2 | 12/2007 | Collins et al. |
| 7,377,906 B2 | 5/2008 | Selkee |
| 7,520,877 B2 | 4/2009 | Lee, Jr. et al. |
| 7,536,218 B2 | 5/2009 | Govari et al. |
| 7,591,799 B2 | 9/2009 | Selkee |
| 7,594,913 B2 | 9/2009 | Ormsby et al. |
| 7,727,229 B2 | 6/2010 | He et al. |
| 7,850,685 B2 | 12/2010 | Kunis et al. |
| 8,021,327 B2 | 9/2011 | Selkee |
| 8,150,558 B2 | 4/2012 | Ito et al. |
| 8,157,796 B2 | 4/2012 | Collins et al. |
| 8,206,384 B2 | 6/2012 | Falwell et al. |
| 8,273,084 B2 | 9/2012 | Kunis et al. |
| 8,337,492 B2 | 12/2012 | Kunis et al. |
| 8,348,888 B2 | 1/2013 | Selkee |
| 8,357,152 B2 | 1/2013 | Govari et al. |
| 8,376,990 B2 | 2/2013 | Ponzi et al. |
| 8,388,549 B2 | 3/2013 | Paul et al. |
| 8,414,579 B2 | 4/2013 | Kim et al. |
| 8,437,832 B2 | 5/2013 | Govari et al. |
| 8,449,539 B2 | 5/2013 | Wang et al. |
| 8,456,182 B2 | 6/2013 | Bar-Tal et al. |
| 8,460,285 B2 | 6/2013 | Wang et al. |
| 8,475,448 B2 | 7/2013 | Sharareh et al. |
| 8,535,308 B2 | 9/2013 | Govari et al. |
| 8,554,299 B2 | 10/2013 | Sinderby et al. |
| 8,600,472 B2 | 12/2013 | Govari et al. |
| 8,636,731 B2 | 1/2014 | Falwell et al. |
| 8,641,705 B2 | 2/2014 | Leo et al. |
| 8,668,686 B2 | 3/2014 | Govari et al. |
| 8,706,193 B2 | 4/2014 | Govari et al. |
| 8,784,413 B2 | 7/2014 | Govari et al. |
| 8,818,485 B2 | 8/2014 | Govari et al. |
| 8,882,761 B2 | 11/2014 | Desai |
| 8,900,228 B2 | 12/2014 | Grunewald et al. |
| 8,900,229 B2 | 12/2014 | Govari et al. |
| 8,986,300 B2 | 3/2015 | Govari et al. |
| 9,005,192 B2 | 4/2015 | Govari et al. |
| 9,044,156 B2 | 6/2015 | Clark et al. |
| 9,144,460 B2 | 9/2015 | Clark et al. |
| 9,204,820 B2 | 12/2015 | Clark et al. |
| 9,204,841 B2 | 12/2015 | Clark et al. |
| 9,265,574 B2 | 2/2016 | Bar-Tal et al. |
| 9,286,338 B2 | 3/2016 | Aravkin et al. |
| 9,445,725 B2 | 9/2016 | Govari et al. |
| 9,694,124 B2 | 7/2017 | Sievers |
| 9,728,061 B2 | 8/2017 | Shen et al. |
| 9,737,353 B2 | 8/2017 | Govari et al. |
| 9,956,035 B2 | 5/2018 | Govari et al. |
| 9,980,652 B2 | 5/2018 | Govari et al. |
| 9,980,772 B2 | 5/2018 | Bar-Tal et al. |
| 9,999,285 B2 | 6/2018 | Feng |
| 10,098,684 B2 | 10/2018 | Govari et al. |
| 10,201,385 B2 | 2/2019 | Grunewald et al. |
| 10,213,856 B2 | 2/2019 | Govari et al. |
| 10,292,763 B2 | 5/2019 | Govari et al. |
| 10,307,206 B2 | 6/2019 | Govari et al. |
| 10,405,920 B2 | 9/2019 | Govari et al. |
| 10,441,354 B2 | 10/2019 | Govari et al. |
| 10,517,667 B2 | 12/2019 | Govari et al. |
| 2001/0007070 A1 | 7/2001 | Stewart et al. |

(56) References Cited

U.S. PATENT DOCUMENTS

| | | |
|---|---|---|
| 2002/0026127 A1 | 2/2002 | Balbierz et al. |
| 2002/0058933 A1 | 5/2002 | Christopherson et al. |
| 2002/0065455 A1 | 5/2002 | Ben-Haim et al. |
| 2002/0077627 A1 | 6/2002 | Johnson et al. |
| 2002/0087208 A1 | 7/2002 | Koblish et al. |
| 2002/0123749 A1 | 9/2002 | Jain |
| 2002/0128643 A1 | 9/2002 | Simpson et al. |
| 2002/0151884 A1 | 10/2002 | Hoey et al. |
| 2002/0165529 A1 | 11/2002 | Danek |
| 2003/0050557 A1 | 3/2003 | Susil et al. |
| 2003/0069573 A1 | 4/2003 | Kadhiresan et al. |
| 2003/0078736 A1 | 4/2003 | Weng et al. |
| 2003/0120150 A1 | 6/2003 | Govari |
| 2003/0130711 A1 | 7/2003 | Pearson et al. |
| 2003/0153905 A1 | 8/2003 | Edwards et al. |
| 2003/0158551 A1 | 8/2003 | Paton et al. |
| 2003/0184468 A1 | 10/2003 | Chen et al. |
| 2003/0199768 A1 | 10/2003 | Cespedes et al. |
| 2003/0216621 A1 | 11/2003 | Alpert et al. |
| 2003/0226098 A1 | 12/2003 | Weng |
| 2003/0229286 A1 | 12/2003 | Lenker |
| 2004/0019350 A1 | 1/2004 | O'Brien et al. |
| 2004/0068178 A1 | 4/2004 | Govari |
| 2004/0092806 A1 | 5/2004 | Sagon et al. |
| 2004/0193148 A1 | 9/2004 | Wham et al. |
| 2004/0193152 A1 | 9/2004 | Sutton et al. |
| 2004/0206365 A1 | 10/2004 | Knowlton |
| 2004/0243121 A1 | 12/2004 | Lee et al. |
| 2005/0251062 A1 | 11/2005 | Choi et al. |
| 2005/0267460 A1 | 12/2005 | Roop et al. |
| 2006/0074496 A1 | 4/2006 | Taware et al. |
| 2006/0217707 A1 | 9/2006 | Daniel et al. |
| 2006/0253030 A1 | 11/2006 | Altmann et al. |
| 2006/0253116 A1 | 11/2006 | Avitall et al. |
| 2006/0287649 A1 | 12/2006 | Ormsby et al. |
| 2007/0005306 A1 | 1/2007 | Foessel |
| 2007/0016007 A1 | 1/2007 | Govari et al. |
| 2007/0060832 A1 | 3/2007 | Levin |
| 2007/0063691 A1 | 3/2007 | Yakymyshyn et al. |
| 2007/0076917 A1 | 4/2007 | Chen et al. |
| 2007/0198007 A1 | 8/2007 | Govari et al. |
| 2007/0208333 A1 | 9/2007 | Uchida et al. |
| 2007/0293792 A1 | 12/2007 | Sliwa et al. |
| 2008/0039790 A1 | 2/2008 | Hasebe |
| 2008/0071263 A1 | 3/2008 | Blaha |
| 2008/0114351 A1 | 5/2008 | Irisawa et al. |
| 2008/0234564 A1 | 9/2008 | Beatty et al. |
| 2008/0281322 A1 | 11/2008 | Sherman et al. |
| 2008/0287944 A1 | 11/2008 | Pearson et al. |
| 2008/0300487 A1 | 12/2008 | Govari et al. |
| 2008/0300588 A1 | 12/2008 | Groth et al. |
| 2008/0319436 A1 | 12/2008 | Daniel et al. |
| 2009/0187183 A1 | 7/2009 | Epstein |
| 2009/0209950 A1 | 8/2009 | Starksen |
| 2009/0234351 A1 | 9/2009 | Desinger et al. |
| 2009/0248003 A1 | 10/2009 | Orszulak |
| 2009/0259221 A1 | 10/2009 | Tahara et al. |
| 2009/0299142 A1 | 12/2009 | Uchiyama et al. |
| 2009/0306650 A1 | 12/2009 | Govari et al. |
| 2010/0016848 A1 | 1/2010 | Desai |
| 2010/0057072 A1 | 3/2010 | Roman et al. |
| 2010/0168557 A1 | 7/2010 | Deno et al. |
| 2010/0168736 A1 | 7/2010 | Wang |
| 2010/0179534 A1 | 7/2010 | Podhajsky et al. |
| 2010/0262135 A1 | 10/2010 | Berube |
| 2010/0298826 A1 | 11/2010 | Leo et al. |
| 2010/0298895 A1 | 11/2010 | Ghaffari et al. |
| 2011/0009857 A1 | 1/2011 | Subramaniam et al. |
| 2011/0020779 A1 | 1/2011 | Hannaford et al. |
| 2011/0066147 A1 | 3/2011 | He et al. |
| 2011/0106074 A1 | 5/2011 | Kunis et al. |
| 2011/0130648 A1 | 6/2011 | Beeckler et al. |
| 2011/0130816 A1 | 6/2011 | Howard et al. |
| 2011/0137147 A1 | 6/2011 | Skliar et al. |
| 2011/0152856 A1 | 6/2011 | Govari et al. |
| 2011/0152857 A1 | 6/2011 | Ingle |
| 2011/0190759 A1* | 8/2011 | Qin .................. A61B 18/18 606/33 |
| 2011/0202055 A1 | 8/2011 | Selig |
| 2011/0224573 A1 | 9/2011 | Bar-Tal et al. |
| 2011/0301414 A1 | 12/2011 | Hotto et al. |
| 2012/0022510 A1 | 1/2012 | Welches et al. |
| 2012/0095362 A1 | 4/2012 | Fang et al. |
| 2012/0116386 A1 | 5/2012 | Govari et al. |
| 2012/0123400 A1 | 5/2012 | Francischelli et al. |
| 2012/0184863 A1 | 7/2012 | Harlev et al. |
| 2012/0226130 A1 | 9/2012 | De Graff et al. |
| 2012/0232388 A1 | 9/2012 | Curra et al. |
| 2012/0253167 A1 | 10/2012 | Bonyak et al. |
| 2012/0265195 A1 | 10/2012 | Gilbert |
| 2012/0278005 A1 | 11/2012 | Sumi |
| 2013/0046175 A1 | 2/2013 | Sumi |
| 2013/0060245 A1 | 3/2013 | Grunewald et al. |
| 2013/0079650 A1 | 3/2013 | Turgeman et al. |
| 2013/0116688 A1 | 5/2013 | Kunis et al. |
| 2013/0123775 A1 | 5/2013 | Grunewald et al. |
| 2013/0178910 A1 | 7/2013 | Azamian et al. |
| 2013/0237977 A1 | 9/2013 | McCarthy et al. |
| 2013/0282084 A1 | 10/2013 | Mathur et al. |
| 2014/0012251 A1 | 1/2014 | Himmelstein et al. |
| 2014/0047712 A1 | 2/2014 | Evans et al. |
| 2014/0052119 A1 | 2/2014 | Stewart et al. |
| 2014/0052120 A1 | 2/2014 | Benscoter et al. |
| 2014/0058375 A1 | 2/2014 | Koblish |
| 2014/0081262 A1 | 3/2014 | Koblish et al. |
| 2014/0171821 A1 | 6/2014 | Govari et al. |
| 2014/0275993 A1 | 9/2014 | Ballakur |
| 2014/0279682 A1 | 9/2014 | Feldman |
| 2014/0289802 A1 | 9/2014 | Lee et al. |
| 2015/0035658 A1 | 2/2015 | Provancher et al. |
| 2015/0088119 A1 | 3/2015 | Moss |
| 2015/0105765 A1 | 4/2015 | Panescu et al. |
| 2015/0112321 A1 | 4/2015 | Cadouri |
| 2015/0133914 A1 | 5/2015 | Koblish |
| 2015/0179129 A1 | 6/2015 | Byun |
| 2015/0272655 A1 | 10/2015 | Condie et al. |
| 2015/0295296 A1 | 10/2015 | Ikemoto et al. |
| 2015/0320478 A1 | 11/2015 | Cosman, Jr. et al. |
| 2015/0342671 A1 | 12/2015 | Govari et al. |
| 2016/0143696 A1 | 5/2016 | Govari et al. |
| 2016/0269851 A1 | 9/2016 | Baumert et al. |
| 2017/0049513 A1 | 2/2017 | Cosman, Jr. et al. |
| 2017/0181787 A1 | 6/2017 | Govari et al. |
| 2017/0209208 A1 | 7/2017 | Govari et al. |
| 2017/0209209 A1 | 7/2017 | Govari et al. |
| 2017/0209210 A1 | 7/2017 | Govari et al. |
| 2017/0209211 A1* | 7/2017 | Govari ............. A61B 18/1492 |
| 2018/0104000 A1 | 4/2018 | Beeckler et al. |
| 2018/0221088 A1 | 8/2018 | Govari et al. |
| 2018/0243030 A1 | 8/2018 | Bar-Tal et al. |
| 2018/0250063 A1 | 9/2018 | Schall et al. |
| 2019/0038349 A1* | 2/2019 | Koblish ............... A61B 5/6885 |
| 2019/0117298 A1 | 4/2019 | Beeckler |
| 2019/0167347 A1 | 6/2019 | Grunewald Highsmith et al. |
| 2019/0175247 A1 | 6/2019 | Govari et al. |
| 2019/0274056 A1 | 9/2019 | Raleigh et al. |

FOREIGN PATENT DOCUMENTS

| | | |
|---|---|---|
| CN | 101902978 A | 12/2010 |
| CN | 101947130 A | 1/2011 |
| CN | 102106753 A | 6/2011 |
| CN | 102188283 A | 9/2011 |
| CN | 103209654 A | 7/2013 |
| CN | 103327887 A | 9/2013 |
| CN | 103429183 A | 12/2013 |
| CN | 103584853 A | 2/2014 |
| CN | 103767787 A | 5/2014 |
| CN | 104125815 A | 10/2014 |
| CN | 104274239 A | 1/2015 |
| CN | 104545953 A | 4/2015 |
| CN | 105030326 A | 11/2015 |
| CN | 105120785 A | 12/2015 |
| EP | 0020288 A1 | 12/1980 |

(56) References Cited

FOREIGN PATENT DOCUMENTS

| | | |
|---|---|---|
| EP | 1500378 A1 | 1/2005 |
| EP | 2338428 A1 | 6/2011 |
| EP | 2364664 A1 | 9/2011 |
| EP | 2441408 A1 | 4/2012 |
| EP | 2526887 A1 | 11/2012 |
| EP | 2662116 A1 | 11/2013 |
| EP | 2942023 A2 | 11/2015 |
| EP | 2954865 A1 | 12/2015 |
| EP | 3216412 A1 | 9/2017 |
| JP | H04127375 A | 4/1992 |
| JP | H0779995 A | 3/1995 |
| JP | H08503381 A | 4/1996 |
| JP | H09501858 A | 2/1997 |
| JP | H0994252 A | 4/1997 |
| JP | H10225462 A | 8/1998 |
| JP | H11155869 A | 6/1999 |
| JP | 2000157556 A | 6/2000 |
| JP | 2000201949 A | 7/2000 |
| JP | 2000223067 A | 8/2000 |
| JP | 2000235995 A | 8/2000 |
| JP | 2002537939 A | 11/2002 |
| JP | 2004520865 A | 7/2004 |
| JP | 2005040616 A | 2/2005 |
| JP | 2005517498 A | 6/2005 |
| JP | 2008508043 A | 3/2008 |
| JP | 2008080152 A | 4/2008 |
| JP | 2009112794 A | 5/2009 |
| JP | 2010259810 A | 11/2010 |
| JP | 2010276428 A | 12/2010 |
| JP | 2011131061 A | 7/2011 |
| JP | 2012506744 A | 3/2012 |
| JP | 2012531967 A | 12/2012 |
| JP | 2013523318 A | 6/2013 |
| JP | 2013233436 A | 11/2013 |
| JP | 2014518519 A | 7/2014 |
| JP | 2014213431 A | 11/2014 |
| JP | 2014533130 A | 12/2014 |
| JP | 2015096193 A | 5/2015 |
| JP | 2015100709 A | 6/2015 |
| JP | 2016077894 A | 5/2016 |
| JP | 2017131659 A | 8/2017 |
| JP | 6797702 B2 | 12/2020 |
| WO | 9600036 A1 | 1/1996 |
| WO | 199605768 A1 | 2/1996 |
| WO | 9730647 A1 | 8/1997 |
| WO | 9917672 A1 | 4/1999 |
| WO | 0232335 A1 | 4/2002 |
| WO | 03070284 A2 | 8/2003 |
| WO | 2006014966 A2 | 2/2006 |
| WO | 2008011575 A1 | 1/2008 |
| WO | 2008099851 A1 | 8/2008 |
| WO | 2008112005 A1 | 9/2008 |
| WO | 2011002349 A1 | 1/2011 |
| WO | 2011052349 A1 | 5/2011 |
| WO | 2011113070 A1 | 9/2011 |
| WO | 2012059131 A1 | 5/2012 |
| WO | 2012071388 A2 | 5/2012 |
| WO | 2012071388 A3 | 1/2013 |
| WO | 2013052590 A1 | 4/2013 |
| WO | 2013052919 A2 | 4/2013 |
| WO | 2020225696 A1 | 11/2020 |

OTHER PUBLICATIONS

Iwasawa, J., et al. "Temperature-controlled radiofrequency ablation for pulmonary vein isolation in patients with atrial fibrillation." Journal of the American College of Cardiology 70, No. 5 (2017): 542-553.

International Search Report issued in International Application No. PCT/IB2020/054178 and dated Jul. 30, 2020.

Warman, E. N., Grammatico, A., & Padeletti, L. (2004). Sample size estimates for atrial fibrillation endpoints. Hearty rhythm. 1(1 Suppl). B58-B63. https://doi.org/10.1016/j.hrthm.2004.04.009 (Year: 2004).

CNIPA First Office Action issued Jun. 30, 2020, in corresponding CN Application No. 201610908229.4, English translation, 9 pages.

CNIPA Search Report dated Jun. 22, 2020, for corresponding CN Application No. 201610908229.4, English translation, 2 pages.

Co-Pending U.S. Appl. No. 12/941,165, filed Nov. 8, 2010, 39 pages.

Co-Pending U.S. Appl. No. 13/716,578, filed Dec. 17, 2012, 26 pages.

Decision on Rejection for Chinese Application No. 201510249718.9, mailed on Jul. 3, 2020, 15 pages.

Durrant-White H., "Multi-Sensor Data Fusion," The University of Sydney, Jan. 22, 2001, 154 pages.

EPO Examination Report dated Mar. 26, 2018, issued in corresponding EP Patent Application No. 16194402.0, 5 pages.

European Communication for European Application No. 15167813.3, mailed May 10, 2017, 8 Pages.

Examination Decision of the Reexamination Request for Chinese Application No. 201510249718.9, mailed on Apr. 28, 2022, 15 pages.

Examination Report for Australian Application No. 2015202245, mailed on Feb. 5, 2019, 3 pages.

Extended European Search Report for European Application No. 11193722.3, mailed Jul. 13, 2012, 6 Pages.

Extended European Search Report for European Application No. 14189558.1, mailed Mar. 13, 2015, 4 Pages.

Extended European Search Report for European Application No. 15167813.3, mailed Oct. 9, 2015, 9 Pages.

Extended European Search Report for European Application No. 16152827.8, mailed May 4, 2016, 6 Pages.

Extended European Search Report for European Application No. 16194402.0, mailed Mar. 27, 2017, 5 Pages.

Extended European Search Report for European Application No. 17152784.9, mailed Jul. 11, 2017, 9 Pages.

Extended European Search Report for European Application No. 17152786.4, mailed Aug. 17, 2017, 8 Pages.

Extended European Search Report for European Application No. 17152826.8, mailed Jul. 11, 2017, 7 Pages.

Extended European Search Report for European Application No. 17152848.2, mailed Jul. 11, 2017, 7 Pages.

Extended European Search Report for European Application No. 21172063.6, mailed Sep. 29, 2021, 10 Pages.

International Preliminary Report on Patentability for International Application No. PCT/IB2020/054178, mailed Nov. 18, 2021, 8 Pages.

Notice of Reexamination for Chinese Application No. 201510249718.9, mailed on Nov. 30, 2021, 16 pages.

Notification of Reasons for Refusal in Corresponding Japanese Application No. 2011-274253, dated Nov. 10, 2015, 8 Pages.

Office Action for Chinese Application No. 201510249718.9, dated Aug. 24, 2018.

Notification of Reasons for Refusal for Japanese Application No. 2015-099775, mailed on Feb. 5, 2019, 4 pages.

Second Office Action for Chinese Application No. 201510249718.9, mailed on Jun. 3, 2020, 11 pages.

"Tactisys Quartz System by Endosense," Geneva, Switzerland.

Tempany et al., "Focused Ultrasound Ablation Offer Prostate Cancer Option, Diagnostic Imaging," Jan. 1, 2009, Retrieved from URL: www.diagnosticimaging.com, 6 pages.

Third Office Action for Chinese Application No. 201510249718.9, mailed on Dec. 27, 2020, 11 pages.

Topp S.A., M.D. et al., "Saline-Linked Surface Radiofrequency Ablation Factors Affecting Steam Popping and Depth of Injury in the Pig Liver," Annals of Surgery, Apr. 2004, vol. 239, No. 4, pp. 518-527.

JPO Notification of Reasons for Refusal mailed Sep. 29, 2020, for corresponding JP Patent Applications No. 2016-204153.

English translation of Search Report dated Nov. 24, 2023, from corresponding Japanese Application No. 2021-565012.

* cited by examiner

Darker color indicating temperature rise

| Investigational Equipment | |
|---|---|
| catheter 28 | Delivers RF energy to the target tissue. |
| TX eco EXT Connection Cable (D-1357-03-SI) | Provides a means to interface catheter 28 with the Dongle |
| TX eco Cable (Dongle) (EM-5050-055F) | Provides a means to interface catheter 28 to the Multi-Channel RF Generator |
| nMARQ Multi-Channel RF Generator v3.0.1 (D-1341-07-I) | Transmits RF energy to the Ablation Catheter |
| CARTO 3 v6.0.60 catheter 28 Software Module | Provides a visual interface for the features of catheter 28 |
| Non-Investigational Equipment | |
| 8.5 F compatible sheath | Facilitate deployment of catheter into the atria. |
| Lasso® or PentaRay® (optional) | Pre-ablation recording and mapping of the atria of the heart with the CARTO® system. |
| CoolFlow® Irrigation Pump and Tubing Set | Delivers heparinized saline to the catheter for cooling during the RF energy application |
| Esophageal temperature monitoring device | Esophageal temperature monitoring |
| EP lab recording equipment | Records multiple intracardiac electrograms and signals from the RF generator (power, temperature, impedance) and performs electrical stimulation. |
| Adhesive electrical dispersive pads / indifferent electrode | Component of the RF current return path (Valley Lab recommended) |
| Interface Cables | Connection of choice |
| CARTO® System Junction Box | Provide the interface to the catheter, generator, and the CARTO® System. |
| Carto® 3 v 6.0 System | For mapping and visualization information. Version 6.0.60 or higher |

Fig. 12

| | Blanking period (≤ 90 days post procedure) | Post blanking period (> 90 days post procedure) |
|---|---|---|
| Class I and/or Class III AAD | Can be initiated, continued from prior to study enrollment, or increased in dose as long as the AAD is stopped on or before day 90 post procedure and subject will not be classified as a primary effectiveness failure. | If initiated for the treatment of AF; subject will be classified as a primary effectiveness failure. If initiated for the treatment of AF during the blanking period and continued past Day 90; Subject will be classified as a primary effectiveness failure Can be initiated, continued from blanking period, or increased if drug is NOT for the treatment of atrial arrhythmia (e.g. hypertension) other than CTI dependent AFL and subject will not be classified as a primary effectiveness failure. |
| Class II and/or Class IV AAD | Can be initiated, continued from prior to study enrollment, or increased in dose and subject will not be classified as a primary effectiveness failure. | Can be initiated, continued from prior to study enrollment, or increased in dose and subject will not be classified as a primary effectiveness failure. |

Fig. 13

| Power | Target Temp* | | Cut-off Temp | | Nominal Irrigation Flow rate |
|---|---|---|---|---|---|
| | Range | maximum allowed | Range | Maximum allowed | |
| 25-35 W | 40-50°C | 50°C | 50-55°C | 55°C | 4mL** |
| 36-50W*** | 40-50°C | 50°C | 50-55°C | 55°C | 15mL** |
| 90W† | 40-60°C | 60°C | 60-70°C | 70°C | 8mL** |

*Temperatures displayed on the RF generator do not represent tissue temperature or electrode tissue interface temperature.

** A minimum flow rate of 2mL during mapping is recommended.

*** RF applications at 36-50W should not exceed 60 sec.

† The study recommends using this power setting for PVI as a primary ablation Strategy. RF applications at this power setting are limited to 4 sec. It is recommended to use lower target temperature setting for the posterior wall RF applications.

Fig. 14

| | Pre-Proced. | | | Phone Call | Follow-Up Visits | | | | |
|---|---|---|---|---|---|---|---|---|---|
| | Screening Baseline | Study Abl Day 0 | D/C | 7 D D7-10 | 1 M D23-37 | 3 M D76-104 | 6M D150-210 | 12M D335-395 | UNS |
| Visit no. | 1 | 2 | 3 | 4 | 5 | 6 | 7 | 8 | 9 | 10 |
| Informed consent | X | | | | | | | | |
| Inc & Excl Criteria | X | | | | | | | | |
| Demographics | X | | | | | | | | |
| Vital Signs | X | | | | | | | | |
| Physical Exam | | X | | X | | X | X | X | X | X |
| NIHSS | | X | | X | | | | | | |
| Med History | X | | | | X | X | X | X | X | X |
| Arrhythmias History | X | | | | | | | | | |
| ECG | | X | | X | | X | X | X | X | X |
| Adverse Events | | X | X | X | X | X | X | X | X | X |
| CHA2DS2-Vasc Score | X | | | | | | | | | |
| NYHA Scale | | X | | | | | | | | |
| QOL Assessment | | X | | | | | X | X | X | |
| Preg Test | | X | | | | | | | | |
| LA thrombus Imaging | | | X | | | | | | | |
| TTE | | X | | X | | | | | | |
| Concomitant Medications | | X | X | X | X | X | X | X | X | X |
| mRS | | | | X | X | X | X | X | X |
| PV CT/MRA Subset | X | | | | | | X | | | |
| PV Stenosis CT/MRA | | | | | X | X | X | X | X | X |
| Ablation Assessments | | | X | | | | | | | |
| Repeat Ablation | | | | | | X | X | X | X | X |
| Device Deficiency | | | X | | | | | | | |
| Health Economic Data Collection | | | | X | X | X | X | X | X | X |
| AF/AT/AFL recurrence | | | | X | X | X | X | X | X | X |
| TTM | | | | | | X | X | X | X |
| 24-hour Holter | | | | | | | | | X | |
| Subject Completion/discontinuation form | | | | | | | | | X | |

Fig. 15

| PRIMARY ADVERSE EVENT | DESCRIPTION / CRITERIA |
|---|---|
| Death | Patient death directly related to the device or procedure and occurs at any time during or after the procedure. |
| Atrio-Esophageal Fistula | Is defined as a connection between the atrium and the lumen of the esophagus. Evidence supporting this diagnosis includes documentation of esophagus erosion combined with evidence of a fistulous connection to the atrium such as air emboli, an embolic event, or direct observation at the time of surgical repair. A CT or MRI scan is the most common method of documentation of an atrio-esophageal fistula. |
| Cardiac Tamponade/Perforation | The development of a significant pericardial effusion during or within 30 days of undergoing an AF ablation procedure. A significant pericardial effusion is one which results in hemodynamic compromise, requires elective or urgent pericardiocentesis, or results in a 1 cm or more pericardial effusion as documented by echocardiography. Cardiac tamponade should also be classified as "early" or "late" depending on whether it is diagnosed during or following initial discharge from the hospital. |
| Myocardial Infarction | The presence of any one of the following criteria:<br>·Detection of ECG changes indicative of new ischemia (new ST-T changes or new LBBB) which persists for more than 1 h<br>·Development of a new pathological Q waves on an ECG, and<br>·Imaging evidence of new loss of viable myocardium or new regional wall motion abnormality |

Fig. 16

| PRIMARY ADVERSE EVENT | DESCRIPTION / CRITERIA |
|---|---|
| Stroke/ Cerebrovascular Accident | Rapid onset of a focal or global neurological deficit with at least one of the following: change in level of consciousness, hemiplegia, hemiparesis, numbness or sensory loss affecting one side of the body, dysphasia or aphasia, hemianopia, amaurosis fugax, or other neurological signs or symptoms consistent with stroke. |
| | Duration of a focal or global neurological deficit ≥24 h; or <24 h, if therapeutic intervention(s) were performed (e.g. thrombolytic therapy or intracranial angioplasty); OR available neuroimaging documents a new hemorrhage or infarct; or the neurological deficit results in death. |
| | No other readily identifiable non-stroke cause for the clinical presentation (e.g., brain tumor, trauma, infection, hypoglycemia, peripheral lesion, pharmacological influences)† |
| | Confirmation of the diagnosis by at least one of the following: |
| | ·Neurology or neurosurgical specialist |
| | ·Neuroimaging procedure (MR or CT scan or cerebral angiography) |
| | ·Lumbar puncture (i.e., spinal fluid analysis diagnostic of intracranial hemorrhage) |
| | Stroke: (diagnosis as above, preferably with positive neuroimaging study) |
| | ·Minor—Modified Rankin score <2 at 30 and 90 days†† |
| | ·Major—Modified Rankin score ≥2 at 30 and 90 days |
| Thromboembolism | Formation of a clot (thrombus) inside a blood vessel causing obstruction to blood flow. The thrombus can migrate (embolus) and obstruct distal vascular sites. Diagnostic tests to help detect thromboembolisms may include but are not limited to angiography (pulmonary or distal), ventilation-perfusion (V/Q) scans, venography, Doppler ultrasonography, spiral CT, and echocardiography. |

Fig. 17

| PRIMARY ADVERSE EVENT | DESCRIPTION / CRITERIA |
|---|---|
| Transient Ischemic Attack | New focal neurological deficit with rapid symptom resolution (usually 1 to 2 h), always within 24h. Neuroimaging without tissue injury. |
| Phrenic Nerve Injury / Diaphragmatic Paralysis | Absent phrenic nerve function as assessed by a sniff test. A phrenic nerve paralysis is considered to be permanent when it is documented to be present 12 months or longer following ablation. |
| Heart Block | Impairment of AV conduction requiring intervention (e.g. temporary or permanent pacemaker) due to iatrogenic cause (e.g. inappropriate RF application, traumatic maneuvering of catheter or other intracardiac devices). |
| Pulmonary Vein Stenosis | A reduction of the diameter of a PV or PV branch. PV stenosis can be categorized as mild <50%, moderate 50-70%, and severe 70% reduction in the diameter of the PV or PV branch. PV stenosis (> 70% PV narrowing) regardless of the presence or absence of symptoms and PV stenosis with >= 50% PV narrowing when accompanied with relevant symptoms that cannot be explained by other etiologies will be considered a primary adverse event. |
| Pulmonary Edema (Respiratory Insufficiency) | Respiratory insufficiency resulting in pulmonary complications necessitating intubation or other significant intervention (including diuretics administered specifically for treating pulmonary edema or ICU hospitalization requiring oxygen administration but not intubation) Exclusion criteria include:<br>·Pneumonia – infiltrate, fever and leukocytosis<br>·Acute Respiratory Distress Syndrome |

Fig. 18

| PRIMARY ADVERSE EVENT | DESCRIPTION / CRITERIA |
|---|---|
| Vagal Nerve Injury | Injury to the vagal nerve that results in esophageal dysmotility or gastroparesis. Vagal nerve injury is considered to be a major complication if it prolongs hospitalization, requires hospitalization, or results in ongoing symptoms for more than 30 days following an ablation procedure. |
| Pericarditis | Should be considered a major complication following ablation if it results in effusion which leads to hemodynamic compromise or requires pericardiocentesis, prolongs hospitalization by more than 48 h, requires hospitalization, or persists for more than 30 days following the ablation procedure. |
| Major Vascular Access Complication / Bleeding | Major Bleeding: A major complication of AF ablation if it requires and/or treated with transfusion or results in a 20% or greater fall in HCT. Major Vascular Access Complication: Defined as hematoma, an AV fistula, or a pseudoaneurysm which requires intervention such as surgical repair or transfusion, prolongs the hospital stay, or requires hospital admission. |

Fig. 19

| | |
|---|---|
| Mild | Events that result in minimal transient impairment of a body function or damage to a body structure, and/or dos not require intervention other than monitoring. |
| Moderate | Events that result in moderate transient impairment of a body function or damage to a body structure, or that require intervention, such as the administration of medication, to prevent permanent impairment of a body function or damage to a body structure. |
| Severe | Events that are life threatening and/or result in permanent impairment of body functions or damage to body structures, or that require significant intervention, such as major surgery, to prevent permanent impairment of a body function or damage to a body structure. |

Fig. 20

| Recovered/ Resolved without Sequelae | Subject fully recovered with no observable residual effects. |
|---|---|
| Recovering/ Resolving | Subject's condition is improving but residual effects remain. |
| Recovered/ Resolved with Sequelae | Subject recovered with observable residual effects. |
| Not recovered/ resolved | AE is ongoing without improvement in overall condition |
| Fatal | Subject died as a result of the adverse event, whether or not the AE is related to the device or procedure. Note; deaths from any cause occurring on this study are to follow expedited reporting. |
| Unknown | AE outcome is unknown (e.g., subject lost to follow-up) |

Fig. 21

| Characteristic | Enrolled (n = 54) |
|---|---|
| Age, mean ± SD, years | 62.0 ± 12.01 |
| Male, n (%) | 36 (66.7) |
| $CHA_2DS_2$-VASc, mean ± SD | 2.0 ± 1.47 |
| AF duration, median (IQR), months | 28.5 (9.5–80.5) |
| Medical history, n (%) | |
|     Atrial flutter | 6 (11.1) |
|     Hypertension | 34 (63.0) |
|     Diabetes | 5 (9.3) |
|     Coronary disease | 4 (7.4) |
|     Prior thromboembolic events | 4 (7.4) |
|     Congestive heart failure | 10 (18.5) |
|         NYHA Class I | 3 (30.0) |
|         NYHA Class II | 7 (70.0) |
| Failed antiarrhythmic drug class, n (%) | 50 (92.6) |
|     Number of failed medications, mean ± SD | 1.7 ± 0.8 |
| Left ventricular ejection fraction, mean ± SD, % | 60.8 ± 5.0 |
| Left atrial dimension, mean ± SD, mm | 39.3 ± 5.16 |

Fig. 22

|  | Effectiveness population (n = 52) |
|---|---|
| Left PVI lesion set | 7 /14 (50.0%) |
| Superior | 1 /14 (7.1%) |
| Anterior | 3 /14 (21.4%) |
| Posterior | 4 /14 (28.6%) |
| Inferior | 1 /14 (7.1%) |
| Ridge | 1 /14 (7.1%) |
| Right PVI lesion set | 8 /14 (57.1%) |
| Anterior | 3 /14 (21.4%) |
| Posterior | 4 /14 (28.6%) |
| Inferior | 2 /14 (14.3%) |
| Ridge | 1 /14 (7.1%) |

Fig. 23

| Description | PAEs, n (%) | Relationship with catheter 28 or procedure |
|---|---|---|
| Total PAEs | 2 (3.8) | |
| Death | 0 | — |
| Atrioesophageal fistula* | 0 | — |
| Cardiac tamponade/perforation | 0 | — |
| Myocardial infarction | 0 | — |
| Stroke | 0 | — |
| Cerebrovascular accident | 0 | — |
| Thromboembolism | 1 (1.9) | Possibly related to catheter 28 Probably related to procedure |
| Transient ischemic attack | 0 | — |
| Phrenic nerve paralysis | 0 | — |
| PV stenosis* | 0 | — |
| Major vascular access complication or bleeding | 1 (1.9) | Not related to device Possibly related to procedure |

*Device- or procedure-related death, PV stenosis, and atrio-esophageal fistula that occur greater than 1 week (7 days) post-procedure are considered and analyzed as primary adverse events.

Fig. 24

|  | Fluid Delivered via catheter (mL) | % improvement by Catheter 28 | Total Procedure Time | % improvement by Catheter 28 | Total Ablation Time | % improvement by Catheter 28 |
|---|---|---|---|---|---|---|
| Thermocool | 1624.9 | 76.5% | 210.1 | 49.9% | 110.3 | 58.3% |
| Smart AF | 1879.6 | 79.7% | 222.7 | 52.8% | 121.5 | 62.1% |
| Smart SF | 898.4 | 57.4% | 181.1 | 41.9% | 104.3 | 55.9% |
| Catheter 28 | 382.4 | N/A | 105.2 | N/A | 46 | N/A |

Fig. 27A

|  | Total Fluoroscopy Time | % improvement by Catheter 28 | Total RF Application Duration | % improvement by Catheter 28 |
|---|---|---|---|---|
| Thermocool | 49.5 | 86.7% | NR | N/A |
| Smart AF | 41.5 | 84.1% | 60.6 | 86.6% |
| Smart SF | 18.6 | 64.5% | 49.5 | 83.6% |
| Catheter 28 | 6.6 | N/A | 8.1 | N/A |

Fig. 27B

| Duration | 4 sec | | | 2 sec |
|---|---|---|---|---|
| Target Temp (°C) | 50 | 55 | 60 | 60 |
| Total # of TGA ablations | 38 | 180 | 5004 | 47 |
| Mean Power (W) | 83.7 ± 3.7 | 84.4 ± 5.1 | 84.9 ± 1.5 | 82.4 ± 1.7* |
| Energy (Joules) | 334 ± 15 | 336 ± 21 | 339 ± 10 | 199 ± 12 |
| Power Titration (%) | 7.0 ± 4.1 | 6.3 ± 5.7 | 5.7 ± 2.8 | |
| Average Force (g) | 7.5 ± 5.6 | 9.1 ± 7.3 | 17.7 ± 11.7 | 13.6 ± 7.9 |
| Avg. Initial Imp (Ω) | 104.2 ± 4.3 | 107.2 ± 12.6 | 112.4 ± 11.5 | 114.6 ± 9.8 |
| Avg. Δ imp. (Ω) | 11.1 ± 3.5 | 11.0 ± 3.0 | 9.5 ± 3.4 | 8.4 ± 3.0 |
| Avg. Initial ET (°C) | 31.8 ± 0.7 | 31.4 ± 0.8 | 32.2 ± 1.3 | 31.4 ± 1.4 |
| Avg. Max ET (°C) | 46.2 ± 4.5 | 47.2 ± 5.3 | 47.8 ± 5.1 | 42.7 ± 4.2 |

\* Lower mean power was caused by the percentage of power ramp-up duration increased with shorter RF duration.

Fig. 28

| | Grouped by Unilateral PVs (level-1) | | Grouped by Specific Reconnection locations (level-2) | | Grouped by Specific Reconnection locations (Level 2 exclude ablations with large gap) | |
|---|---|---|---|---|---|---|
| | First Pass | Acute Reconnection | No-reconnection | Acute Reconnection | No-reconnection | Acute Reconnection |
| Total # of TGA ablations | 4653 | 442 | 4965 | 130 | 5024 | 71 |
| Mean Power (W) | 84.8 ± 2.6 | 84.9 ± 1.9 | 84.8 ± 2.6 | 84.8 ± 1.8 | 84.8 ± 2.6 | 85.1 ± 1.1 |
| Power Titration (%) | 5.8 ± 2.9 | 5.7 ± 2.1 | 5.8 ± 2.9 | 5.7 ± 1.9 | 5.8 ± 2.9 | 5.4 ± 1.2 |
| Energy (Joules) | 335 ± 24 | 334 ± 27 | 335 ± 24 | 329 ± 37 | 335 ± 24 | 323 ± 49 |
| Avg. Force (g) | 17.0 ± 11.2 | 21.4 ± 13.4 | 17.3 ± 11.5 | 19.7 ± 11.5 | 17.3 ± 11.5 | 20.2 ± 10.5 |
| Avg. Initial Imp (Ω) | 112.3 ± 11.6 | 110.8 ± 10.3 | 112.2 ± 11.6 | 111.7 ± 9.7 | 112.2 ± 11.6 | 109.1 ± 4.5 |
| Avg. Δ imp. (Ω) | 9.4 ± 3.4 | 9.2 ± 3.3 | 9.4 ± 3.4 | 9.1 ± 3.1 | 9.4 ± 3.4 | 8.7 ± 2.9 |
| Avg. Initial ET (°C) | 32.2 ± 1.3 | 31.6 ± 1.0 | 32.2 ± 1.3 | 31.5 ± 0.9 | 32.2 ± 1.3 | 31.7 ± 0.9 |
| Avg. Max ET (°C) | 47.7 ± 5.1 | 47.8 ± 4.9 | 47.8 ± 5.1 | 46.5 ± 4.5 | 47.8 ± 5.1 | 46.6 ± 4.3 |

```
inserting an ablation catheter system according to any
preceding claim to a treatment site comprising cardiac
tissue, the system comprising at least one electrode and at
least one sensor into the body in proximity
3310
```

```
ablating the cardiac tissue with the ablation catheter system
3320
```

```
achieving complete pulmonary vein isolation, by the
ablation catheter system, for all patients of a predetermined
patient population suffering from PAF
3330
```

```
┌─────────────────────────────────────────────────────┐
│ inserting an ablation catheter system according to any │
│ preceding claim into a body of a living subject; urging the │
│ ablation catheter system into contact with a cardiac tissue in │
│                      the body                       │
│                       3410                          │
└─────────────────────────────────────────────────────┘
                           ↓
┌─────────────────────────────────────────────────────┐
│  generating ablative energy at a power output level at a │
│                   level of current                  │
│                       3420                          │
└─────────────────────────────────────────────────────┘
                           ↓
┌─────────────────────────────────────────────────────┐
│  transmitting the generated energy into the tissue via the │
│                 ablation catheter system            │
│                       3430                          │
└─────────────────────────────────────────────────────┘
                           ↓
┌─────────────────────────────────────────────────────┐
│  ablating the cardiac tissue with the ablation catheter system │
│                       3440                          │
└─────────────────────────────────────────────────────┘
                           ↓
┌─────────────────────────────────────────────────────┐
│    clinically improving, by the ablation catheter system, │
│ safety and effectiveness resulting in approximately at least │
│   80% less RF ablation time compared to ablation time of a │
│    previous clinically approved catheter system for PAF. │
│                       3450                          │
└─────────────────────────────────────────────────────┘
```

Fig. 34

3600 inserting an ablation catheter system according to any preceding claim to a treatment site comprising cardiac tissue, the system comprising at least one electrode and at least one sensor into the body in proximity
3610 ablating the cardiac tissue with the ablation catheter system
3620 achieving clinically improved safety and effectiveness for PAF with substantially shorter total procedure, ablation, fluoroscopy, and radiofrequency application times
3630

Fig. 36

3900 delivering an ablation catheter system to a treatment site comprising cardiac tissue, the system comprising at least one electrode and at least one sensor in proximity with the other
3910

↓ ablating cardiac tissue with the ablation catheter system at a predetermined irrigation fluid rate and power setting comprising approximately 90W
3920

↓ achieving approximately zero incidence of steam pop occurrence in both left and right atrial ablations and complete pulmonary vein isolation, by the ablation catheter system, for all patients of a predetermined patient population suffering from PAF
3930

Fig. 39

DEVICE, SYSTEM AND METHOD TO ABLATE CARDIAC TISSUE

CROSS-REFERENCE TO RELATED APPLICATIONS

This application is a divisional application of U.S. patent application Ser. No. 16/864,704 filed May 1, 2020, which claims priority of U.S. Provisional Patent Application No. 62/843,213 filed May 3, 2019 and of U.S. Provisional Patent Application No. 62/892,464 filed Aug. 27, 2019. The contents of which are incorporated herein by reference in their entirety as if set forth verbatim.

FIELD

This disclosure relates generally to methods and devices for invasive medical treatment, and specifically to catheters, in particular, irrigated ablation catheters.

BACKGROUND

Ablation of myocardial tissue is well known as a treatment for cardiac arrhythmias. In radiofrequency (RF) ablation, for example, a catheter is inserted into the heart and brought into contact with tissue at a target location. RF energy is then applied through electrodes on the catheter in order to create a lesion for the purpose of breaking arrhythmogenic current paths in the tissue.

Irrigated catheters are now commonly used in ablation procedures. Irrigation provides many benefits including cooling of the electrode and tissue which prevents overheating of tissue that can otherwise cause the formation of char and coagulum and even steam pops. However, because tissue temperature is assessed during an ablation procedure to avoid such adverse occurrences, it is important that the temperature sensed accurately reflects the real temperature of the tissue and not merely the surface temperature of the tissue which can be biased by the cooling irrigation fluid from the catheter. Moreover, deeper tissue contact in general provides more accurate thermal and electrical readings, including improved impedance measurements for purposes including a determination of lesion size.

Accordingly, there is a desire for an irrigated ablation catheter with a distal end that can better probe tissue without significantly damaging or breaching the tissue, for more accurate measurements, including temperature sensing and impedance measurements.

Further, the pathophysiology of persistent atrial fibrillation (PAF), even for initial procedures, can be complex and often involves multiple triggers outside of the pulmonary vein areas, which makes their identification and treatment difficult. Multiple studies have demonstrated that success rates of pulmonary vein isolation (PVI) are lower in patients with persistent PAF. Atrial fibrillation (AF) is the most common sustained arrhythmia in humans. It affects anywhere from 0.4% to 1% of the general population, and increases in prevalence with age, from <1% in young adults to 8% in patients over 80 years of age. Radiofrequency (RF) catheter ablation has provided excellent results for treating many types of supraventricular arrhythmias. Its utility in treating paroxysmal AF has already been established; studies have shown high rates of elimination of the arrhythmia. In a non-randomized clinical trial evaluating the impact of contact force on successful outcomes, RF ablation with the THERMOCOOL SMARTTOUCH® SF catheter was associated with elimination of symptomatic atrial arrhythmias in 72.5% of patients at 1 year.

The 2017 HRS/EHRA/ECAS/APHRS/SOLAECE Consensus Statement states that electrical isolation of the pulmonary veins (PVs) from the left atrium is "the cornerstone for most AF ablation procedures." Creation of transmural, continuous, and durable RF lesions is the objective of PV isolation (PVI). Conventional parameters of RF ablation with irrigated catheters involves the delivery of moderate power (20-40 W) for a relatively long duration (20-40 seconds) at a contact force range of 10-20 grams. Still, the incidence of acute PV reconnection remains frequent, occurring after PVI at a frequency 15-22%. While the mechanisms underlying PV reconnection are not entirely understood, catheter instability, tissue edema, and reversible non-transmural injury have been suggested as major contributor.

RF lesion formation results from two thermal heating phases; resistive and conductive heating. Resistive heating is highly dependent on RF power immediately creating a hot spot ~2 mm from the tip. This resistive heating phase creates a heat source that extends passively to deeper tissue layers during the conductive phase. Conductive heating is time dependent, with heat conducted from the hot spot into the deeper layers of the myocardium.

Modification of the relationship between the resistive and conductive heating phases, by increasing the resistive heating phase to deliver immediate heating to the full thickness of the LA tissue circumferential to the PVs, may achieve uniform, transmural lesions. By reducing the conductive heating phase collateral tissue damage could be limited. This can be achieved by delivering a large current for a short duration. Accordingly, there is a desire for an ablation catheter that resolves these and other issues of the art.

SUMMARY

In some examples, an ablation catheter system is disclosed for drug refractory symptomatic paroxysmal atrial fibrillation (PAF). The system can include an elongated body; an electrode assembly comprising a shell configured with an inner chamber and a wall defining a proximal portion and a distal portion, the wall of the distal portion having at least one aperture; and a micro-element extending through the inner chamber between the proximal portion and the distal portion, the micro-element having a distal end received in the at least one aperture, the distal end being at least coextensive with an outer surface of the wall. The system is configured to achieve acute procedural PVI success for all patients of a predetermined patient population suffering from PAF.

In some examples, an ablation catheter system is disclosed for drug refractory symptomatic paroxysmal atrial fibrillation (PAF). The system can include an elongated body; an electrode assembly comprising a shell configured with an inner chamber and a wall defining a proximal portion and a distal portion, the wall of the distal portion having at least one aperture; and a micro-element extending through the inner chamber between the proximal portion and the distal portion, the micro-element having a distal end received in the at least one aperture, the distal end being at least coextensive with an outer surface of the wall. The system is configured to achieve clinically improved total fluid delivered by the ablation catheter system and via intravenous line during PAF and RF ablation.

In some examples, an ablation catheter system is disclosed for drug refractory symptomatic paroxysmal atrial fibrillation (PAF). The system can include an elongated body; an electrode assembly comprising a shell configured with an inner chamber and a wall defining a proximal portion and a distal portion, the wall of the distal portion having at least one aperture; and a micro-element extending through the inner chamber between the proximal portion and the distal portion, the micro-element having a distal end received in the at least one aperture, the distal end being at least coextensive with an outer surface of the wall. The system is configured to achieve clinically improved safety and effectiveness resulting in approximately at least 80% less RF ablation time compared to ablation time of a previous clinically approved catheter system for treating PAF.

In some examples, an ablation catheter system is disclosed for drug refractory symptomatic paroxysmal atrial fibrillation (PAF). The system can include an elongated body; an electrode assembly comprising a shell configured with an inner chamber and a wall defining a proximal portion and a distal portion, the wall of the distal portion having at least one aperture; a micro-element extending through the inner chamber between the proximal portion and the distal portion, the micro-element having a distal end received in the at least one aperture, the distal end being at least coextensive with an outer surface of the wall; and an irrigation pump configured to deliver, by and through the elongated body, a continuous infusion of approximately 2 milliliters/minute of a treatment solution when not delivering RF energy during RF ablation. The system is configured to achieve clinically improved safety and effectiveness for PAF with a contact force between the catheter system and a target site working ranging between approximately 5-30 grams.

In some examples, an ablation catheter system is disclosed for drug refractory symptomatic paroxysmal atrial fibrillation (PAF). The system can include an elongated body; an electrode assembly comprising a shell configured with an inner chamber and a wall defining a proximal portion and a distal portion, the wall of the distal portion having at least one aperture; a micro-element extending through the inner chamber between the proximal portion and the distal portion, the micro-element having a distal end received in the at least one aperture, the distal end being at least coextensive with an outer surface of the wall; and an irrigation pump configured to deliver, by and through the elongated body, a continuous infusion of approximately 2 milliliters/minute of a treatment solution when not delivering RF energy during RF ablation. The system is configured to achieve clinically improved safety and effectiveness for PAF with substantially shorter total procedure, ablation, fluoroscopy, and radiofrequency application times.

In some examples, an ablation catheter system is disclosed for drug refractory symptomatic paroxysmal atrial fibrillation (PAF). The system can include an elongated body; an electrode assembly comprising a shell configured with an inner chamber and a wall defining a proximal portion and a distal portion, the wall of the distal portion having at least one aperture; a micro-element extending through the inner chamber between the proximal portion and the distal portion, the micro-element having a distal end received in the at least one aperture, the distal end being at least coextensive with an outer surface of the wall; and an irrigation pump configured to deliver, by and through the elongated body, a continuous infusion of approximately 2 milliliters/minute of a treatment solution when not delivering RF energy during RF ablation. The system is configured to achieve zero incidence of steam pop occurrence in both left and right atrial ablations using the ablation catheter system at a predetermined irrigation fluid rate and power setting that includes 90 W.

In some examples, the system is configured to clinically improve treatment of complex cardiac arrhythmias.

In some examples, the predetermined patient population size is at least about 50 patients.

In some examples, the system includes an irrigation pump for delivering a treatment solution through the catheter system to the treatment site.

In some examples, the system includes a force sensory system for detecting contact force applied by the catheter system to the treatment site during use.

In some examples, the system is configured only for use in the ablation procedure with irrigation flow and maintaining a flow rate of 8 milliliters/minute.

In some examples, clinical safety is determined by proportion of subjects with any primary adverse event (PAE) occurring within 7 days of ablation procedure.

In some examples, a clinical effectiveness endpoint is determined by proportion of subjects that are free from documented atrial arrhythmia (atrial fibrillation (AF) episodes at Month 12 for at least about 9 months following the ablation procedure.

In some examples, a clinical effectiveness endpoint is determined by proportion of subjects that are free from documented atrial tachycardia (AT) episodes at Month 12 for at least about 9 months following the ablation procedure.

In some examples, a clinical effectiveness endpoint is determined by proportion of subjects that are free from documented atrial flutter (AFL)) episodes at Month 12 for at least about 9 months following the ablation procedure.

In some examples, clinical safety is determined by proportion of subjects with primary adverse events within about 7 days of the ablation procedure.

In some examples, the catheter system is configured to reduce, for a predetermined patient population, incidence of serious adverse events during and after the ablation procedure of the catheter system up to 3 months following procedure.

In some examples, the catheter system is configured to clinically improve acute procedural success as defined by the proportion of subjects with electrical isolation of PVs at the end of the procedure.

In some examples, the catheter system is configured to clinically improve acute procedural success as defined by the proportion of subjects with electrical isolation of PVs using only an ablation mode.

In some examples, the ablation mode is about 90 W at a flow rate of 8 milliliters/minute.

In some examples, the ablation mode is at least greater than about 50 W at a flow rate of 8 milliliters/minute.

In some examples, the ablation mode is about 90 W for at least about a 4 s duration of time with an RF generator.

In some examples, the catheter system is configured to clinically improve effectiveness as defined by the proportion of subjects with electrical isolation of PVs at all power settings combined the proportion of subjects with electrical isolation of PVs after first pass isolation.

In some examples, the catheter system is configured to clinically improve effectiveness as defined by the proportion of subjects with electrical isolation of PVs at all power settings combined the proportion of subjects with electrical isolation of PVs after a waiting period.

In some examples, the catheter system is configured to clinically improve effectiveness as defined by the proportion of subjects with electrical isolation of PVs at all power settings combined the proportion of subjects with electrical isolation of PVs after adenosine challenge.

In some examples, the catheter system is configured to clinically improve effectiveness as defined by the proportion of subjects and proportion of PVs with touch-up to remove ablation of acute reconnection among all targeted veins and touch-up location.

In some examples, the catheter system is configured to clinically improve effectiveness as defined by the proportion of subjects the anatomical location of acute PV reconnection after first encirclement.

In some examples, the catheter system is configured to clinically improve incidence of unanticipated adverse device effects during and following the ablation procedure used with the catheter system.

In some examples, the catheter system is configured to clinically improve incidence of serious adverse events and incidence of bleeding complication within 7 days of the ablation procedure performed by the catheter system.

In some examples, the catheter system is configured to clinically improve incidence of serious adverse events and incidence of bleeding complication between 7-30 days after the ablation procedure performed by the catheter system.

In some examples, the catheter system is configured to clinically improve incidence of serious adverse events and incidence of bleeding complication at least 30 days after the ablation procedure performed by the catheter system.

In some examples, the incidence of bleeding complication is defined as major bleeding.

In some examples, incidence of bleeding complication is defined as clinically relevant non-major.

In some examples, incidence of bleeding complication is defined as minor bleeding.

In some examples, the catheter system is configured to clinically improve, for a predetermined patient population, a coagulum rate associated with RF ablation of the catheter system.

In some examples, the catheter system is configured to clinically improve, for a predetermined patient population, a steam pop rate compared with a prior clinically approved ablation catheter.

In some examples, the prior clinically approved ablation catheter is configured to perform RF ablation at approximately 50 W or less with a flow rate of flow rate of 8 milliliters/minute and the catheter system is configured to perform RF ablation at approximately 90 W with a flow rate of 8 milliliters/minute.

In some examples, the catheter system is configured to clinically improve lesion dimensions, for a predetermined patient population, including max depth, max diameter and surface diameter, as compared a prior clinically approved ablation catheter.

In some examples, the catheter system is configured to clinically improve average power used during ablation, for a predetermined patient population, as compared a prior clinically approved ablation catheter.

In some examples, the catheter system is configured to clinically improve maximum electrode temperature used during ablation, for a predetermined patient population, as compared a prior clinically approved ablation catheter.

In some examples, the catheter system is configured to clinically improve impedance drop during ablation, for a predetermined patient population, as compared a prior clinically approved ablation catheter.

In some examples, the catheter system is configured to clinically improve RF energy delivery at a target site.

In some examples, the catheter system is configured to clinically improve acute isolation of the pulmonary vein.

In some examples, the catheter system is configured to clinically improve pace from ring electrodes and microelectrodes during idle-state and during RF ablation.

In some examples, the catheter system is configured to clinically improve temperature feedback during ablation as compared a prior clinically approved ablation catheter.

In some examples, the chamber is adapted to receive fluid and the chamber has a plurality of irrigation apertures configured to allow fluid to flow from inside the chamber to outside the chamber.

In some examples, the distal end of the micro-element includes an exposed portion outside of the wall of the shell.

In some examples, the micro-element includes a micro-electrode element at its distal end and the at least one wire is attached to the micro-electrode element.

In some examples, the micro-element is configured for temperature sensing.

In some examples, the system includes a plurality of micro-elements each having a distal end, wherein the distal ends of the micro-elements are arranged in a radial pattern in the distal portion of the electrode about a longitudinal axis of the electrode.

In some examples, the plurality ranges between about two and six.

In some examples, the plurality is six.

In some examples, the system includes a first plurality of first micro-elements configured for impedance sensing and a second plurality of second micro-elements configured for temperature sensing.

In some examples, distal ends of the first micro-elements are arranged in a radial pattern along a circumference of the distal portion of the shell about a longitudinal axis of the electrode.

In some examples, distal ends of the second micro-elements are also arranged in a radial pattern along the circumference, interspersed between the first micro-elements.

In some examples, the distal ends of the second micro-elements are arranged in a radial pattern along a different circumference of the distal portion of the shell about the longitudinal axis of the electrode.

In some examples, the exposed portion extends at an angle having a distal component and a radial component relative to the longitudinal axis of the electrode.

In some examples, the exposed portion has an atraumatic configuration adapted to form a micro-depression in tissue without breaching the tissue.

In some examples, the system is configured to implement a method comprising selectively positioning a diagnostic catheter at a treatment site in the vasculature; selectively positioning the ablation catheter system according to any previous claim at the treatment site; performing PVI by ablating tissue at the treatment site with the ablation catheter system; and clinically improving, by the ablation catheter system, total fluid delivered by the ablation catheter system and via intravenous line during the ablation procedure.

In some examples, the system is configured to implement a method comprising inserting the ablation catheter system according to any preceding claim to a treatment site comprising cardiac tissue, the system comprising at least one electrode and at least one sensor into the body in proximity; ablating the cardiac tissue with the ablation catheter system; and achieving complete pulmonary vein isolation, by the ablation catheter system, for all patients of a predetermined patient population suffering from PAF.

In some examples, the system is configured to implement a method comprising inserting an ablation catheter system according to any preceding claim into a body of a living subject; urging the ablation catheter system into contact with a cardiac tissue in the body; generating ablative energy at a power output level at a level of current; transmitting the generated energy into the tissue via the ablation catheter system; ablating the cardiac tissue with the ablation catheter system; and clinically improving, by the ablation catheter system, safety and effectiveness resulting in approximately at least 80% less RF ablation time compared to ablation time of a previous clinically approved catheter system for treating PAF.

In some examples, the system is configured to implement a method comprising selectively positioning a diagnostic catheter at a treatment site in the vasculature; selectively positioning the ablation catheter system according to any previous claim at the treatment site; performing PVI by ablating tissue at the treatment site with the ablation catheter system; and clinically improving, by the ablation catheter system, safety and effectiveness for PAF with a contact force between the ablation catheter system and a target site working ranging between approximately 5-30 grams.

In some examples, the system is configured to implement a method comprising inserting the ablation catheter system according to any preceding claim to a treatment site comprising cardiac tissue, the system comprising at least one electrode and at least one sensor into the body in proximity; ablating the cardiac tissue with the ablation catheter system; achieving clinically improved safety and effectiveness for PAF with substantially shorter total procedure, ablation, fluoroscopy, and radiofrequency application times.

In some examples, the system is configured to implement a method comprising inserting an ablation catheter system according to any preceding claim into a body of a living subject; urging the ablation catheter system into contact with a cardiac tissue in the body; generating ablative energy at a power output level at a level of current; transmitting the generated energy into the tissue via the ablation catheter system; ablating the cardiac tissue with the ablation catheter system; and achieving, by the ablation catheter system, zero incidence of steam pop occurrence in both left and right atrial ablations using the ablation catheter system at a predetermined irrigation fluid rate and power setting that includes 90 W.

In some examples, a method is disclosed for performing clinically improved cardiac ablation, the method including selectively positioning a diagnostic catheter at a treatment site in the vasculature; selectively positioning an ablation catheter system according to any previous claim at the treatment site; performing PVI by ablating tissue at the treatment site with the ablation catheter system; and clinically improving, by the ablation catheter system, total fluid delivered by the ablation catheter system and via intravenous line during the ablation procedure.

In some examples, a method is disclosed for performing RF ablation on cardiac tissue during a pulmonary vein isolation procedure, the method including inserting an ablation catheter system according to any preceding claim to a treatment site comprising cardiac tissue, the system comprising at least one electrode and at least one sensor into the body in proximity; ablating the cardiac tissue with the ablation catheter system; and achieving complete pulmonary vein isolation, by the ablation catheter system, for all patients of a predetermined patient population suffering from PAF.

In some examples, a method is disclosed for performing RF ablation on cardiac tissue during a pulmonary vein isolation procedure, the method including inserting an ablation catheter system according to any preceding claim into a body of a living subject; urging the ablation catheter system into contact with a cardiac tissue in the body; generating ablative energy at a power output level at a level of current; transmitting the generated energy into the tissue via the ablation catheter system; ablating the cardiac tissue with the ablation catheter system; and clinically improving, by the ablation catheter system, safety and effectiveness resulting in approximately at least 80% less RF ablation time compared to ablation time of a previous clinically approved catheter system for treating PAF.

In some examples, a method is disclosed for performing clinically improved cardiac ablation, the method including selectively positioning a diagnostic catheter at a treatment site in the vasculature; selectively positioning an ablation catheter system according to any previous claim at the treatment site; performing PVI by ablating tissue at the treatment site with the ablation catheter system; and clinically improving, by the ablation catheter system, safety and effectiveness for PAF with a contact force between the ablation catheter system and a target site working ranging between approximately 5-30 grams.

In some examples, a method is disclosed for performing RF ablation on cardiac tissue during a pulmonary vein isolation procedure, the method including inserting an ablation catheter system according to any preceding claim to a treatment site comprising cardiac tissue, the system comprising at least one electrode and at least one sensor into the body in proximity; ablating the cardiac tissue with the ablation catheter system; and achieving clinically improved safety and effectiveness for PAF with substantially shorter total procedure, ablation, fluoroscopy, and radiofrequency application times.

In some examples, a method is disclosed for performing RF ablation on cardiac tissue during a pulmonary vein isolation procedure, the method including inserting an ablation catheter system according to any preceding claim into a body of a living subject; urging the ablation catheter system into contact with a cardiac tissue in the body; generating ablative energy at a power output level at a level of current; transmitting the generated energy into the tissue via the ablation catheter system; ablating the cardiac tissue with the ablation catheter system; and achieving, by the ablation catheter system, zero incidence of steam pop occurrence in both left and right atrial ablations using the ablation catheter system at a predetermined irrigation fluid rate and power setting that includes 90 W.

In some examples, for a target temperature of 50° C. and ablation duration of 4 s, the step of achieving further comprises applying an average force of approximately 7.5 grams by the ablation catheter system to the cardiac tissue during use.

In some examples, for a target temperature of 55° C. and ablation duration of 4 s, the step of achieving further comprises applying an average force of approximately 9.1 grams by the ablation catheter system to the cardiac tissue during use.

In some examples, for a target temperature of 60° C. and ablation duration of 4 s, the step of achieving further comprises applying an average force of approximately 17.7 grams by the ablation catheter system to the cardiac tissue during use.

In some examples, for a target temperature of 60° C. and ablation duration of 2 s, the step of achieving further comprises applying an average force of approximately 13.6 grams by the ablation catheter system to the cardiac tissue during use.

In some examples, a diseased heart is the treatment site of the method.

In some examples, the method includes clinically improving effective electrogram signal attenuation and clinically equivalent to or better lesions in all four cardiac chambers as compared to a prior clinically approved ablation catheter system.

In some examples, the method includes clinically reducing the total fluid delivered by the ablation catheter system to the treatment site during cardiac ablation by approximately 76.5% from a prior clinically approved ablation catheter system.

In some examples, the method includes delivering, by the ablation catheter system, no more than approximately 382 mL or less of treatment fluids to the treatment site during the ablation procedure.

In some examples, the method includes clinically reducing the total ablation procedure time by the ablation catheter system by approximately 50% from a prior clinically approved ablation catheter system.

In some examples, the method includes clinically, by the ablation catheter system, the total ablation procedure time to no more than approximately 105.2 minutes or less.

In some examples, the method includes clinically reducing the total ablation time by the ablation catheter system by approximately 62% from a prior clinically approved ablation catheter system.

In some examples, the method includes clinically, by the ablation catheter system, the total ablation time to no more than approximately 46 minutes or less.

In some examples, the method includes clinically reducing the total fluoroscopy time of the ablation catheter system by approximately 80% from a prior clinically approved ablation catheter system.

In some examples, the method includes clinically, by the ablation catheter system, the total fluoroscopy time to no more than approximately 6.6 minutes or less.

In some examples, the method includes clinically reducing the total RF application duration time of the ablation catheter system by approximately 83% from a prior clinically approved ablation catheter system.

In some examples, the method includes clinically reducing, by the ablation catheter system, total RF application duration time to no more than approximately 8.1 minutes or less.

In some examples, total procedure and fluoroscopy times for the ablation catheter system includes approximately 105 minutes and 6.6 minutes respectively.

In some examples, the method includes placing an esophageal temperature monitoring device; and monitoring esophageal temperature using the temperature monitoring device.

In some examples, the method includes confirming ACT in greater than or equal to 350 seconds before insertion of the ablation catheter system into the left atrium and maintain throughout the procedure.

In some examples, the method includes generating a left atrial anatomical map prior to an ablation procedure in the LA.

In some examples, the method includes using a pre-ablation flow rate delay of minimal 2 seconds before RF application.

In some examples, the method includes RF ablating via RF power application of up to 90 W for up to 4 seconds.

In some examples, the method includes moving the ablation catheter system from a first location of the treatment site to a second location of the treatment site.

In some examples, the step of moving the ablation catheter system includes moving the ablation catheter system approximately 4 millimeter if clinically effective ablation is achieved.

In some examples, the step of moving the ablation catheter system includes moving the ablation catheter system approximately if clinically effective ablation is achieved within 20 seconds as determined by electrogram reduction and/or impedance drop.

In some examples, the method includes performing, with the ablation catheter system, ablation of the left atrium and real time PV isolation.

In some examples, the method includes confirming entrance block in all targeted PVs by the diagnostic catheter.

In some examples, the method includes visualizing the treatment site and the ablation catheter system using fluoroscopy.

In some examples, the method includes minimizing risk of esophageal injury by using an esophageal temperature probe, wherein temperature rise is detected in the esophagus, then permitting tissue of the treatment site to cool to a predetermined temperature; and visualizing the esophagus under fluoroscopy.

In some examples, duration of ablation did not exceed 30 seconds on a posterior wall at the treatment site.

In some examples, the method includes clinically reducing PVI ablation time of the ablation catheter system, as compared to a prior clinically approved ablation catheter system, between first RF application and last RF application on a PV before isolation confirmed and circumferential ablation achieved.

In some examples, the method includes clinically reducing subject PVI ablation time of the ablation catheter system, as compared to a prior clinically approved ablation catheter system, between first RF application and last RF application before all PVI complete.

In some examples, the method includes clinically reducing total ablation time of the ablation catheter system, as compared to a prior clinically approved ablation catheter system, between first RF application and last RF application before all PVI complete.

In some examples, total ablation time is determined by total procedure time from first femoral puncture to last catheter removal.

In some examples, the method includes clinically improving ablation parameters of the ablation catheter system during an ablation procedure, as compared to a prior clinically approved ablation catheter system, including temperature, impedance, power, contact force, and RF duration.

In some examples, the method includes clinically improving atrial mapping time.

In some examples, the method includes clinically improving LA catheter dwell time from ablation catheter LA insertion to ablation catheter removal from the LA.

In some examples, the method includes irrigating the cardiac tissue via the ablation catheter system.

In some examples, the method includes minimizing acute or minimal subendocardial hemorrhages in the chambers and mitral valves by using the ablation catheter system in eliminating or ameliorating persistent atrial fibrillation.

In some examples, the method includes demonstrating clinically improved safety and/or effectiveness of the ablation catheter system for patients of a predetermined patient population, the predetermined patient population being divided in three different arrhythmia subgroups: Ventricular Tachycardia, complex Atrial Tachycardia or re-do Paroxysmal Atrial Fibrillation, and Persistent Atrial Fibrillation.

In some examples, the method includes clinically improving safety and effectiveness of the ablation catheter system to at least one of the left atrium, right atrium, left ventricle, and right ventricle.

In some examples, use of an ablation catheter system is disclosed, including selectively positioning a diagnostic catheter at a treatment site in the vasculature; selectively positioning the ablation catheter system according to any previous claim at the treatment site; performing PVI by ablating tissue at the treatment site with the ablation catheter system; and clinically improving, by the ablation catheter system, total fluid delivered by the ablation catheter system and via intravenous line during the ablation procedure.

In some examples, use of an ablation catheter system is disclosed, including inserting the ablation catheter system according to any preceding claim to a treatment site comprising cardiac tissue, the system comprising at least one electrode and at least one sensor into the body in proximity; ablating the cardiac tissue with the ablation catheter system; and achieving complete pulmonary vein isolation, by the ablation catheter system, for all patients of a predetermined patient population suffering from PAF.

In some examples, use of an ablation catheter system is disclosed, including inserting the ablation catheter system according to any preceding claim into a body of a living subject; urging the ablation catheter system into contact with a cardiac tissue in the body; generating ablative energy at a power output level at a level of current; transmitting the generated energy into the tissue via the ablation catheter system; ablating the cardiac tissue with the ablation catheter system; and clinically improving, by the ablation catheter system, safety and effectiveness resulting in approximately at least 80% less RF ablation time compared to ablation time of a previous clinically approved catheter system for treating PAF.

In some examples, use of an ablation catheter system is disclosed, including selectively positioning a diagnostic catheter at a treatment site in the vasculature; selectively positioning the ablation catheter system according to any previous claim at the treatment site; performing PVI by ablating tissue at the treatment site with the ablation catheter system; and clinically improving, by the ablation catheter system, safety and effectiveness for PAF with a contact force between the ablation catheter system and a target site working ranging between approximately 5-30 grams.

In some examples, use of an ablation catheter system is disclosed, including inserting the ablation catheter system according to any preceding claim to a treatment site comprising cardiac tissue, the system comprising at least one electrode and at least one sensor into the body in proximity; ablating the cardiac tissue with the ablation catheter system; and achieving clinically improved safety and effectiveness for PAF with substantially shorter total procedure, ablation, fluoroscopy, and radiofrequency application times.

In some examples, use of an ablation catheter system is disclosed, including inserting the ablation catheter system according to any preceding claim into a body of a living subject; urging the ablation catheter system into contact with a cardiac tissue in the body; generating ablative energy at a power output level at a level of current; transmitting the generated energy into the tissue via the ablation catheter system; ablating the cardiac tissue with the ablation catheter system; and achieving, by the ablation catheter system, zero incidence of steam pop occurrence in both left and right atrial ablations using the ablation catheter system at a predetermined irrigation fluid rate and power setting that includes 90 W.

In some examples, for a target temperature of 50° C. and ablation duration of 4 s, the step of achieving comprises applying an average force of approximately 7.5 grams by the ablation catheter system to the cardiac tissue during use.

In some examples, for a target temperature of 55° C. and ablation duration of 4 s, the step of achieving further comprises applying an average force of approximately 9.1 grams by the ablation catheter system to the cardiac tissue during use.

In some examples, for a target temperature of 60° C. and ablation duration of 4 s, the step of achieving further comprises applying an average force of approximately 17.7 grams by the ablation catheter system to the cardiac tissue during use.

In some examples, for a target temperature of 60° C. and ablation duration of 2 s, the step of achieving further comprises applying an average force of approximately 13.6 grams by the ablation catheter system to the cardiac tissue during use.

In some examples, a diseased heart is the treatment site of the method.

In some examples, the use includes clinically improving effective electrogram signal attenuation and clinically equivalent to or better lesions in all four cardiac chambers as compared to a prior clinically approved ablation catheter system.

In some examples, the use includes clinically reducing the total fluid delivered by the ablation catheter system to the treatment site during cardiac ablation by approximately 76.5% from a prior clinically approved ablation catheter system.

In some examples, the use includes delivering, by the ablation catheter system, no more than approximately 382 mL or less of treatment fluids to the treatment site during the ablation procedure.

In some examples, the use includes clinically reducing the total ablation procedure time by the ablation catheter system by approximately 50% from a prior clinically approved ablation catheter system.

In some examples, the use includes clinically, by the ablation catheter system, the total ablation procedure time to no more than approximately 105.2 minutes or less.

In some examples, the use includes clinically reducing the total ablation time by the ablation catheter system by approximately 62% from a prior clinically approved ablation catheter system.

In some examples, the use includes clinically, by the ablation catheter system, the total ablation time to no more than approximately 46 minutes or less.

In some examples, the use includes clinically reducing the total fluoroscopy time of the ablation catheter system by approximately 80% from a prior clinically approved ablation catheter system.

In some examples, the use includes clinically, by the ablation catheter system, the total fluoroscopy time to no more than approximately 6.6 minutes or less.

In some examples, the use includes clinically reducing the total RF application duration time of the ablation catheter system by approximately 83% from a prior clinically approved ablation catheter system.

In some examples, the use includes clinically reducing, by the ablation catheter system, total RF application duration time to no more than approximately 8.1 minutes or less.

In some examples, total procedure and fluoroscopy times for the ablation catheter system included approximately 105 minutes and 6.6 minutes respectively.

In some examples, the use includes placing an esophageal temperature monitoring device; and monitoring esophageal temperature using the temperature monitoring device.

In some examples, the use includes confirming ACT in greater than or equal to 350 seconds before insertion of the ablation catheter system into the left atrium and maintain throughout the procedure.

In some examples, the use includes generating a left atrial anatomical map prior to an ablation procedure in the LA.

In some examples, the use includes using a pre-ablation flow rate delay of minimal 2 seconds before RF application.

In some examples, the use includes RF ablating via RF power application of up to 90 W for up to 4 seconds.

In some examples, the use includes moving the ablation catheter system from a first location of the treatment site to a second location of the treatment site.

In some examples, the step of moving the ablation catheter system includes moving the ablation catheter system approximately 4 millimeter if clinically effective ablation is achieved.

In some examples, the step of moving the ablation catheter system includes moving the ablation catheter system approximately if clinically effective ablation is achieved within 20 seconds as determined by electrogram reduction and/or impedance drop.

In some examples, the use includes performing, with the ablation catheter system, ablation of the left atrium and real time PV isolation.

In some examples, the use includes confirming entrance block in all targeted PVs by the diagnostic catheter.

In some examples, the use includes visualizing the treatment site and the ablation catheter system using fluoroscopy.

In some examples, the use includes minimizing risk of esophageal injury by using an esophageal temperature probe, wherein temperature rise is detected in the esophagus, then permitting tissue of the treatment site to cool to a predetermined temperature; and visualizing the esophagus under fluoroscopy.

In some examples, the use includes a duration of ablation did not exceed 30 seconds on a posterior wall at the treatment site.

In some examples, the use includes clinically reducing PVI ablation time of the ablation catheter system, as compared to a prior clinically approved ablation catheter system, between first RF application and last RF application on a PV before isolation confirmed and circumferential ablation achieved.

In some examples, the use includes clinically reducing subject PVI ablation time of the ablation catheter system, as compared to a prior clinically approved ablation catheter system, between first RF application and last RF application before all PVI complete.

In some examples, the use includes clinically reducing total ablation time of the ablation catheter system, as compared to a prior clinically approved ablation catheter system, between first RF application and last RF application before all PVI complete.

In some examples, the use includes total ablation time is determined by total procedure time from first femoral puncture to last catheter removal.

In some examples, the use includes clinically improving ablation parameters of the ablation catheter system during an ablation procedure, as compared to a prior clinically approved ablation catheter system, including temperature, impedance, power, contact force, and RF duration.

In some examples, the use includes clinically improving atrial mapping time.

In some examples, the use includes clinically improving LA catheter dwell time from ablation catheter LA insertion to ablation catheter removal from the LA.

In some examples, the use includes irrigating the cardiac tissue via the ablation catheter system.

In some examples, the use includes minimizing acute or minimal subendocardial hemorrhages in the chambers and mitral valves by using the ablation catheter system in eliminating or ameliorating persistent atrial fibrillation.

In some examples, the use includes demonstrating clinically improved safety and/or effectiveness of the ablation catheter system for patients of a predetermined patient population, the predetermined patient population being divided in three different arrhythmia subgroups: Ventricular Tachycardia, complex Atrial Tachycardia or re-do Paroxysmal Atrial Fibrillation, and Persistent Atrial Fibrillation.

In some examples, the use includes clinically improving safety and effectiveness of the ablation catheter system to at least one of the left atrium, right atrium, left ventricle, and right ventricle.

In some examples, a system is disclosed for drug refractory symptomatic paroxysmal atrial fibrillation (PAF). The system includes an elongated body; an electrode assembly coupled to the elongated body and comprising a shell configured with an inner chamber and a wall defining a proximal portion and a distal portion, the wall of the distal portion having at least one aperture; a micro-element extending through the inner chamber between the proximal portion and the distal portion, the micro-element having a distal end received in the at least one aperture, the distal end being at least coextensive with an outer surface of the wall. The system is configured with an ablation mode including a power setting of approximately 90 W applied to tissue for approximately four (4) second increments with a break period of approximately 4 seconds between applications.

In some examples, the ablation mode causes a maximum tissue temperature of approximately 76° C.

In some examples, the system includes an irrigation pump configured to deliver an infusion of treatment solution by and through the elongated body. The irrigation pump is configured to deliver approximately 2 milliliters/minute of treatment solution when RF energy is not being delivered during RF ablation. The irrigation pump is configured to deliver approximately 8 milliliters/minute of treatment solution when RF energy is not being delivered during RF ablation.

In some examples, a force sensory system is included for detecting contact force applied by the catheter system to the treatment site during use, the contact force between the system and a target site ranging between approximately 5-30 grams.

In some examples, the system is configured to achieve zero incidence of steam pop occurrence in both left and right atrial ablations using the ablation mode.

In some examples, the ablation mode causes an increase of a maximum tissue temperature by at least about 13% between first and second ablation applications.

In some examples, the ablation mode causes an approximately 40% deeper lesion between first and second ablation applications, wherein the ablation mode further includes a contact force between the ablation catheter system and a target site ranging between approximately 10-30 g.

In some examples, the ablation mode causes an approximately 40% deeper lesion between first and second ablation applications and avoids formation of char, coagulum, steam pop.

In some examples, the ablation mode includes a point-by-point "kissing" ablation approach causing a continuous and transmural linear lesion line at the atrial wall with minimal over-lapped lesions.

In some examples, the ablation mode includes a temperature control and irrigation link.

In some examples, the electrode assembly includes one or more ring electrodes and microelectrodes the catheter system being configured to clinically improve pace from one or more ring electrodes and microelectrodes during idle-state and during RF ablation.

In some examples, the system is configured to achieve approximately at least 80% less RF ablation time compared to ablation time of a previous clinically approved catheter system for treating PAF.

In some examples, the distal end of the micro-element comprising an exposed portion outside of the wall of the shell, the micro-element configured for temperature sensing.

In some examples, the micro-element further comprising a first plurality of first micro-elements configured for impedance sensing and a second plurality of second micro-elements configured for temperature sensing. The distal ends of the first micro-elements can be arranged in a radial pattern along a circumference of the distal portion of the shell about a longitudinal axis of the electrode assembly.

In some examples, a method or use is disclosed, including selectively positioning an ablation catheter system at a treatment site; and ablating tissue at the treatment site with the ablation catheter system using a power setting of approximately 90 W applied to tissue for approximately four (4) second increments with a break period of approximately 4 seconds between applications.

In some examples, the method includes achieving, by the ablation catheter system, a maximum tissue temperature of approximately 76° C. to the treatment site during the ablation procedure.

In some examples, the step of ablating tissue includes increasing of a maximum tissue temperature by at least about 13% between first and second ablation applications.

In some examples, the step of ablating tissue includes a point-by-point "kissing" ablation approach causing a continuous and transmural linear lesion line at the atrial wall with minimal over-lapped lesions.

In some examples, the step of ablating tissue includes achieving a lesion depth approximately 40% deeper between first and second ablation applications, the method or use further comprising applying to the treatment site, by a distal end of the ablation catheter system, a contact force ranging between approximately 5-30 grams.

In some examples, the ablation catheter system includes an elongated body; an electrode assembly comprising a shell configured with an inner chamber and a wall; and a micro-element extending through the inner chamber between the proximal portion and the distal portion, the micro-element having a distal end received in the at least one aperture, the distal end being at least coextensive with an outer surface of the wall.

In some examples, the predetermined patient population size is at least about 50 patients.

In some examples, the method or use includes delivering, by and through the elongated body, a continuous infusion of approximately 8 milliliters/minute of treatment solution when not delivering RF energy during RF ablation.

In some examples, the method or use includes moving the ablation catheter system approximately 4 millimeter if clinically effective ablation is achieved within 20 seconds as determined by electrogram reduction and/or impedance drop.

In some examples, a method or use is disclosed, including delivering an ablation catheter system to a treatment site comprising cardiac tissue, the system comprising at least one electrode and at least one sensor in proximity with the other; ablating cardiac tissue with the ablation catheter system at a predetermined irrigation fluid rate and power setting comprising approximately 90 W; and achieving approximately zero incidence of steam pop occurrence in both left and right atrial ablations and complete pulmonary vein isolation, by the ablation catheter system, for all patients of a predetermined patient population suffering from PAF.

In some examples, the ablation catheter system includes an elongated body; an electrode assembly comprising a shell configured with an inner chamber and a wall; and a micro-element extending through the inner chamber between the proximal portion and the distal portion, the micro-element having a distal end received in the at least one aperture, the distal end being at least coextensive with an outer surface of the wall.

In some examples, the step of achieving complete pulmonary vein isolation further comprises applying an average force of approximately 7.5 grams by the ablation catheter system to the cardiac tissue during use and achieving a target temperature of approximately 50° C. and ablation duration of approximately 4 seconds.

In some examples, the step of achieving complete pulmonary vein isolation further comprises applying an average force of approximately 9 grams by the ablation catheter system to the cardiac tissue during use and achieving a target temperature of approximately 55° C. and ablation duration of approximately 4 seconds.

In some examples, the step of achieving complete pulmonary vein isolation further comprises applying an average force of approximately 17.7 grams by the ablation catheter system to the cardiac tissue during use and achieving a target temperature of approximately 1360° C. and ablation duration of approximately 4 seconds.

In some examples, the step of achieving complete pulmonary vein isolation further comprises applying an average force of approximately 13.6 grams by the ablation catheter system to the cardiac tissue during use and achieving a target temperature of approximately 1360° C. and ablation duration of approximately 2 seconds.

In some examples, the method or use includes delivering, by the ablation catheter system, the predetermined irrigation flow rate of approximately 380 mL or less of treatment fluids to the treatment site during the ablation procedure.

In some examples, the step of achieving complete pulmonary vein isolation includes a total ablation procedure time less than or equal to approximately 105 minutes.

In some examples, the step of achieving complete pulmonary vein isolation includes a total ablation procedure time less than or equal to approximately 46 minutes.

In some examples, the step of achieving complete pulmonary vein isolation includes a total fluoroscopy time of less than or equal to approximately 6.5 minutes or less.

In some examples, the step of achieving complete pulmonary vein isolation includes a total RF application duration time of approximately 8 minutes or less.

In some examples, the step of achieving complete pulmonary vein isolation includes a total RF application duration time of 30 seconds on a posterior wall of the treatment site.

In some examples, the step of ablating the cardiac tissue includes a point-by-point "kissing" ablation approach causing a continuous and transmural linear lesion line at the atrial wall with minimal over-lapped lesions.

To the accomplishment of the foregoing and related ends, certain illustrative aspects are described herein in connection with the following description and the appended drawings. These aspects are indicative, however, of but a few of the various ways in which the principles of the claimed subject matter can be employed and the claimed subject matter is intended to include all such aspects and their equivalents. Other advantages and novel features can become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 12 shows a table summarizing the equipment used in the study of this disclosure.

FIG. 13 shows a table summarizing antiarrhythmic drugs (AADs) and impact on primary effectiveness classification for the study of this disclosure.

FIG. 14 shows a table summarizing ablation mode and flow rate settings during RF applications.

FIG. 15 shows a table summarizing the required schedule for subject treatment and evaluations in the study of this disclosure.

FIG. 16 shows a table summarizing primary adverse events as determined in the study of this disclosure.

FIG. 17 shows a table summarizing primary adverse events as determined in the study of this disclosure.

FIG. 18 shows show a table summarizing primary adverse events as determined in the study of this disclosure.

FIG. 19 shows show a table summarizing primary adverse events as determined in the study of this disclosure.

FIG. 20 is a table summarizing intensity or severity according to the study of this disclosure.

FIG. 21 is a table summarizing AE outcomes as assessed in the study of this disclosure.

FIG. 22 is a graph summarizing patient characteristics and medical history in the study of this disclosure.

FIG. 23 is a graph summarizing acute pulmonary vein reconnection in the study of this disclosure.

FIG. 24 is a graph summarizing primary adverse events in the safety population of the study of this disclosure.

FIG. 27A is a table summarizing comparative procedural outcomes between the catheter of this disclosure and prior clinically approved devices.

FIG. 27B is a table summarizing comparative procedural outcomes between the catheter of this disclosure and prior clinically approved devices.

FIG. 28 is a table summarizing results for ablations by setting on all locations of the study.

FIG. 29 is a table summarizing results for ablations by setting on all locations of the study.

FIG. 33 depicts a graphical overview of one method or use according to this disclosure.

FIG. 34 depicts a graphical overview of one method or use according to this disclosure.

FIG. 36 depicts a graphical overview of one method or use according to this disclosure.

FIG. 39 depicts a graphical overview of one method or use according to this disclosure.

DETAILED DESCRIPTION

Figure 1:
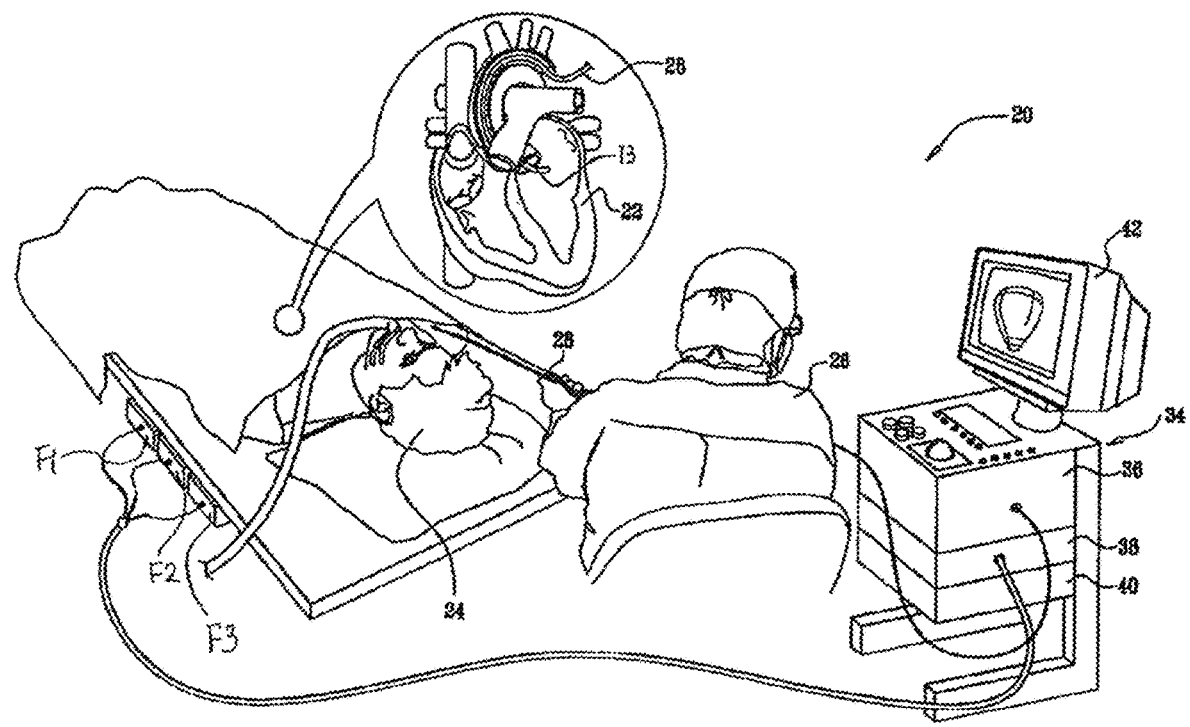
FIG. 1 is a schematic overview of a catheter-based medical system, in accordance with an embodiment of the present disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

As used herein, the terms "about" or "approximately" for any numerical values or ranges indicate a suitable dimensional tolerance that allows the part or collection of components to function for its intended purpose as described herein. More specifically, "about" or "approximately" can refer to the range of values ±10% of the recited value, e.g. "about 90%" can refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, or any other individual or delivery instrumentation associated with delivery of a RF ablation catheter for the treatment of atrial fibrillation to a subject.

As discussed herein, the term "safety", as it relates to devices used in ablating cardiac tissue, related delivery systems, or method of treatment refers to a relatively low severity of adverse events, including adverse bleeding events, infusion or hypersensitivity reactions. Adverse bleeding events can be the primary safety endpoint and include, for example, major bleeding, minor bleeding, and the individual components of the composite endpoint of any bleeding event.

As discussed herein, unless otherwise noted, the term "clinically effective" (used independently or to modify the term "effective") can mean that it has been proven by a clinical trial wherein the clinical trial has met the approval standards of U.S. Food and Drug Administration, EMEA or a corresponding national regulatory agency. For example, a clinical study can be an adequately sized, randomized, double-blinded controlled study used to clinically prove the effects of the cardiac ablation device(s) and related system(s) of this disclosure. Most preferably to clinically prove the effects of the device(s) with respect to all targeted pulmonary veins, for example, to achieve a clinically effective outcome in for the patient and/or achieve pulmonary vein isolation in those afflicted veins.

In a preferred aspect, the solution of this disclosure is not a method for treatment of the human or animal body by surgery or therapy and is not a diagnostic method practiced on the human or animal body. For example, when the solution involves clinically improving at least one clinical attribute during use, the clinical attribute may not be related to a method for treatment of the human or animal body by surgery or therapy or a diagnostic method practiced on the human or animal body.

As discussed herein, the term "computed tomography" or CT means one or more scans that make use of computer-processed combinations of many X-ray measurements taken from different angles to produce cross-sectional (tomographic) images (virtual "slices") of specific areas of a scanned object, allowing the user to see inside the object without cutting. Such CT scans of this disclosure can refer to X-ray CT as well as many other types of CT, such as positron emission tomography (PET) and single-photon emission computed tomography (SPECT).

Figure 2:
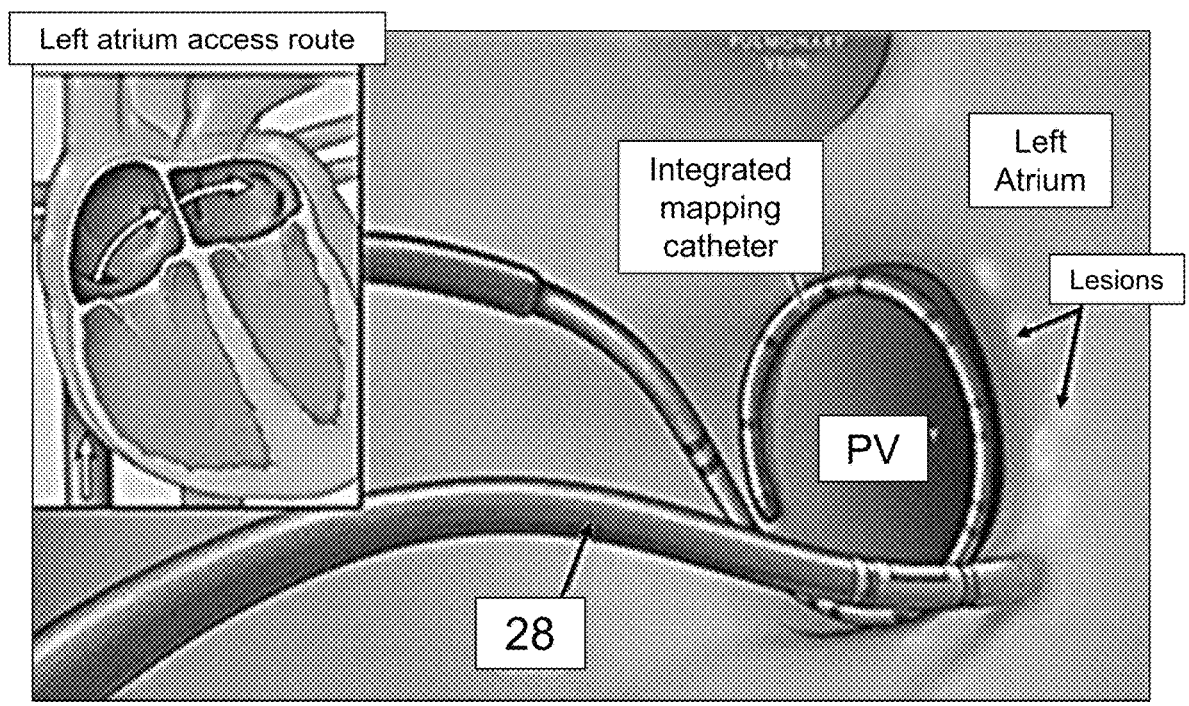
FIG. 2 illustrates an overview of the catheter of this disclosure being used to perform PVI.

The present disclosure is directed to a system and catheter for cardiac catheterization, where the catheter has a sensing assembly that provides signals representative of both position of the catheter and pressure exerted on a distal section of the catheter when it engages tissue. Compared to conventional position sensing assemblies and pressure sensing assemblies, sensing assemblies of the catheter are advantageously configured with serially-wired sensing structures to reduce the number of leads and/or their lengths for a simplified catheter structure that minimizes the risk of damaged or broken leads. FIG. 1 is a schematic illustration of a conventional system 20 for cardiac catheterization as known in the art. System 20 may comprise an invasive probe in the form of a catheter 28 and a control console 34. The signal processor 36 of the console 34 processes signals from sensors of the catheter 28 in order to determine the position coordinates of the distal section 13, typically including both location and orientation coordinates. Catheter 28 and corresponding features of the study of this disclosure can be understood as including features more clearly described in Appendix 1 which includes U.S. Pat. Nos. 8,357,152; 8,437,832; 8,535,308; 8,706,193; 8,784,413; 8,818,485; 8,900,228; 9,737,353; 9,445,725; 9,980,652; 10,213,856; 10,517,667; 10,405,920; 10,292,763; 10,441,354; 10,307,206; 10,201,385; and U.S. application Ser. Nos. 14/289,802;

15/793,433; 15/295,296; and Ser. No. 16/272,098; each of which are incorporated by reference in their entirety as if set forth verbatim herein. Relatedly, a similar method of position sensing is described in detail in U.S. Pat. Nos. 5,391, 199, 6,690,963, 6,484,118, 6,239,724, 6,618,612 and 6,332, 089, in PCT Patent Publication WO 96/05768, and in U.S. Patent Application Publications 2002/0065455, 2003/ 0120150 and 2004/0068178, all of whose disclosures are incorporated herein by reference and in Appendix 1. FIG. 2 illustrates an overview of the catheter of this disclosure being used to perform PVI.

It is important to note that there have been some published data on ablation with higher than standard power settings, usually 45 W to 50 W, with currently available ablation catheters. However, these largely retrospective studies were performed at a small number of sites with limited analysis of safety endpoints, and real-time tissue temperature monitoring was not possible with these catheters. On the other hand, another temperature-sensing irrigated catheter with a diamond-impregnated tip was shown to significantly reduce procedure time. See Iwasawa J, Koruth J S, Petru J, et al. Temperature-controlled radiofrequency ablation for pulmonary vein isolation in patients with atrial fibrillation. J Am Coll Cardiol 2017; 70: 542-53. However, this catheter was limited to 50 W and, thus, was unable to deliver 4-second test ablation mode lesions; lesions averaged 18.8±1.9 seconds each with this catheter.

It is important to note that the test ablation (90 W, 4 s) described in the study of this disclosure is different than all previous studies with a limit of 50 W. The test ablation mode referred to in the study of this disclosure was understood as 90 W at a flow rate of 8 milliliters/minute and is sometimes referred herein as QMODE+. The ability of the novel test ablation mode to modulate power based on temperature reduces the potential for electrode and tissue overheating, which could, in turn, help avoid char formation and steam pops. The safety profile observed with catheter 28 and corresponding test ablation mode was promising, with a low incidence of PAEs and no unexpected adverse device effects. Furthermore, because of the ability to highlight only local potentials and not far field potentials, microelectrodes have been useful to avoid radiofrequency delivery on scar tissue. The safety of test ablation will be further evaluated in larger clinical studies. One of the limitations of point-by-point catheter ablation is the longer procedure time associated with individual lesion creation; this prompted adoption of balloon-based catheters for PVI. Nonetheless, current balloon technologies are mostly limited to PV ablation. The current study demonstrated reduction of procedural time with test ablation, with shorter procedural times than typically observed with current commercially-available CF and non-CF catheters.

Figure 3A:
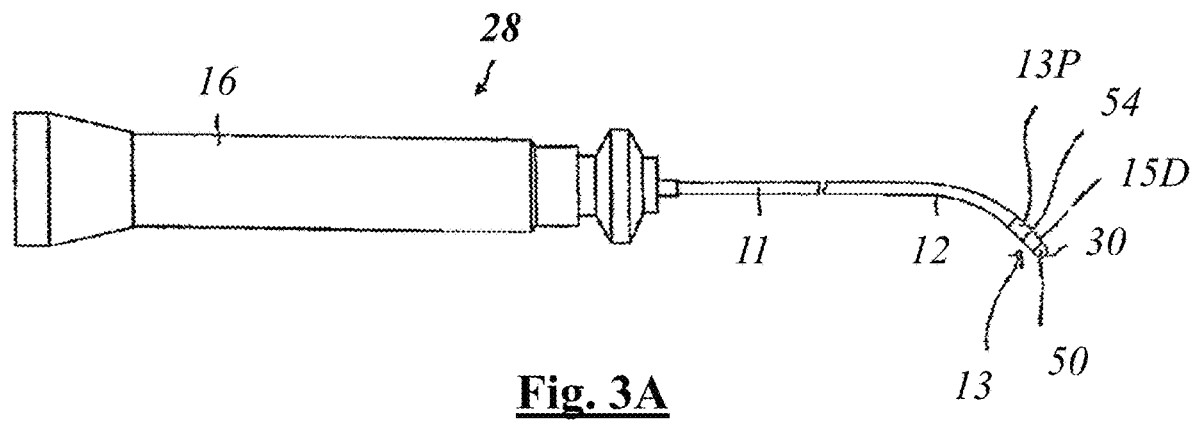
FIG. 3A is a side view of a catheter for use with the system of FIG. 1, in accordance with an embodiment of the present disclosure.

As shown in FIG. 3A, the catheter 28 can include an elongated catheter body 11, a deflectable intermediate section 12, a distal section 13 carrying at least a tip electrode 15 on its distal tip end 30, and a control handle 16. The catheter 28 can be one that is a steerable multi-electrode luminal catheter with a deflectable tip designed to facilitate electrophysiological mapping of the heart and to transmit radiofrequency (RF) current to the catheter tip electrode for ablation purposes. An operator 26, such as a cardiologist, can insert catheter 28 through the vascular system of a patient 24 so that a distal section 13 of the catheter enters a chamber of the patient's heart 22. The operator advances the catheter so that a distal tip 30 of the catheter engages endocardial tissue 70 at a desired location or locations. Catheter 28 is connected by a suitable connector at its proximal end to console 34. The console may include a RF generator, which supplies high-frequency electrical energy via the catheter for ablating tissue in the heart at the locations engaged by the distal section 13. For ablation, the catheter 28 can be used in conjunction with a dispersive pad (e.g., indifferent electrode). In this respect, the catheter 28 can include a shaft that measures 7.5 F with 8 F ring electrodes.

The catheter 28 can also have a force-sensing system that provides a real-time measurement of contact force between the catheter tip and the heart wall. A series of in vivo and in vitro experiments, including thigh muscle preparation model and in vivo beating heart experiments, were conducted in connection with the study of this disclosure to determine an appropriate test ablation mode setting that could be demonstrated to be safe and deliver uniform transmural lesion near the PV circumference. The main objective was to identify and evaluate an optimal ablation setting that allows maximal power output at the shortest duration possible, without char or steam-pop formation. A range of power (e.g., 50-100 W) and durations (3-15 seconds) were studied and analyzed and data from these evaluations suggests that using higher power to promote resistive heating while shortening the duration to limit the impact of conductive heating through adjacent tissue provides the optimal balance for efficiency, effectiveness and safety. The conclusion from these studies has been implemented as the test ablation mode using ablation parameters of 90 W for a duration of 4 s (irrigation setting at 8 milliliters/minute).

Figure 3B:
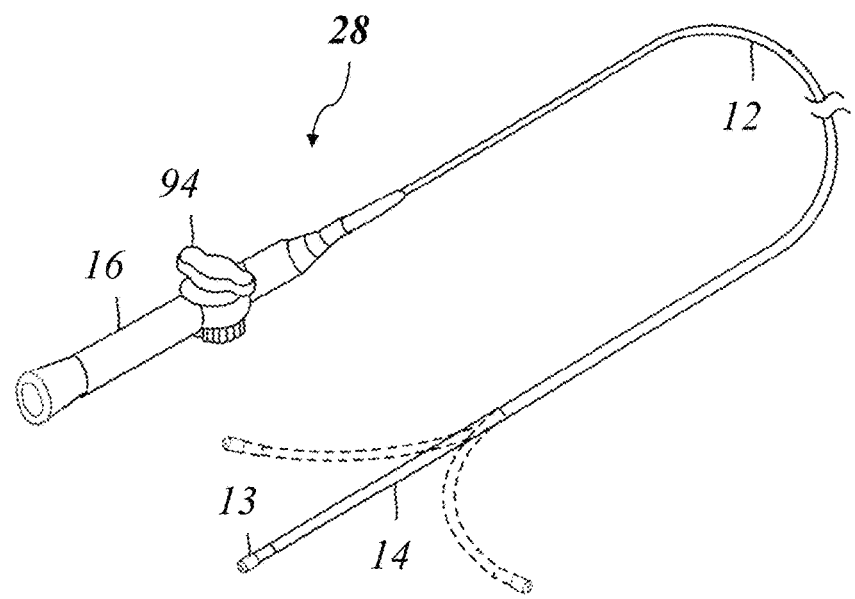
FIG. 3B is a perspective view of a catheter for use with the system of FIG. 1, in accordance with an embodiment of the present disclosure.

As shown in FIG. 3B, distal tip section 13 can include an electrode assembly 19 and at least one micro-element 20 having an atraumatic distal end adapted for direct contact with target tissue 22. Catheter body 12 can have a longitudinal axis, and an intermediate section 14 distal of the catheter body 12 that can be uni- or bi-directionally deflectable off-axis from the catheter body 12. Distal of the intermediate section 14 is the electrode assembly 19 carrying at least one micro-element. Proximal of the catheter body is control handle 16 that allows an operator to maneuver the catheter, including deflection of the intermediate section 14.

The shaft can be a relatively high torqueable with the distal tip section 13 being relatively deflectable containing electrode assembly 19 with an array of electrodes which includes a 3.5 mm tip dome with three microelectrodes. All of the electrodes may be used for recording and stimulation purposes. A rocker lever can be used to deflect the tip. The high-torque shaft also allows the plane of the curved tip to be rotated to facilitate accurate positioning of the catheter tip at the desired site. Three curve types configurations designated "D," "F," and "J" are available. The electrode assembly 19 serves to deliver RF energy from the RF generator to the desired ablation site. The electrode assembly 19 and ring electrodes can be made from noble metals. In some examples, the catheter 28 can also include six thermocouple temperature sensors that are embedded in the 3.5 mm tip electrode.

The RF generator software can be configured for cardiac ablation applications by generating RF energy for delivery to a site in the heart via catheter 28. The RF generator can include functions for controlling ablation parameters at the ablation electrodes of the catheter. Ablation parameters, such as power, impedance, ablation duration, and temperature are recorded and can be exported at the end of the procedure to a USB device. The RF generator can include a console that contains the hardware that provides the delivery of RF energy. A local monitor can be included with a user interface. The monitor can include control instructions for the generator and instruct the console what function to perform. It can also communicate with a workstation. A foot pedal can be included for the user to start and stop ablation.

At the proximal end of the catheter 28, a saline input port with a standard luer fitting can terminate from the open lumen. This saline port serves to permit the injection of normal saline to irrigate the electrode assembly 19. During ablation, heparinized normal saline can be passed through the internal lumen of the catheter 28 and through the electrode assembly 19, to irrigate and cool the ablation site as well as the electrode tip. An irrigation pump can be used in certain examples to control the saline irrigation.

Figure 4A:
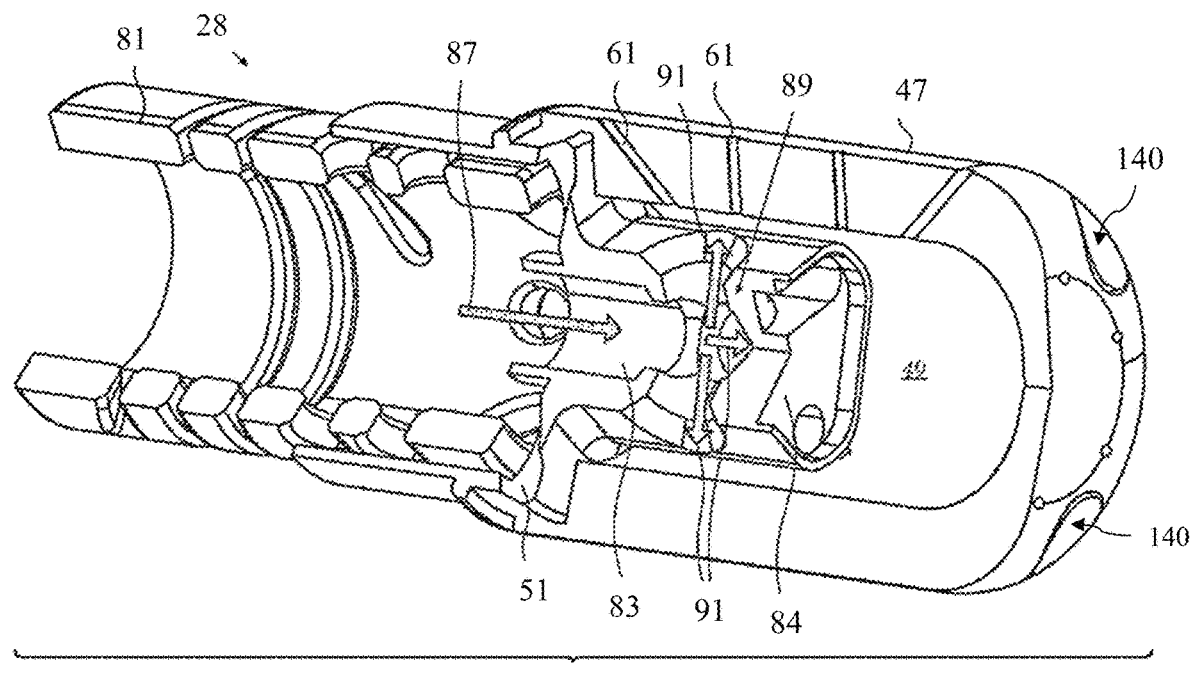
FIG. 4A is a cut-away sectional view of a distal segment of an ablation catheter showing a fluid-directing assembly in accordance with an embodiment of the invention.

Reference is now made to FIG. 4A, which shows a cut-away sectional view of distal tip section 13 of the catheter 28 in accordance with an embodiment. An irrigation assembly 51 mates with segment 81 of the catheter 28 and with the one or more electrodes 47 of assembly 19. The assembly 51 comprises an axial lumen 83 that conducts irrigation fluid distally toward a blocking terminus 85 that prevents the irrigation fluid from continuing in a forward direction. The irrigation fluid flow is indicated by an arrow 87. At the terminus 85 a plurality of channels 89 branch trans-axially outward at 90° angles to the axial lumen 83, diverting the flow outward as indicated by arrows 91. The irrigation fluid enters the lumen 49 transverse to the axis of the catheter 28, generally toward the lateral channels in the electrode 47, such as the channels 61.

If the irrigation path exited the lumen 83 in alignment with the axis of symmetry 53, irrigation flow through the channels 61 would be disfavored, because the flow would be required to reverse course, and to turn more than 90 degrees to enter the proximally angled channels, such as the channels 61. It is an advantage of the arrangement of FIG. 4A that the irrigation flow is relatively more evenly distributed to all the holes in the one or more electrodes 47 than if the flow exited the assembly 51 in a forward direction.

An irrigation pump can be used to control the saline irrigation. The catheter 28 can interface with standard recording equipment and a compatible RF generator via accessory extension cables with the appropriate connectors. The catheter 28 can include a location sensor embedded in the distal tip section 13 that transmits location and contact force information to the navigation system. An appropriate reference device can be required for location reference position purposes.

Figure 4B:
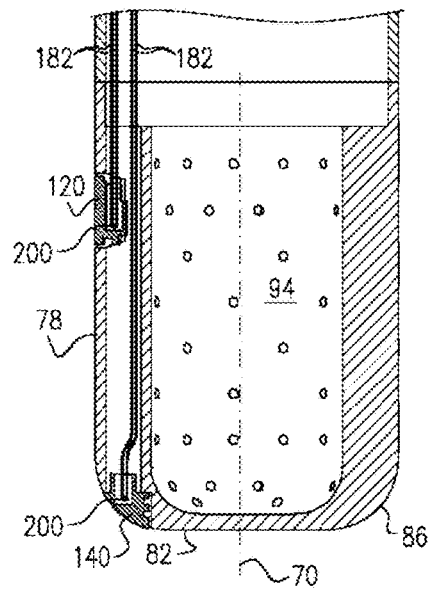
FIG. 4B is a schematic cross-section of the distal segment of the ablation catheter of FIG. 4A.

Turning to FIG. 4B is a schematic cross-section of the distal segment of the ablation catheter of FIG. 4A which as shown terminates at distal tip section 13, which is formed from a biocompatible conductor, such as platinum, palladium, gold, iridium, or an alloy of the aforementioned, and which has an axis of symmetry 70. The cross-section of the distal end illustrated in FIG. 4B is taken in a plane containing axis 70. An external surface of distal tip section 13 is divided into three regions: a cylindrical region 78 at the proximal end of the tip, a plane region 82 at the distal end of the tip, and a curved annular region 86 joining the cylindrical region to the plane region.

In the embodiment illustrated, distal tip section 13 is penetrated by irrigation channels, so that the outer surface is pierced by irrigation apertures that terminate the channels. Irrigation fluid may be directed into the irrigation channels via an internal manifold 94 formed in the distal tip. The irrigation fluid for the manifold is provided by a dedicated conduit (not shown in the figures) within the lumen.

At least one cavity is formed in the cylindrical region 78. At least one cavity is formed in the curved annular region 86 of the external surface. The embodiment described herein comprises three cavities which are distributed symmetrically with respect to axis 70, and three cavities of the curved annular region 86 are also distributed symmetrically with respect to the axis. and each cavity is configured to accept and mate with a respective microelectrode 120 of the prior discussed tip electrode 15. Each cavity of the curved annular region 86 is configured to accept and mate with a respective microelectrode 140. Microelectrodes 120 are configured to be inserted into respective cavities in the cylindrical region 78. Microelectrodes 140 are configured to be inserted into respective cavities of the curved annular region 86.

Figure 5A:
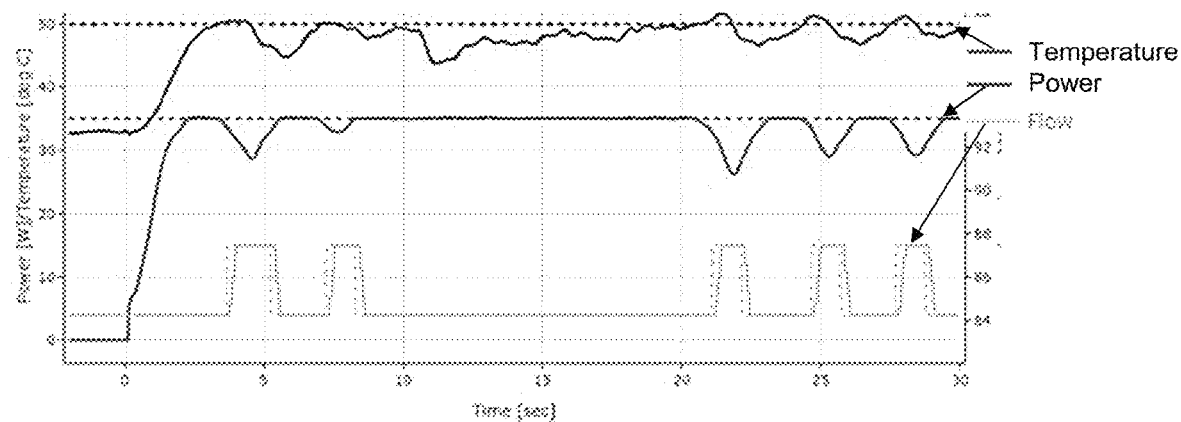
FIG. 5A shows a graph of the generator RF power delivery over time at 35 W for the study of this disclosure.
Figure 5B:
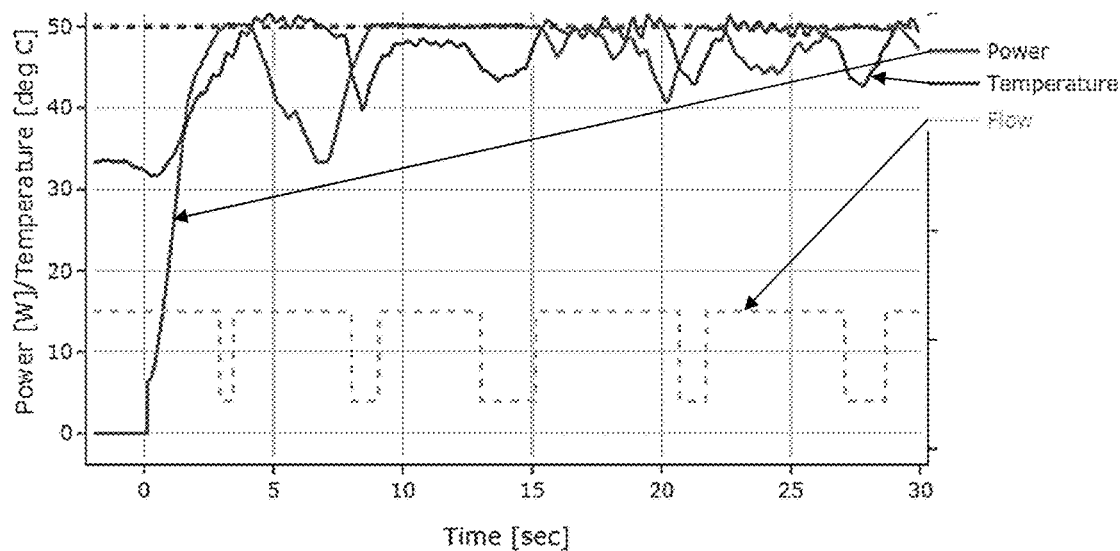
FIG. 5B shows a graph of the generator RF power delivery over time at 50 W for the study of this disclosure.

FIG. 5A shows a graph of the generator RF power delivery over time at 35 W for the study of this disclosure whereby maximum duration is set to 30 seconds. FIG. 5B shows a graph of the generator RF power delivery over time at 50 W for the study of this disclosure whereby maximum duration is set to 30 seconds.

Figure 6A:
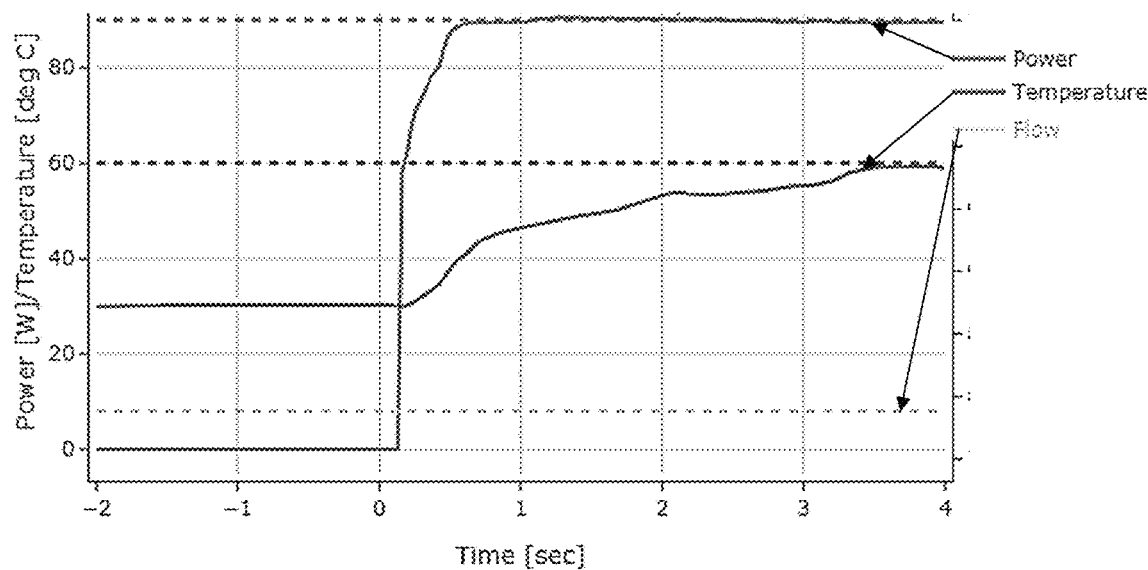
FIG. 6A shows a graph of the generator RF power delivery over time at 90 W for the study of this disclosure.
Figure 6B:
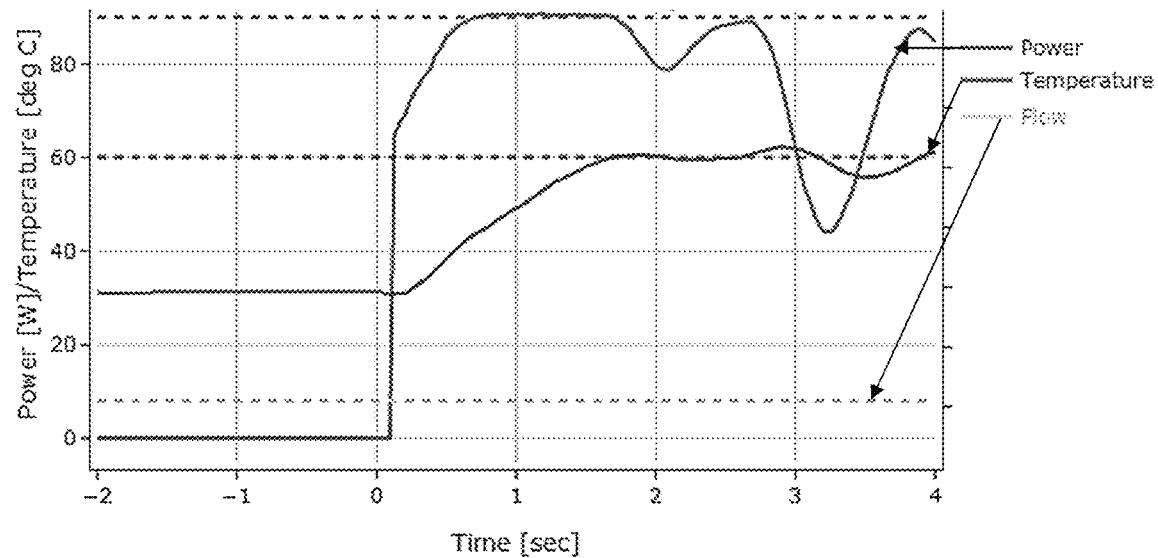
FIG. 6B shows a graph of the generator RF power delivery over time at 90 W for the study of this disclosure.

FIG. 6A shows a graph of the generator RF power delivery over time at 90 W for the study of this disclosure whereby maximum duration is set to 4 seconds. FIG. 6B shows a graph of the generator RF power delivery over time at 90 W for the study of this disclosure whereby maximum duration is set to 4 seconds. The approach depicted in FIGS. 6A-B is to titrate power. At this setting, power delivery is delivered at a constant irrigation flow of 8 milliliters/minute with no modulation given the short duration.

Figure 7:
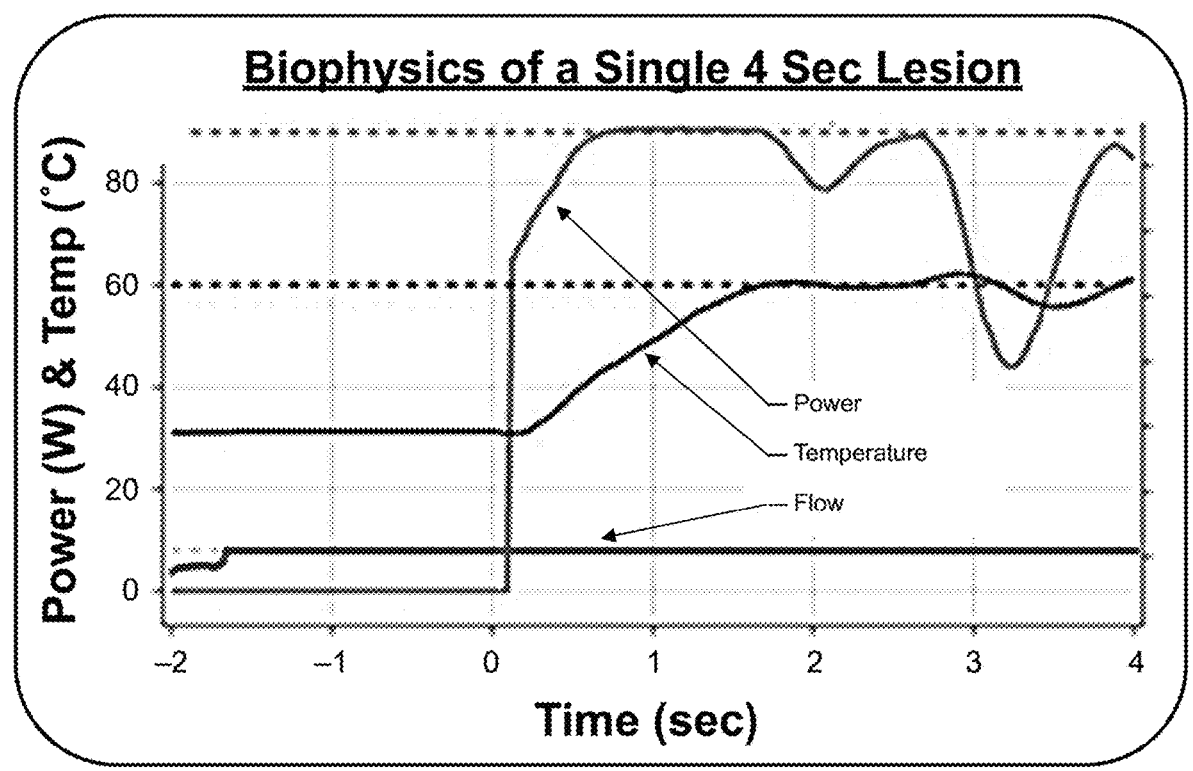
FIG. 7 is a graph showing biophysical parameters of an example ablation lesion.

FIG. 7 is a graph showing biophysical parameters of an example ablation lesion caused by catheter 28 of this disclosure. This includes a 2 sec pre-cooling phase, followed by a 4 second ablation lesion. Note the power modulation that is particularly striking in the last 1.5 seconds of energy delivery to maintain the target temperature of 60° C.

Figure 8:
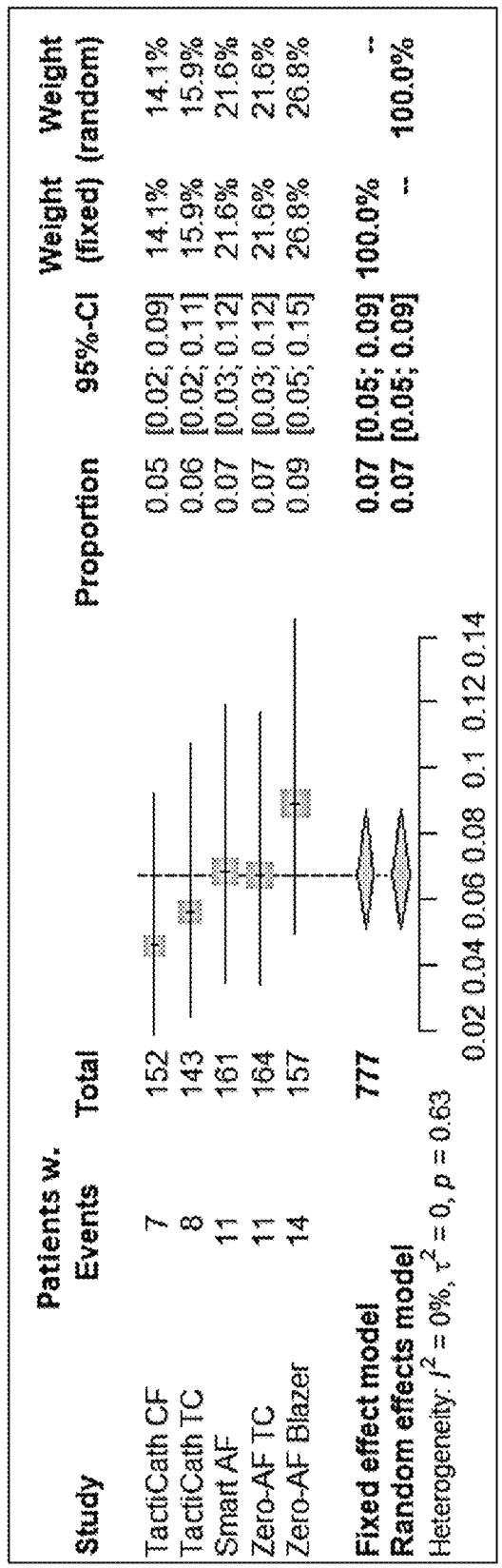
FIG. 8 summarizes meta-analysis of results for estimated average safety composite endpoints for prior devices for PAF.

In FIG. 8, a meta-analysis of results for estimated average safety composite endpoints for prior devices for PAF is presented. Data from recent clinical trials for devices similar to the catheter 28 in the current study were reviewed as a first step to deriving the performance goal for the safety endpoint. A meta-analysis approach was taken to estimate the average composite endpoint rate. Based on the plot, the upper bound of the 95% confidence interval was estimated to be equal to 9%. The proposed performance goal of 14% would reflect an approximately 50% increase in risk from the upper bound of the 95% CI.

Furthermore, prior studies have reported low rates of major complications (0.8%) with major centers worldwide reporting rates lower that <5% associated with catheter ablation. The most common complications associated with catheter ablation of AF included cardiac tamponade as reported at approximately 0.2 to 5% in catheter ablation of atrial fibrillation (AF) including mainly PVI mainly procedures.

The general incidence of pericardial effusion during AF ablation is around 1.2% to 1.3%. Cardiac perforation may result from catheter manipulation or application of radiofrequency current. Published risks of cardiac perforation range from <1% to 2.4%. However, the risk of perforation is decreased with advances in catheter technology. This potentially life-threatening injury may result in cardiac tamponade and may require percutaneous pericardial drainage or surgical repair. Significant hemodynamic compromise can result in neurologic injury or death. An increased risk of cardiac perforation may be associated with the use of a saline-irrigated electrode catheter due to its ability to create a larger, deeper RF lesion. This risk is greatest in a thin walled chamber (i.e., RA, LA, appendage, or RV).

Pulmonary vein stenosis (PVS) is a well-known complication of radiofrequency catheter ablation of atrial fibrillation. Incidence of severe PVS (>70% diameter reduction) was found to be <1% in a recent study with 976 subjects. Incidence of only 0.5% was reported in a large systematic review on complications of radiofrequency catheter ablation.

Moreover, since the left atrium has close anatomical proximity to the esophagus, catheter ablation on the LA posterior wall may thermally damage the esophagus and eventually generate an esophageal ulcer with a prevalence of 5% that rarely may progresses to an atrial esophageal fistula (AEF) with catastrophic consequences. Esophageal injury by endoscopy has a prevalence between 2.2 to 21%. Esophageal perforation is a dreaded complication of atrial fibrillation ablation that occurs in 0.02 to 11% of atrial fibrillation ablation procedures. Delayed diagnosis is associated with the development of atrial-esophageal fistula (AEF) and increased mortality. Complication rates for esophageal injury are quite varied, depending upon lesion location and type of lesion found (erythema, necrotic ulceration, perforation, or fistula formation). The incidence of AEF post-ablation of AF is supposed to be around 0.1% of the procedures. Studies using luminal temperature monitoring to identify potentially dangerous heating of the esophagus during ablation have not been able to demonstrate reduction in incidence.

Currently, phrenic nerve paralysis has been reported in less than 0.5%, with permanent paralysis between 0% to 0.4% when the isolation of right PV is not obtained during PV antra isolation and RF ablation is performed inside at carina the right PVs. A 2018 published study reported very low rates of PNP of 0.04% among 2,750 procedures. Prior to ablation in the region of the RSPV, investigators are encouraged to perform precautionary measures such as evaluation of proximity to the phrenic nerve and pacing maneuvers.

Death is also an uncommon complication associated with CA techniques. Overall incidence of death has been reported to be <0.1% to 0.4%. A 2010-published global survey provided an overall mortality rate of 0.1%. Another report from an international survey of AF ablation of 162 centers provided details on 32 deaths that occurred during or after AF ablation procedures in 32,569 patients (0.1%). Among the most frequent causes of death were cardiac tamponade (25% of deaths), stroke (16%), atrio-esophageal fistula (16%) and massive pneumonia (6%).

Radiofrequency current may cause occlusion of a coronary artery, either by direct thermal damage, spasm, or thrombus formation. Acute coronary artery occlusion is a very rare but potentially life-threatening complication of RFCA. Experience at numerous centers suggests that the risk of coronary occlusion is less than 0.5%. Coronary arterial occlusion could produce myocardial infarction (MI), angina or death. Occlusion of a coronary artery can be treated by restoring coronary blood flow through pharmacological, catheter and/or surgical intervention as medically indicated.

Thrombus generation during the procedure may also pose a serious and even life-threatening risk to the patient. Thrombus may form on the ablation electrode during the application of radiofrequency current with or without any change in impedance. The thrombus might become dislodged and embolize to produce an ischemic stroke, MI, or other occlusive injury. Although some observational studies have shown a relatively lower stroke rate after catheter ablation, whether catheter ablation can reduce the thromboembolic risk remains unclear.

The mean incidence of thromboembolism associated with AF ablation was approximately between 1% and 2%. More recently, incidence of thromboembolism has been reported up to 5% of patients undergoing AF ablation despite perioperative anticoagulation. Ischemic stroke events typically occur within 24 hours of the AF ablation procedure with the higher risk period covering for the first two weeks following ablation.

Pulmonary hemorrhage is a rare but severe complication of PVI. Late hemoptysis and pulmonary hypertension can occur secondary to pulmonary vein stenosis (PVS) after ablation. Acute pulmonary hemorrhage also has been reported. Mechanical trauma from catheter manipulation is a possible mechanism for pulmonary hemorrhage. Injury to a cardiac valve may result from catheter manipulation or the application of radiofrequency current (risk <1%). This may produce valvular insufficiency and possibly require valve replacement surgery.

Figure 9B:
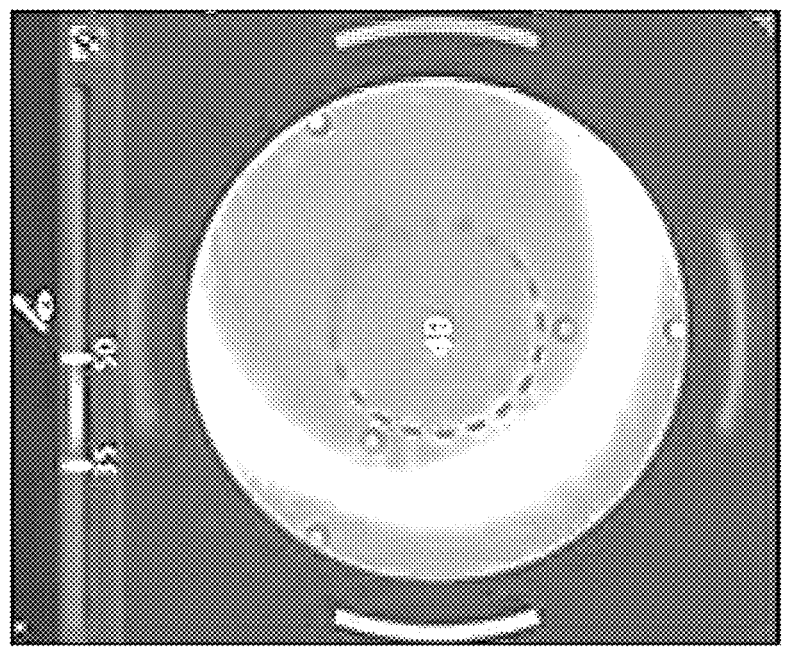
FIG. 9B is an example "bull's eye" display associated with values for each thermocouple reading of the catheter of this disclosure.
Figure 9A:
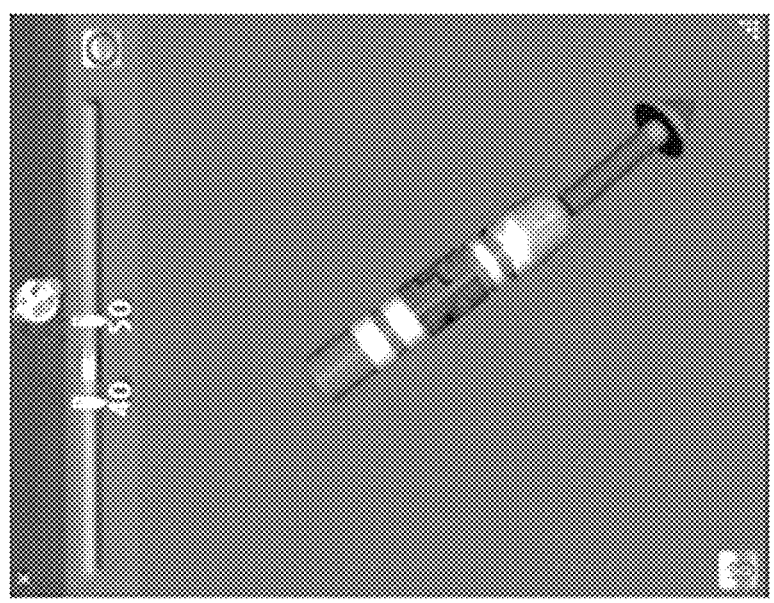
FIG. 9A is an example temperature distribution display associated with the catheter of this disclosure.

FIG. 9A is an example temperature distribution display associated with the catheter 28 of the study in this disclosure. FIG. 9B is an example "bulls eye" display associated with values for each thermocouple reading of the catheter 28 of the study in this disclosure. The "bulls eye" display provides temperature information to the physician. An optional numerical value of the temperature from the RF Generator can be displayed on the "bulls eye" determined by the physician's preference to display or not to display). The graphic of the bull's eye provides relative tip to tissue interface temperature readings obtained from the 6 thermocouples. The graphic provides the physician with an indication as to which part of the catheter tip 13 has contact with the tissue 22.

In addition, the graphic can also provide the physician with an indication of the tip-to-tissue stability. For example, if the catheter tip 13 slips, the temperatures obtained from the thermocouples will change which will be visually displayed on the "bulls eye" as well as on the graphic of the tip 13 of the catheter 28. The colors in the displays can change as the temperature of the thermocouples change. The colors of the graphic of FIG. 9B, though depicted here in black and white, can range from dark blue (minimum temperature) to dark red (maximum temperature) and the circular presentation allows the physician to visualize the relative temperatures of distal and proximal thermocouples in the tip (viewed from the center outward). The outer halo provides the orientation of the catheter tip in 3-dimensional space.

Figure 10:
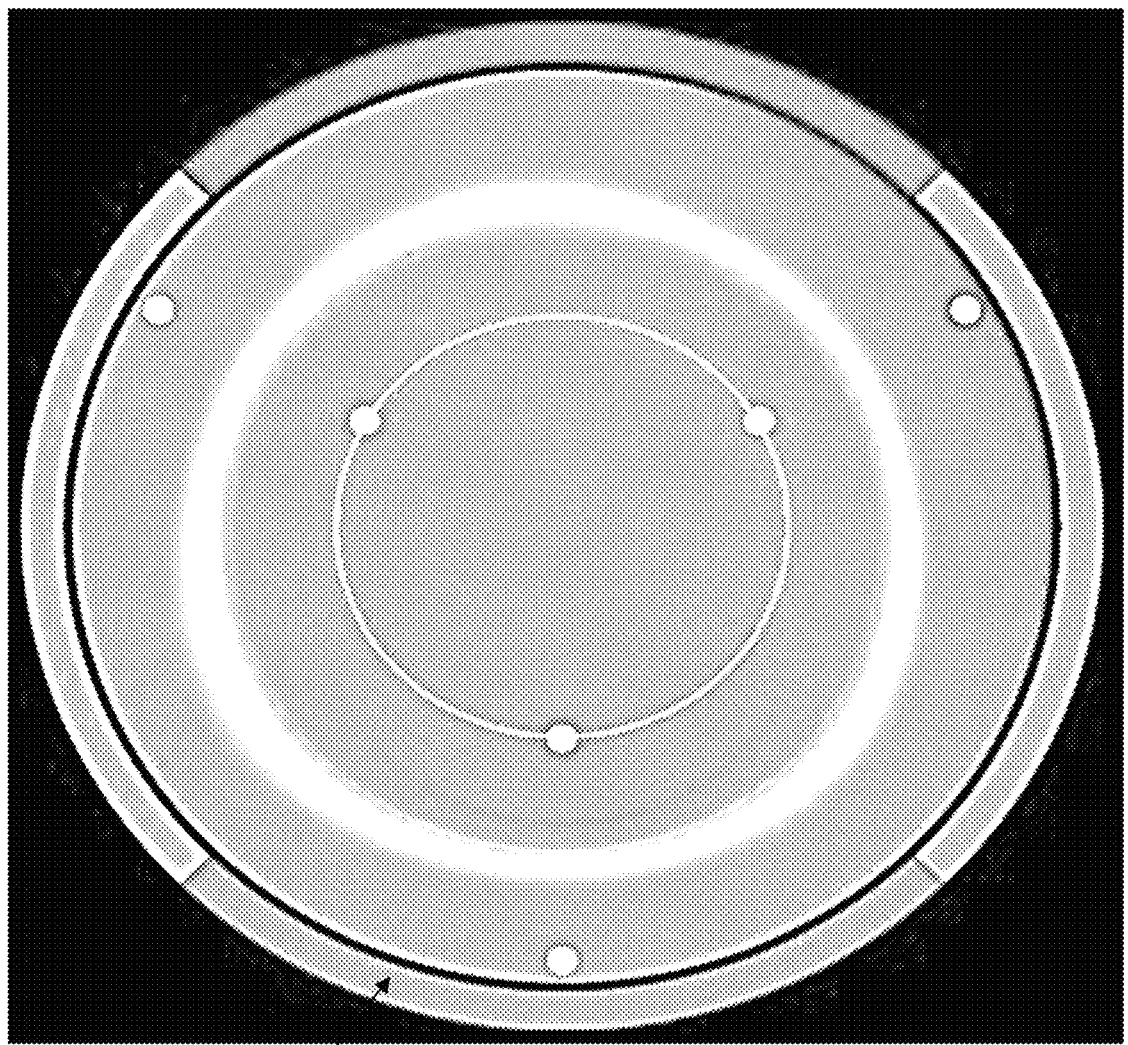
FIG. 10 is a temperature distribution showing the maximum temperature measured by the catheter of the study in this disclosure.

FIG. 10 is a temperature distribution monitoring the maximum temperature measured and used to verify the proper response of the temperature distribution of the catheter tip 13 during the RF ablation session. The temperature feedback display during ablation is shown in FIG. 10 where the six small circles represent the 6 thermocouples (e.g., 3 distal and 3 proximal). The inner circle represents the electrode assembly 19 and the outer ring represents the tip electrode sides. Any change in the desired orientation of tip 13 (e.g., from a perpendicular orientation to the tissue 22), can result in temperature rise of the corresponding part of the electrode assembly 19, as indicated by the darker color in the lower quadrant.

Study Overview

Figure 11:
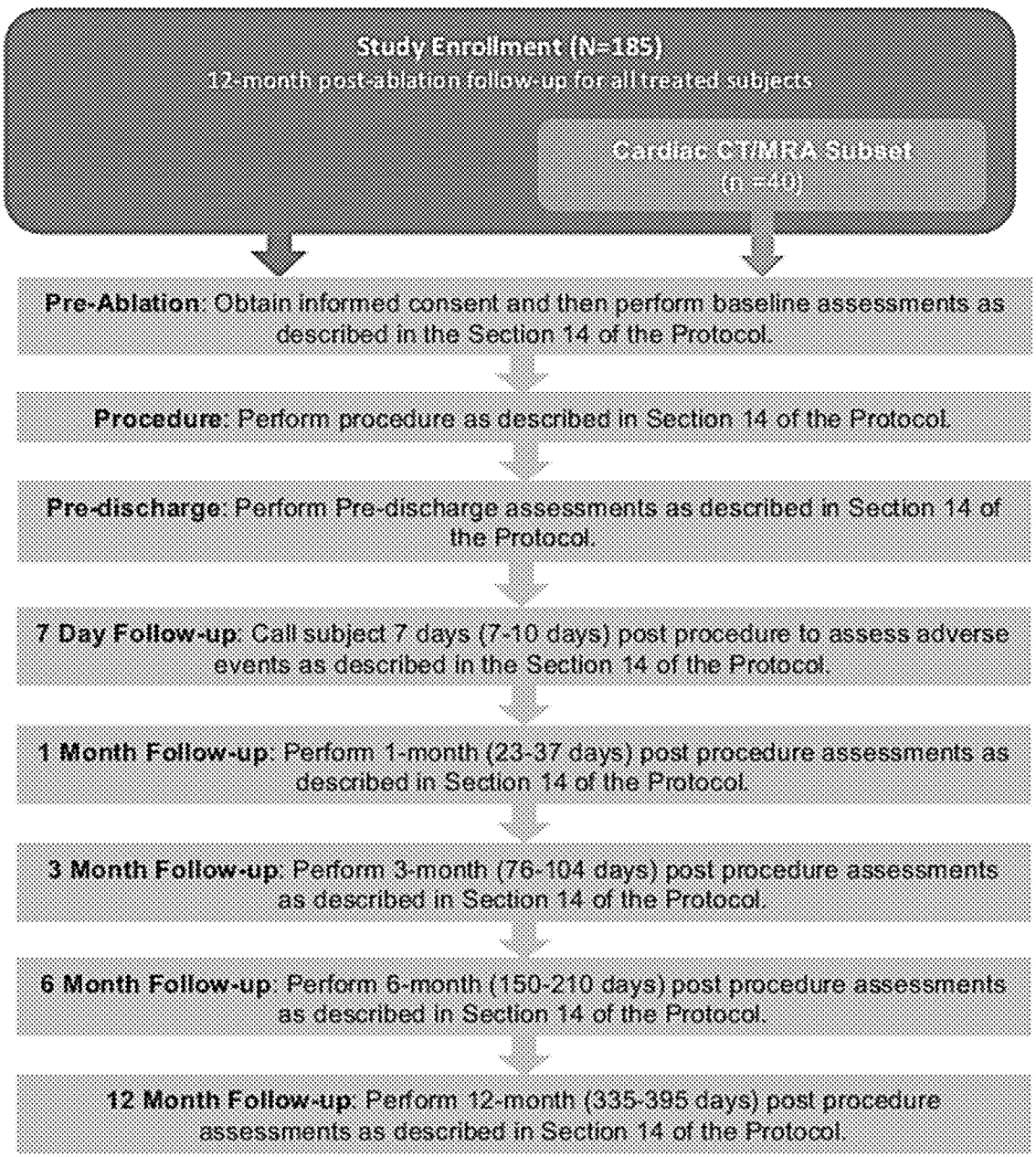
FIG. 11 shows a schematic overview of the study of this disclosure.

This disclosure is more clearly understood with a corresponding study discussed more particularly below with respect to mapping and/or treatment of PAF. FIG. 11 provides a schematic overview of the subject study protocol of this disclosure, which is attached hereto in Appendix 2 and incorporated by reference in its entirety as if set forth verbatim herein. All patients considered for RF ablation procedure for drug refractory recurrent symptomatic PAF were evaluated in the study by the investigator or designated member of the research team for study eligibility per the protocol inclusion and exclusion criteria. Pre-procedure assessments were performed within 30-days prior to the index AF ablation procedure unless otherwise noted.

The primary goal of the study was to demonstrate clinical safety and effectiveness when catheter 28 was used with the RF generator of this disclosure in the treatment of drug refractory symptomatic paroxysmal atrial fibrillation (PAF) during standard electrophysiology mapping and RF ablation procedures. For the trial to be successful, both endpoints must be statistically significant relative to their respective performance goals. The primary safety endpoint was the proportion of subjects with any Primary Adverse Event (PAE) occurring within 7 days of ablation procedure. The PAE rate was compared against a primary goal of 14%. The primary effectiveness endpoint of the study was the proportion of patients that were free from documented atrial arrhythmia (atrial fibrillation (AF), atrial tachycardia (AT), or atrial flutter (AFL)) episodes at Month 12 (that is, during the 9-month post-blanking period, i.e. Day 91-365). Another purpose of this study was to demonstrate the safety based on the proportion of subjects with early-onset (within 7 days of ablation procedure) primary adverse events.

The major secondary objectives of this study were to evaluate the incidence of (serious) adverse events during and after procedure up to 3 months following procedure, to evaluate Acute Procedural Success as defined by the % of subjects with electrical isolation of PVs (entrance block) at the end of the procedure, and the % of subjects with electrical isolation of PVs (entrance block) using QMODE+ as the only ablation strategy. Another secondary effectiveness endpoint was the % of subjects with electrical isolation of PVs (entrance block) at all power settings combined the % of subjects with electrical isolation of PVs (entrance block) after first pass isolation, after waiting period and adenosine challenge. Another secondary effectiveness endpoint was the % of subjects and % of PVs with touch-up (i.e. touch-up is used to remove ablation of acute reconnection) among all targeted veins and touch-up location. Another secondary effectiveness endpoint was the anatomical location of acute PV reconnection after first encirclement. Another purpose of this study was to compare the primary effectiveness of the catheter 28 to a pre-determined performance goal of 50%, which is indicated as the minimum acceptable success rate at 12 months for a paroxysmal AF population.

Secondary safety endpoints of the study included incidence of Unanticipated Adverse Device Effects (UADEs), incidence of Serious Adverse Events (SAEs) within 7 days (early onset), >7 to 30 days (peri-procedural) and >30 days (late onset) of initial ablation, and incidence of bleeding complication (ISTH definitions): a) major, b) clinically relevant non-major and c) minor bleeding. Another purpose of this study was to evaluate the safety and performance of the electrode catheter 28 of this disclosure using a test ablation mode when compared with conventional catheters using power control mode using a well-established canine thigh muscle model.

Catheter 28 was not used in the study under the test ablation mode without irrigation flow and maintaining this higher flow rate. The power control mode, sometimes referred herein as QMODE, was used for PVI once the investigator deems QMODE+ unable to complete PVI. Additionally, QMODE temperature control was used for all RF applications outside the PV ostia during the study ablation procedure. QMODE included either (a) 25-35 W at a flow rate of milliliters/minute or (b) 36-50 W at a flow rate of 15 milliliters/minute. QMODE is a relatively high flow rate starting up to minimal 2 seconds before the onset of RF energy delivery and maintaining this higher flow rate up to 4 seconds after termination of the energy application. In this study, QMODE+ was used as the primary mode for PVI. However, if the investigator deemed QMODE+ unable to achieve PVI, the catheter 28 in QMODE was used to complete the procedure.

The catheter 28 was assessed for clinical safety and performance according to following objectives: (1) Char/coagulum and steam pop rate of catheter 28 using its test ablation mode compared with conventional catheters using power control mode; (2) Lesion dimensions (max depth, max diameter and surface diameter) comparison between catheter 28 and control catheters; and (3) Ablation parameters were collected for analysis for characterization purposes to understand the similarities and differences in their behavior when compared to control catheters: average power, maximum electrode temperature, Temperature Rise, Initial Impedance, Impedance Drop.

An additional purpose of this study was to evaluate the safety and performance of the catheter 28 using a test ablation mode (e.g., nMARQ multichannel RF generator), when simulating a clinical PVI procedure. The overall safety and functional performance of catheter 28 using its test ablation mode was also compared to the Smart Touch SF control catheter (Control Catheter 1) being used in power control mode (i.e. Smart Ablate generator). The catheter 28 was assessed to (1) deliver RF energy at a target site; (2) demonstrate acute isolation of the pulmonary vein; (3) demonstrate clinically acceptable signal quality which was comparable to control; (4) pace from ring electrodes and microelectrodes during idle-state and during ablation; (5) provide significantly better temperature feedback during ablation than control catheter; (6) function effectively when used in conjunction with ancillary equipment (e.g., such as an RF generator, QDOT Dongle, CoolFlow pump and CARTO 3 mapping system).

An additional purpose of this study was to evaluate the safety and performance of the catheter 28 in a test ablation mode (e.g., high power, short duration such as approximately 90 W/4 s) using the RF generator of this disclosure. The overall safety and performance of the catheter 28 in test ablation mode was compared to the safety and performance of Control Catheter 1 in its power control mode at two different settings (50 W/10 s or 30 W/30 s) using an RF generator (e.g., Smart Ablate RF generator), and in particular in use with a canine thigh muscle model. The catheter 28 was assessed for safety and performance a test ablation mode with the following objectives being tested: (1) safety of catheter 28 using test ablation mode (e.g., char/coagulum and steam pop) compared with Control Catheter 1 using its power control mode); (2) lesion dimensions (max depth, max diameter and surface diameter) comparison between test and control catheters; and (3) average power, maximum electrode temperature, temperature rise, initial impedance, and impedance drop.

In the ablation procedure itself, subjects arrived to the electrophysiology laboratory for their ablation procedure and underwent preparation for the procedure per the hospital's standard protocol (discretion of investigator). The ablation procedure utilized the herein described ablation modes (e.g. QMODE and QMODE+ temperature control modes) to treat subjects with PAF. The test ablation mode of QMODE+ for temperature control was used primarily for PVI. The power control mode of QMODE temperature control was used primarily for AF application outside the PV ostia and for touch-up of the PVI. FIG. 12 shows a table summarizing the equipment used in the study.

FIG. 13 shows a table summarizing AADs and impact on primary effectiveness classification for the study of this disclosure. The study investigated Class I drugs (e.g., flecainide, propafenone, disopyramide, etc.) and Class III drugs (e.g., amiodarone, dronedarone, dofetilide, etc. The table of FIG. 13 shows corresponding status of primary effectiveness endpoints based on AAD therapy administered in the blanking and post-blanking periods.

FIG. 14 shows a table summarizing ablation mode and flow rate settings during RF applications. The row with power settings of 90 W corresponds to the test ablation mode. Temperatures displayed on the RF generator during the study did not necessarily represent tissue temperature or electrode tissue interface temperature. The irrigation pump associated with the investigated catheter 28 was configured to deliver a continuous infusion of 2 milliliters/minute of room temperature heparinized saline (1 u heparin/1 millileter saline) when not delivering RF energy. Increase the irrigation to high flow rate starting minimal 2 seconds before the onset of RF energy delivery. When using the catheter 28 in QMODE and QMODE+ in the study, the recommended contact force working range was between 5 and 30 g.

The AF ablation procedures for this study in the test ablation mode followed the following sequence: (1) Diagnostic catheter placement; (2) Electrophysiology study (discretion of investigator); (3) Cardioversion if subject is in AF (discretion of investigator); (4) CARTO® Respiratory Gating Mandatory (unless using Jet Ventilation); (5) Placement of esophageal temperature monitoring device; (6) Confirmation of ACT in ≥350 sec. PRIOR to insertion of the catheter 28 into the left atrium and maintain throughout the procedure; (7) Transseptal puncture; and (8) A left atrial anatomical map is recommended required prior to an ablation procedure in the LA. An anatomical map was not required of triggers outside of the left atrium (e.g. SVC/CS etc.). The sequence could include (9) Introduction of the catheter 28, which could include the following steps: use the AUTOTAG feature in Carto to tag each QMODE+ ablation point after each application; at the new location ensure catheter stability before commencing RF application; a pre-ablation flow rate delay of minimal 2 seconds will occur before RF application; ablation via RF power application of up to 90 W for up to 4 seconds (QMODE+); move the catheter to a new location (~4 millimeter) if clinically effective ablation is achieved; and QMODE+ used for full PV encirclement. If the investigator deemed QMODE+ unable to achieve PVI, the catheter 28 in QMODE was used to complete the procedure. Step (9) could also include continuing RF applications and catheter 28 movement until the circumferential PVI is completed.

If the temperature increased above the temperature cutoff (e.g., 65° C.), RF application was stopped immediately. The decision to interrupt RF power delivery at any time during ablation was guided by investigator judgment and the monitoring of ablation effectiveness parameters, including catheter movement, electrogram reduction and/or impedance changes. For ablation in the region of the right superior PV, precautionary measures such as pacing maneuvers were used to evaluate proximity to the phrenic nerve.

The sequence could also include (10) Left Atrial ablation and real time PV isolation; (11) a 20-minute waiting period post ablation before pacing procedure(s) and/or infusion of cardiac medications to induce AF/reconnection (e.g., Adenosine, Isoproterenol 2-20 microgram/minute); (12) Confirmation of entrance block in all targeted PVs by Lasso® or PentaRay®; and (13) conduct fluoroscopic evaluation of the diaphragm.

It was required in the study to minimize risk of esophageal injury. The method used to localize one of the following: (1) Use of an esophageal temperature probe, (2) Esophageal visualization with CARTOSOUND® and/or ICE, or (3) Esophageal visualization using barium swallow. In the event of Esophageal temperature rise, the following happened: (1) tissue was allowed to cool down, and additional lesion immediately at the same or nearby location; (2) move away from that spot and ablate the other areas first then return to that spot if isolation is not attained; (3) QMODE was optionally used with the operator's usual, chosen, posterior wall power and duration, still watching very carefully for temperature rise and not starting until esophageal temperature returns to baseline; and (4) ablate in an area nearby but slightly away from that area if the above 2 steps don't accomplish the task.

FIG. 15 shows a table summarizing the required schedule for subject treatment and evaluations in the study of this disclosure. In the table, the numbered notes correspond as follows: (1) Initial ablation procedure should be done within 30 days of consent; (2) Collected to confirm no changes in medical history since last visit; (3) AEs collected once consent has been signed Collected to confirm no changes in medical history since last visit; (4) If AE results in Hospitalization health economic data collection was required; (5) Quality of life tools (AFEQT); (6) Pregnancy test must be done on pre-menopausal women only, within 24 hours of the procedure; (7) Subjects should undergo imaging for the presence of LA Thrombus; (8) Imaging TTE to determine the atrial size (if the subject has undergone an imaging procedure within the last 6-months where the atrial size was assessed, the pre-procedure imaging assessment is not required); (9) Post procedure all Subjects will undergo a TTE procedure to assess the pericardium for pericardial effusion and/or pericarditis; (10) Concomitant medications: only cardiac related (anti-arrhythmia drugs, anticoagulation regimen, etc.); (11) PV imaging (CT/MRA) for subjects who have symptoms undergo follow-up for Day 7 and 1 month after the ablation; (12) Health Economic Data for hospitalizations (UB04), ER visits and outpatient visits, if any; (13) TTM: all symptomatic cardiac episodes should be recorded and transmitted at the time the event occurs; (14) 12-month visit or last completed visit; (15) May be virtual visit, or clinic visit; (16) Required only for clinical visit; (17) In the event of a stroke the Modified Rankin Score will assess to evaluate the degree of disability in the subject who suffered the stroke; (18) A standardized neurological assessment (including cranial nerve, motor and sensory function, and gait assessment) is to be done. If this neurological assessment demonstrates new abnormal findings, the patient should also have a formal neurological consult and examination with appropriate imaging (i.e., DW-MRI), used to confirm any suspected diagnosis of stroke; (19) All subjects who undergo a repeat ablation procedure during blanking period with the catheter 28 will suggestive of PV stenosis or are in the CT/MRA PV Analysis procedure.

In the study, an "adverse event" was considered any untoward medical occurrence, unintended disease or injury, or untoward clinical signs (including abnormal laboratory findings) occurring during a clinical study, whether or not related to the study device or ablation procedure. For the purposes of this study, adverse events were deemed as occurring according to the following: event is vascular, cardiovascular, or neurologic in nature; the event is a serious adverse event; causality is related to catheter 28 and its ablation procedure; or unknown in nature.

In contrast, the following clinical events were not considered an adverse event for this clinical study: any medical condition present at the of screening unless study subject's condition deteriorates at any time during the study; a trace/trivial pericardial effusion that is asymptomatic; recurrence of pre-existing AF/AT/AFL; AF/AFL/AT recurrence requiring pharmacological cardioversion at any time throughout the duration of the study, not including new onset of left atrial flutter occurring post-ablation is an AE; re-ablation for AF or pre-existing AFL/AT, however any complication associated with the repeat ablation procedures was considered an AE.

FIGS. 16, 17, 18, and 19 show summarize primary adverse events as determined in the study of this disclosure. As shown therein, a primary AE according to the study was one of the events listed in FIGS. 16-19 that occurred within seven (7) days following an AF ablation procedure with the catheter 28 when used with the RF generator described herein, except atrio-esophageal fistula and PV stenosis, which may also be considered as primary adverse events if occurring greater than seven (7) days and up to 90 days post the ablation procedure.

A serious adverse event (SAE) in the study was considered any event that meets one or more of the following criteria: Lead to a death; Lead to a serious deterioration in the health of a subject that resulted in a life-threatening illness or injury or a permanent impairment of a body structure or a body function; Required in-patient hospitalization or prolongation of existing hospitalization; or Resulted in medical or surgical intervention to prevent permanent impairment to body structure or a body function; Lead to fetal distress, fetal death or a congenital abnormality or birth defect.

FIG. 20 is a table summarizing intensity or severity according to the study of this disclosure, whereby intensity or severity of AEs is defined. Intermittent AEs were classified according to their greatest severity. A continuous AE that changes severity was reported as a new AE.

In the power control mode, workflow functioned as follows. If the temperature increases rapidly, RF application was stopped immediately. RF power range of 15-50 Watts (W) was used for atrial ablation. At anatomical locations, not on the LA posterior wall or CS, maximum allowed power did not exceed 50 W and duration of ablation did not exceed 60 seconds of continuous ablation at a given location. The catheter 28 was moved or dragged to a new location when clinically effective ablation was achieved (e.g., electrogram reduction and/or impedance drop).

While ablating on the posterior wall and coronary sinus, the following precautions were taken. Regarding LA posterior wall and close to the esophagus, ablation was started using standard workflow for posterior wall. The catheter 28 was moved or dragged to a new location if clinically effective ablation is achieved within 20 seconds (electrogram reduction and/or impedance drop). Maximum power used to ablate the posterior wall and coronary sinus did not exceed 35 W, except when using the test ablation mode. Esophageal temperature changes were monitored by an endo-luminal esophageal probe or method used to move esophagus. Duration of ablation did not exceed 30 seconds on posterior wall.

Procedural data collection was done through anonymized (or de-identified) generator files, anonymized (or de-identified) CARTO® data files, procedural worksheets and subject medical files. Documentation of procedural data was kept in the subject's CRF, anonymized (or de-identified) back-up generator files and back-up CARTO® data files for study analysis. The information collected during the procedure included, but was not limited to, following: RF application-mode per lesion (QMODE+/QMODE/other); Number of RF applications with Catheter 28 (total/QMODE+/QMODE) and with non-study catheter; Duration of RF applications with Catheter 28 (total/QMODE+/QMODE) and with non-study catheter; PVI ablation time (time between first RF application and last RF application on a PV before isolation confirmed and circumferential ablation achieved); Subject PVI ablation time (time between first RF application and last RF application before all PVI complete); Subject total ablation time (time between first RF application and last RF application in a subject); Ablation parameters per RF application: location, temperature, impedance, power, contact force, RF duration, ablation index, lesion information on CARTO®; Ablation number on the generator for first RF application and last RF application per target (left PV targets, right PV targets and for targets outside the PV area); Ablation parameters for touch-up applications (location, RF application-mode, amount of touch-up applications, duration and associated generator file number); Total procedure time (from first femoral puncture to last catheter removal); Atrial mapping time; Fluoroscopy time and dose; LA catheter dwell time (from ablation catheter LA insertion to ablation catheter removal from the LA); ECG data; Total fluid delivered via ablation catheter and via intravenous line; fluid output and net fluid input; Strategy used to minimize risk of esophageal injury; and Abnormal esophageal temperature rises.

Subjects of the study were required to complete follow up visits through 12 months (365 days) post initial ablation procedure. Follow-up schedules were based on a 30-day month. Follow-up visits were scheduled according to the following timeframes: 7 day (7D, day 7-10), 1 month±7 days (1M, day 23-37), 3 month±14 days (3M, day 76-104), 6 months±30 days (6M, day 150-210), and 12 month±30 days (12M, day 335-395). Follow-up visit schedule did not reset if subject underwent a repeat AF ablation procedure.

Prior to hospital discharge, physical exam included standardized neurological assessment (including cranial nerve, motor and sensory function, and gait assessment) be performed pre-discharge. If neurological assessment demonstrated new abnormal findings as compared to the one performed at baseline, a formal neurological consult and examination with appropriate imaging (e.g., DW-MRI), was done to confirm any suspected diagnosis of stroke. NIH Stroke Scale (NIHSS) was administered by certified healthcare provider done prior to discharge. Other events prior to discharge included detecting occurrence of arrhythmias, a electrocardiogram (12-Lead ECG), and transthoracic echocardiogram (TTE), for evaluation pericardium for possible pericardial effusion and/or pericarditis. In the event significant pericardial effusion was identified, subjects were followed until the condition resolves. Cardiac-related concomitant medications (such as AADs, anticoagulation regimen, etc.) prescribed since the ablation procedure till the end of follow-up were recorded, including the type and name of the medication, associated indications, starting and ending dates of the prescriptions, etc.

Patient Selection

The criteria for patient selection, methods, personnel, facilities, and training specified in this study were intended to minimize the risk to subjects undergoing this procedure. Subjects were prescreened carefully prior to enrollment in the study to ensure compliance with the inclusion and exclusion criteria.

Inclusion criteria for the study included the following:
Symptomatic paroxysmal AF with one electrocardiographically documented AF episode
within 6 months prior to enrollment and a physician's note indicating recurrent self-terminating AF within 7 days. Documentation may include electrocardiogram (ECG); Transtelephonic monitoring (TTM), Holter monitor or telemetry strip.
Failed at least one (1) antiarrhythmic drug (AAD) (class I or III) as evidenced by recurrent symptomatic AF, contraindicated, or intolerable to the AAD.
Age 18 years or older.
Signed Patient Informed Consent Form (ICF).
Able and willing to comply with all pre-, post-, and follow-up testing and requirements.
Exclusion criteria for the study included the following:
Previous surgical or catheter ablation for atrial fibrillation.
AF secondary to electrolyte imbalance, thyroid disease, or reversible or non-cardiac cause.
Patient on amiodarone at any time during the past 3 months prior to enrollment.
Previously diagnosed with persistent or long-standing persistent AF and/or Continuous AF lasting >7 days
CABG surgery within the past 6 months (180 days).
Valvular cardiac surgical/percutaneous procedure (i.e., ventriculotomy, atriotomy, valve repair or replacement and presence of a prosthetic valve).
Any carotid stenting or endarterectomy within the last 6 months.
Documented LA thrombus on imaging (within 48 hr prior of a study ablation procedure).
Documented LA size >50 mm (parasternal long axis view).
Documented LVEF <40%.
Contraindication to anticoagulation (e.g. heparin)
History of blood clotting or bleeding abnormalities
MI/PCI within the past 2 months (60 days)
Documented thromboembolic event (including TIA) within the past 12 months (365 days)
Rheumatic Heart Disease
Uncontrolled heart failure or NYHA function class III or IV
Severe mitral regurgitation (Regurgitant volume greater than or equal to 60 mL/beat, Regurgitant fraction greater than or equal to 50%, and/or Effective regurgitant orifice area greater than or equal to 0.40 cm$^2$)
Awaiting cardiac transplantation or other major cardiac surgery within the next 12 months (365 days)
Unstable angina
Active systemic infection or sepsis
Diagnosed atrial myxoma or presence of an interatrial baffle or patch.
Presence of implanted ICD/CRT-D.
Significant pulmonary disease, (e.g., restrictive pulmonary disease, constrictive or chronic obstructive pulmonary disease) or any other disease or malfunction of the lungs or respiratory system that produces chronic symptoms.
Severe Gastroesophageal Reflux Disease (GERD; active requiring significant intervention not including OTC medication)
Significant congenital anomaly or medical problem that in the opinion of the investigator would preclude enrollment in this study.
Women who are pregnant (as evidenced by pregnancy test if pre-menopausal), lactating, or who are of child bearing age and plan on becoming pregnant during the course of the study.
Enrollment in an investigational study evaluating another device, biologic, or drug.
Presence of intramural thrombus, tumor or other abnormality that precludes vascular access, or manipulation of the catheter.
Presence of an inferior vena cava filter.
Presenting contra-indication for the devices (e.g. TTE, CT, etc.) used in the study, as indicated in the respective instructions for use.
Life expectancy less than 12 months Results of the Study In the study, catheter 28 was evaluated and compared to a historical control performance goal with 185 evaluable subjects. FIG. 21 is a table summarizing AE outcomes as assessed in the study of this disclosure. FIG. 22 is a graph summarizing patient characteristics and medical history in the study of this disclosure. FIG. 23 is a graph summarizing acute pulmonary vein reconnection in the study of this disclosure. FIG. 24 is a graph summarizing primary adverse events in the safety population of the study of this disclosure.

First and significantly, in a preclinical study, it was shown that ablation with catheter 28 resulted in 80% less RF time compared to conventional ablation. With that, in the study of this disclosure, a total of 52 patients underwent ablation and completed follow-up. PVI was achieved in all patients using the catheter 28 alone, with total procedure and fluoroscopy times of 105.2±24.7 and 6.6±8.2 minutes, respectively. Most patients (n=49; 94.2%) were in sinus rhythm at 3 months. Two PAEs were reported: one pseudoaneurysm and one asymptomatic thromboembolism. There were no deaths, stroke, atrioesophageal fistula, PV stenosis, or unanticipated adverse device effects. Six patients had identified SCLs—all classified as asymptomatic without clinical or neurologic deficits. Consistent with most PAF populations, the age of enrolled patients was relatively young (62.0±12.0 years), approximately two-thirds were men, the overall rate of comorbidities was moderate (63.0% hypertension; 18.5% congestive heart failure), and the anteroposterior left atrial diameter was moderately enlarged (39.3±5.2 mm). Of the 52 participants who underwent ablation, PVI was performed in all; only one patient received additional ablation—roof line and a line between the left and right inferior PVs. None required a second ablation for PAF during the follow-up interval. The total number of radiofrequency applications was 108.3±42.5, with CF 16.9±6.7 grams (minimum 8.1 grams and maximum 36 g) and power 85.4±6.7 W.

Figure 25:
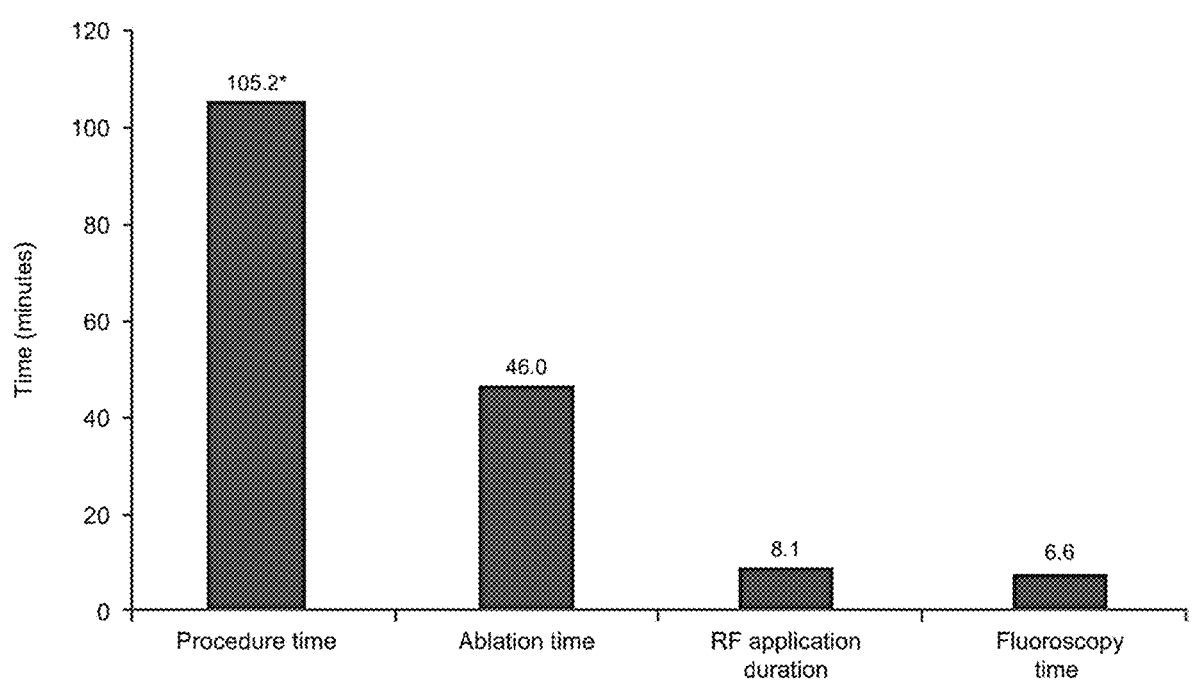
FIG. 25 is a graph summarizing procedural parameters in the study of this disclosure.

FIG. 25 is a graph summarizing procedural parameters in the study of this disclosure. As shown, the total procedure time, which was understood as the time of first puncture until the time of last catheter removed, including a 20-minute waiting time and the adenosine or isoproterenol challenge, was 105.2±24.7 minutes (range 68.0-177.0 minutes). Of this total procedure time, the mapping time was 9.5±5.3 minutes, fluoroscopy time was 6.6±8.24 minutes, total PV ablation time was 44.3±22.4 minutes, total ablation time (from the time of the first radiofrequency application to the time of the last radiofrequency application) was 46.0±21.3 minutes, and left atrial dwell time (time from catheter insertion in the left atrium until removal from the left atrium) was 81.7±20.2 minutes. For the 50 patients for whom data were collected, the volume of fluid delivered by the ablation catheter was 382.4±299.1 mL.

Figure 26:
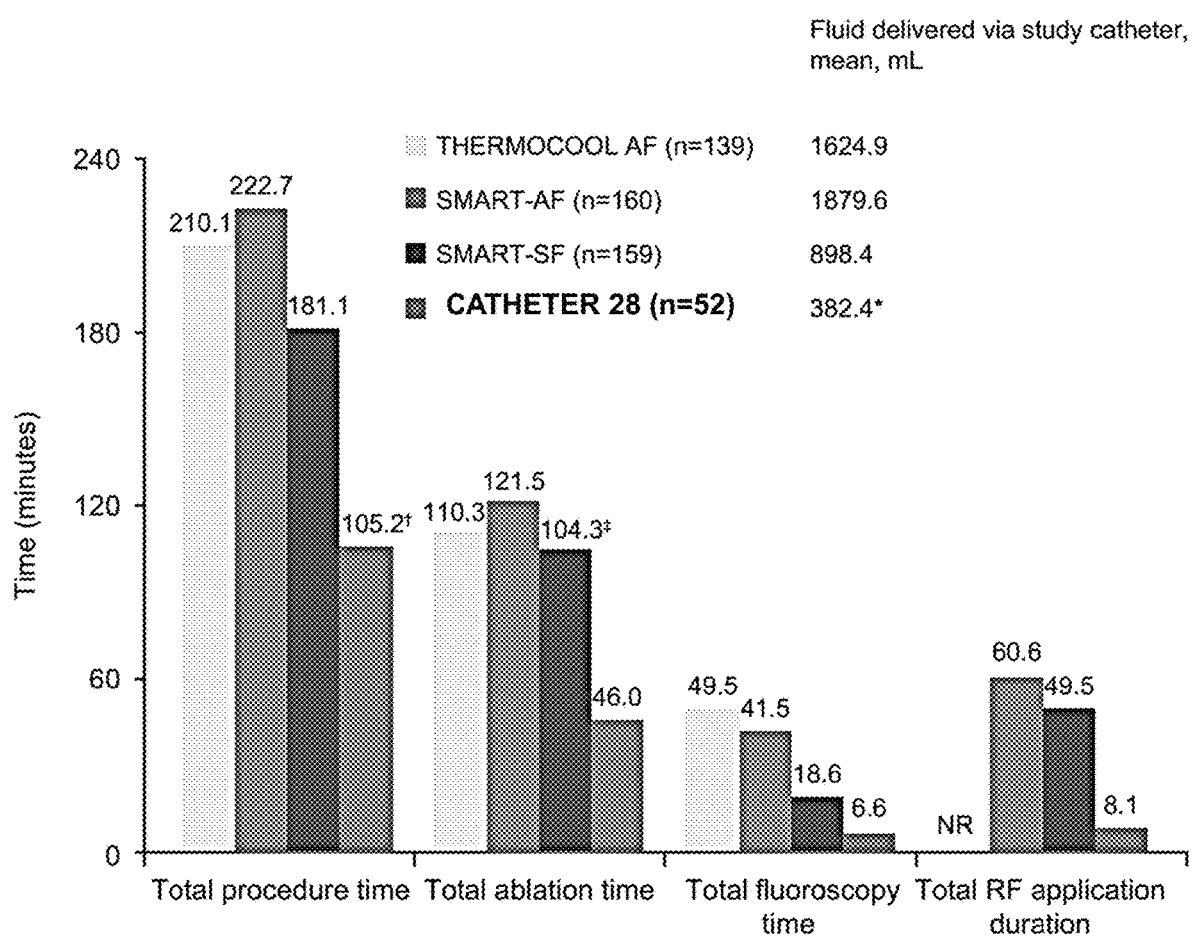
FIG. 26 is a graph summarizing procedural outcomes in the study of this disclosure.

FIG. 26 is a graph summarizing procedural outcomes in the study of this disclosure. As can be seen, the procedural outcomes of catheter 28 as evaluated in the study are substantially improved over other previous multicenter studies. Key procedural parameters are shown for both the study, as well as previous multicenter studies: the THERMOCOOL AF trial which investigated a saline-irrigated radiofrequency ablation catheter, the SMART-AF trial which investigated a saline-irrigated force-sensing ablation catheter, and the SMART-SF trial which investigated a force-sensing ablation catheter with enhanced saline irrigation.

FIGS. 27A-27B are tables summarizing comparative procedural outcomes between the catheter of this disclosure and prior clinically approved devices. Regarding fluid delivered by an ablation catheter during the procedure of the study, the catheter 28 of this disclosure registered a total mean fluid delivered as 382.4 mL, which was approximately a 57.4% improvement (i.e. ~898.4 mL) over Smart Touch SF, approximately a 79.7% improvement (i.e. ~1879.6 mL) over Smart Touch AF, and approximately a 57.4% improvement (i.e. ~898.4 mL) over THERMOCOOL. Regarding total procedure time by an ablation catheter during the procedure of the study, the catheter 28 of this disclosure registered a mean total procedure time of approximately 105.2 minutes, which was approximately a 41.9% improvement (i.e. ~181.1 minutes) over Smart Touch SF, approximately a 52.8% improvement (i.e. ~222.7 minutes) over Smart Touch AF, and approximately a 49.9% improvement (i.e. ~210.1 minutes) over THERMOCOOL.

Regarding total ablation time by an ablation catheter during the procedure of the study, the catheter 28 of this disclosure registered a mean total ablation time of approximately 46 minutes, which was approximately a 55.9% improvement (i.e. ~104.3 minutes) over Smart Touch SF, approximately a 62.1% improvement (i.e. ~121.5 minutes) over Smart Touch AF, and approximately a 58.3% improvement (i.e. ~110.3 minutes) over THERMOCOOL. Regarding total fluoroscopy time during the procedure of the study, the catheter 28 of this disclosure registered a mean total fluoroscopy time of approximately 6.6 minutes, which was approximately a 64.5% improvement (i.e. ~18.6 minutes) over Smart Touch SF, approximately a 84.1% improvement (i.e. ~41.5 minutes) over Smart Touch AF, and approximately a 86.7% improvement (i.e. ~49.7 minutes) over THERMOCOOL. Regarding total RF ablation time during the procedure of the study, the catheter 28 of this disclosure registered a mean total RF ablation time of approximately 8.1 minutes, which was approximately a 83.6% improvement (i.e. ~49.5 minutes) over Smart Touch SF, approximately a 86.6% improvement (i.e. ~60.6 minutes) over Smart Touch AF. No prior known numbers were known regarding total RF ablation time for THERMOCOOL. Compared with previous studies using CF and non-CF catheters, catheter 28 clearly demonstrated substantially shorter total procedure, ablation, fluoroscopy, and radiofrequency application times, and less irrigation fluid load.

FIG. 28 is a table summarizing results for ablations by setting on all locations of the study. FIG. 29 is a table summarizing results for ablations by setting on all locations of the study. In particular, the tables shows information related to first pass isolation versus acute reconnection in the test ablation mode with catheter 28 during the procedure of the study.

The primary effectiveness endpoint (PVI confirmed after adenosine or isoproterenol challenge) was achieved using catheter 28 in all patients. Of note, in 78.8% (41/52) of cases, PVI was achieved using the test ablation mode only. In 26.9% (14/52) of patients and 5.0% (22/444) of veins, PV reconnection after adenosine/isoproterenol prompted additional lesions, the majority posteriorly. The original lesions were created with a combination of test ablation and standard ablation in 5 veins and with test ablation only in the other 17 veins showing acute reconnection. There were no applications placed with a non-study catheter. At the 3-month follow-up visit, 49 patients (94.2%) were in sinus rhythm, while two patients were in AF and one was in atrial flutter.

Two PAEs (2/52, 3.8%) were reported: one femoral pseudoaneurysm (also classified as an SADE and successfully treated by thrombin injection) and one asymptomatic thromboembolism (2 new micro emboli; present in MRIs at discharge and reconfirmed at 1 and 5 months post-procedure). There were no deaths, stroke, atrioesophageal fistula, PV stenosis, or unanticipated adverse device effects. An additional SADE (esophageal ulcer hemorrhage) was observed via post-procedural endoscopy at Day 1, which healed with medication.

Of 51 patients who had an MRI post-ablation, SCLs were found in six patients (6/51, 11.7%)). Four of these patients were on uninterrupted anticoagulation for at least 3 weeks before ablation, one patient was on warfarin that was interrupted the day before the procedure, and one was not using anticoagulation therapy. All lesions were classified as asymptomatic cerebral emboli, given the absence of clinical or neurologic deficits (as assessed by NIHSS, mRS, and MoCA). In the five patients with one new micro embolus, lesions were resolved by 1 month. While the reported incidence in previous studies of post-ablation cerebral lesions varies widely, these lesions are typically not associated with neurologic deficits, and most disappear on repeat MRI after 1 to 3 months post-ablation.

Acute procedural success (defined as confirmation of entrance block in all treated PVs) was achieved in all 52 patients who underwent ablation. Only two PAEs were reported (a pseudoaneurysm and an asymptomatic thromboembolism); there were no reported deaths or instances of atrioesophageal fistula, stroke/cardiovascular accident, transient ischemic attack, PV stenosis, phrenic nerve paralysis, or cardiac tamponade.

The ability to safely ablate with very high power and short duration has some theoretical advantages. First, it appears that catheter-tissue contact stability is an important factor contributing to clinical success. Sufficient minimum CF is needed to enable contact to provide long-term freedom from recurrent arrhythmia, while higher than necessary CF may cause immediate complications such as thrombus from steam pops or atrial perforation. During test ablation, the negative effects of CF instability may be mitigated because lesion creation is achieved in a very short duration of time, before stability becomes a consideration. Indeed, in pre-clinical studies, the quality of the lesions appears more homogeneous than with standard ablation. Of course, greater degrees of instability may attenuate or frustrate the efficacy of even test ablation mode with catheter 28 lesions.

Second, a crucial safety consideration for AF ablation is minimizing damage to collateral tissues. It has been suggested in preclinical models that test ablation minimizes conductive heating and subsequent damage to collateral tissues, such as the esophagus, potentially minimizing the risk of atrioesophageal fistula. The absence of atrioesophageal fistula in our study was encouraging. Indeed, the single case of esophageal ulcer hemorrhage observed in our study is a reminder that one must remain vigilant to ensure that complication rates do not escalate with the test ablation mode strategy.

The overall incidence of coagulum observed with the catheter 28 in test ablation mode was shown to be clinically similar Control Catheter 1 and significantly less compared to Control Catheter 2. The overall incidence of steam pops observed with the catheter 28 in test ablation mode was clinically similar compared to Control Catheters 1 and 2. The lesion characteristics were clinically similar between the catheter 28 and the control catheters. The overall performance of catheter 28, in the test ablation mode was clinically similar or better compared to the Control Catheters 1 and 2 in power control ablation mode.

The overall safety and performance, including endpoints such as coagulum and steam pops, of the catheter 28, when used in the test ablation mode, was shown to be clinically similar compared to the Control Catheters 1 and 2 when used in power control mode. The maximum ablation parameters identified for catheter 28, in the test ablation mode have been tested and assessed to be both clinically safe and clinically effective based on the results of this study.

No char/coagulum observed on catheter 28. The overall incidence of steam pop observed with catheter 28 (0 in RA, 5/9 in the LV and 0 in all other locations) was lower compared to the Control Catheter 1 (0 in RA, 3/36 during PVI, 5/12 in LA wall, 5/6 in LV and 1/7 in RV). Significantly, there were zero incidence of steam pop occurrence in both left and right atrial ablations using catheter 28 with test ablation mode at the study settings.

In the study, the catheter 28 when used with its test ablation mode, was able to produce clinically effective electrogram signal attenuation and clinically equivalent to or better lesions as compared to the Control Catheter 1 in all four cardiac chambers. The generator used in connection with the catheter 28 was also shown to be able to successfully modify the irrigation flow rate based on catheter 28 electrode temperature response and power settings to maintain temperature limit when used in the test ablation mode. The catheter 28 with test ablation mode using the temperature target and flow rate settings was shown to satisfy all acceptance criteria. The overall functionality and the clinical safety of the catheter 28 with test ablation mode proved to be clinically equivalent to or better than that of Control Catheter 1.

In the study, there was no significant difference in the overall incidence of coagulum observed with catheter 28 using test ablation mode compared with Control Catheter 1 in power control mode, when tested in both perpendicular and parallel orientations. In conclusion, this study of catheter 28 demonstrated its clinical feasibility and associated safety.

Figure 30A:
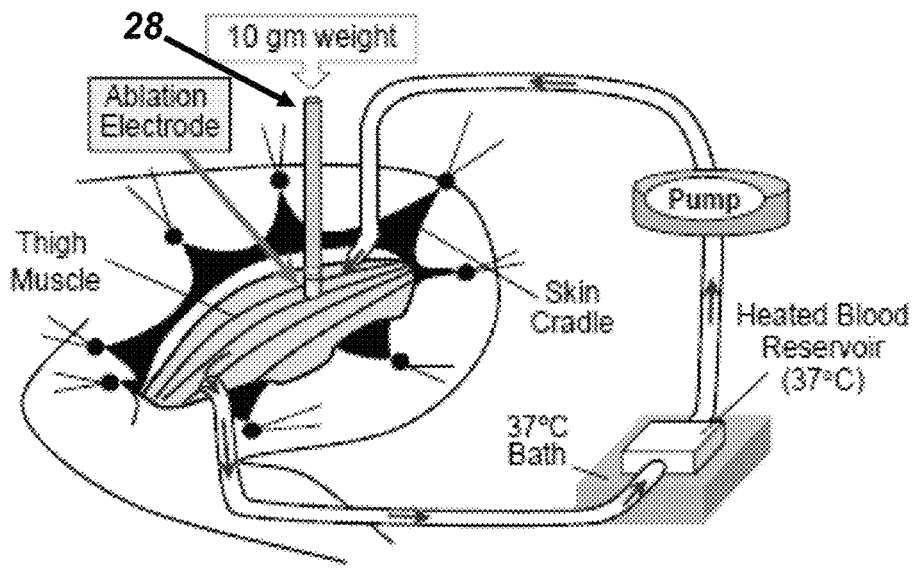
FIG. 30A is an example schematic for a second study of this disclosure.
Figure 30B:
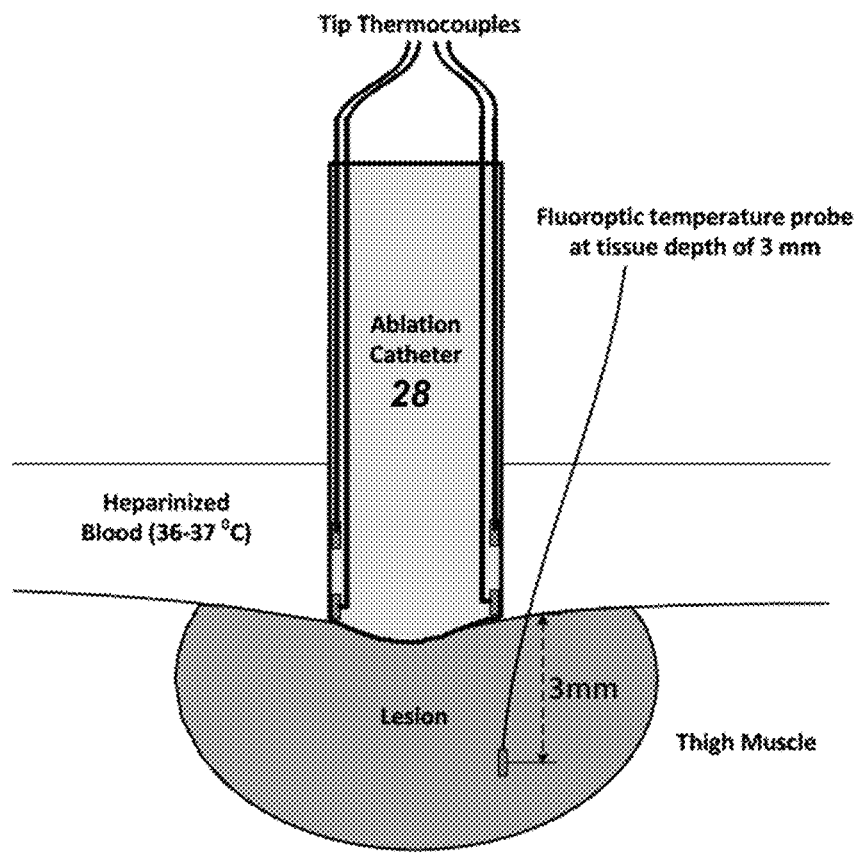
FIG. 30B is an example schematic for a second study of this disclosure.

In a second study, catheter 28 of this disclosure was evaluated with temperature-controlled 90 W-4 second ablation mode that was applied at the thigh muscle and beating heart models in six (6) canines with an average weight of about 21.9 kilogram, as shown in FIG. 30A. In this study, an optical temperature sensor was placed into the thigh muscle of each patient at about a 3 mm deep under the catheter tip to compare tissue temperature trend and heating pattern at single and double ablations as shown in FIG. 30B. The lesion depth was measured according to RF applications. A RA linear lesion integrity and any gaps between lesions were tested and examined in canine beating hearts using different sizes of lesion tag.

Figure 31A:
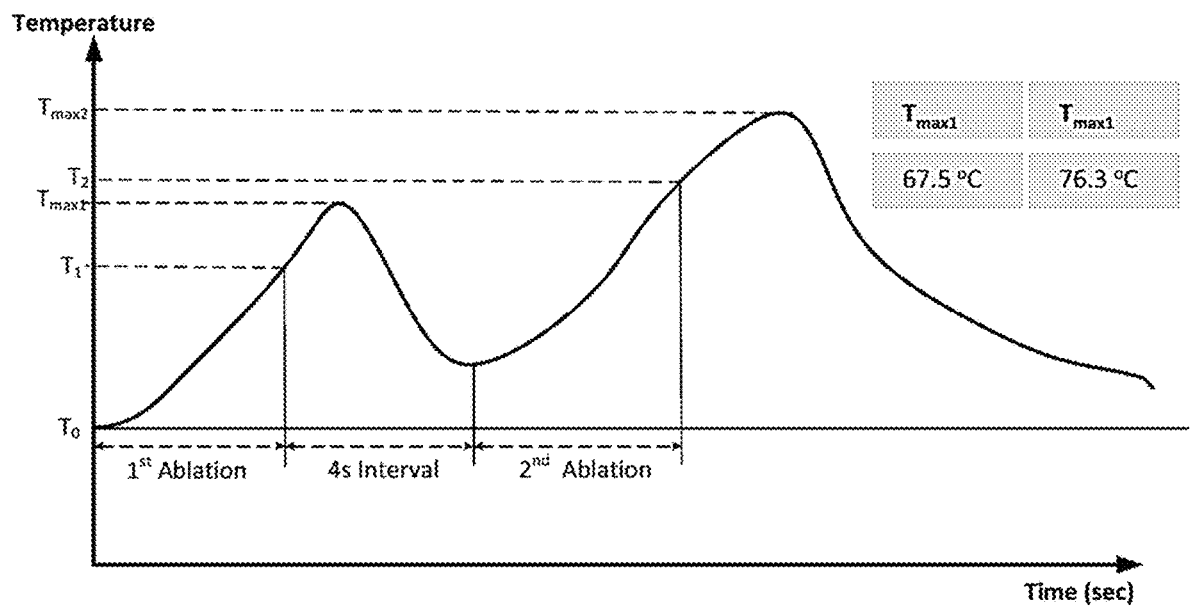
FIG. 31A summarizes certain results for a second study of this disclosure.
Figure 31B:
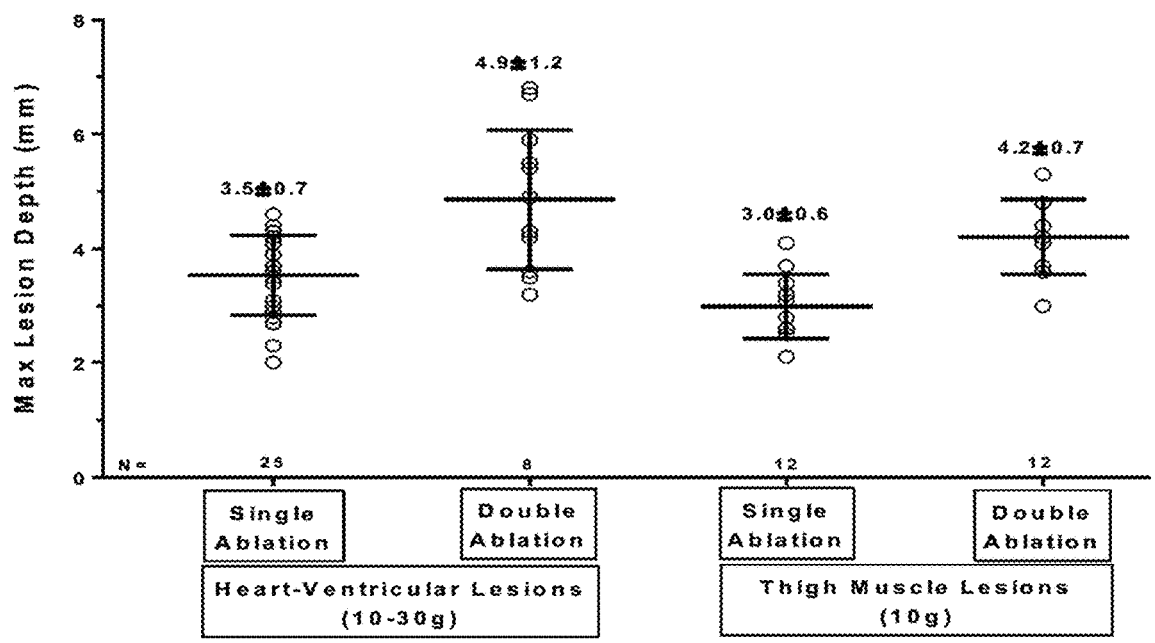
FIG. 31B summarizes certain results for a second study of this disclosure.

In the second study, it was observed that double 90 W-4 S applications with 4 S break period of time caused further tissue temperature rise, including from 67.5° C. to 76.3° C. as seen in FIG. 31A. The second study also resulted in 40% deeper lesion in both the beating hearts and thigh muscles as seen in FIG. 31B with no char, coagulum or steam pop observed. Gross pathology also showed that when using a 2 mm RF tag, an overlapped continuous RF lesion line was created. There were gaps detected in the lesion line using a 4 mm RF tag and likewise a continuous lesion line was created with minimal overlapping lesions using 3 mm tag. In the second study, it was therefore concluded that when using 3 mm lesion tag and point-by-point "kissing" ablation approach, 90 W-4 S created a continuous and transmural linear lesion line at the atrial wall with minimal over-lapped lesions. Consecutively overlapped 90 W-4 S applications applied intentionally created deeper lesions.

Figure 32:
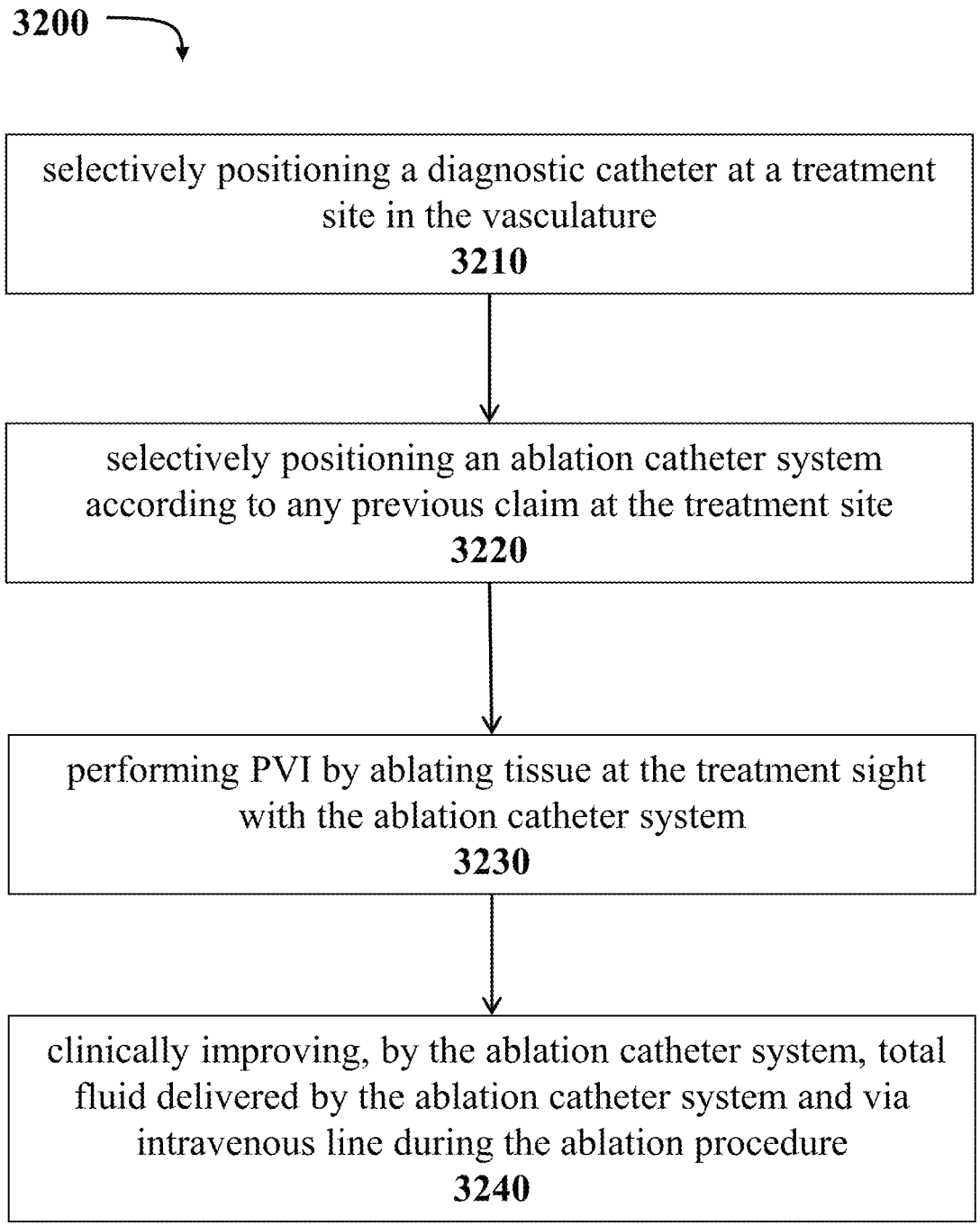
FIG. 32 depicts a graphical overview of one method or use according to this disclosure.

FIG. 32 depicts a graphical overview of one method 3200 according to this disclosure. The method 3200 can include 3210 selectively positioning a diagnostic catheter at a treatment site in the vasculature; 3220 selectively positioning an ablation catheter system according to any previous claim at the treatment site; 3230 performing PVI by ablating tissue at the treatment site with the ablation catheter system; and 3240 clinically improving, by the ablation catheter system, total fluid delivered by the ablation catheter system and via intravenous line during the ablation procedure.

FIG. 33 depicts a graphical overview of one method 3300 according to this disclosure. The method 3300 can include 3310 inserting an ablation catheter system according to any preceding claim to a treatment site comprising cardiac tissue, the system comprising at least one electrode and at least one sensor into the body in proximity; 3320 ablating the cardiac tissue with the ablation catheter system; and 3330 achieving complete pulmonary vein isolation, by the ablation catheter system, for all patients of a predetermined patient population suffering from PAF.

FIG. 34 depicts a graphical overview of one method 3400 according to this disclosure. The method 3400 can include 3410 inserting an ablation catheter system according to any preceding claim into a body of a living subject; 3420 urging the ablation catheter system into contact with a cardiac tissue in the body; 3430 generating ablative energy at a power output level at a level of current; 3440 transmitting the generated energy into the tissue via the ablation catheter system; 3450 ablating the cardiac tissue with the ablation catheter system; and 3460 clinically improving, by the ablation catheter system, safety and effectiveness resulting in approximately at least 80% less RF ablation time compared to ablation time of a previous clinically approved catheter system for PAF.

Figure 35:
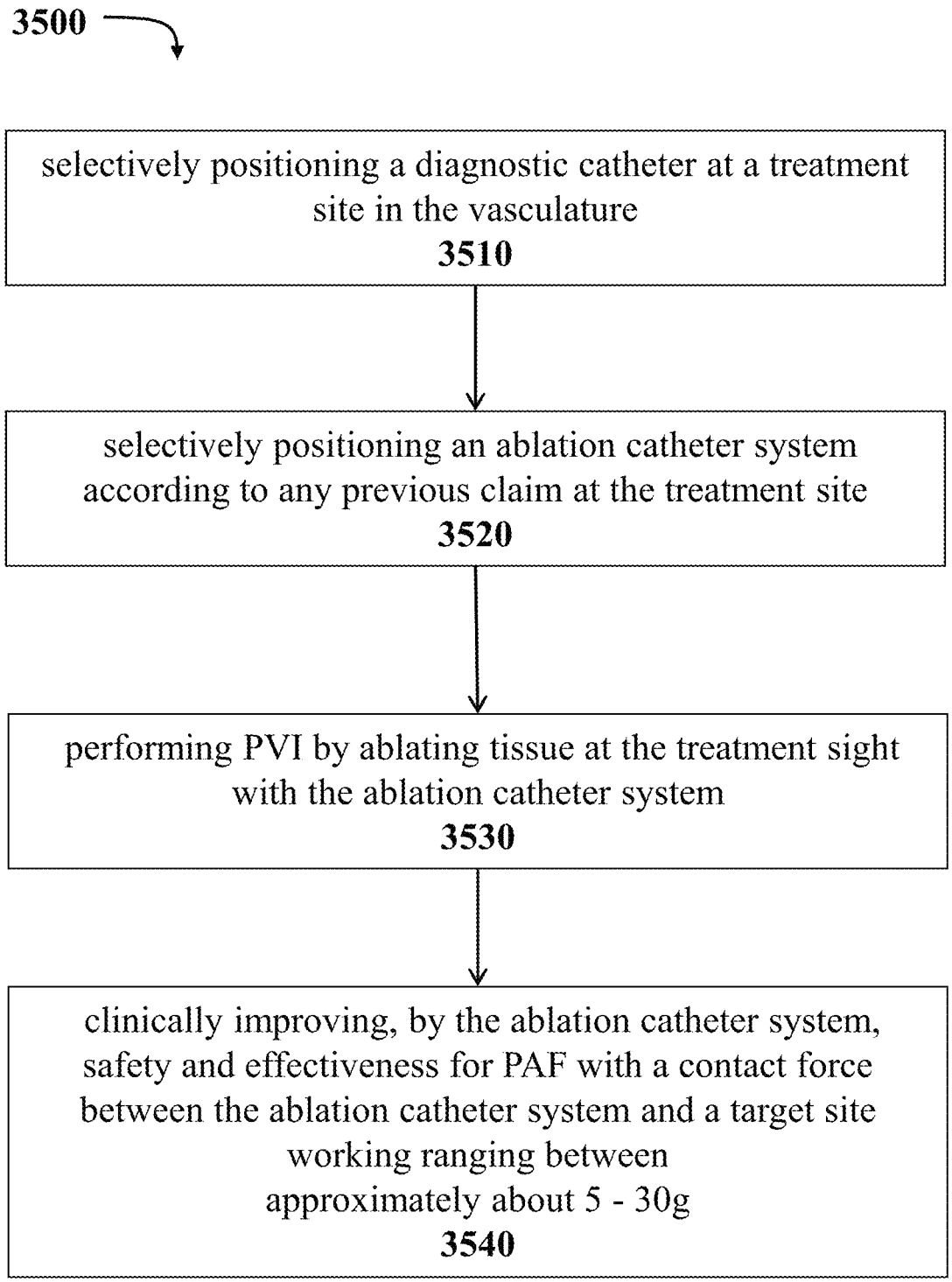
FIG. 35 depicts a graphical overview of one method or use according to this disclosure.

FIG. 35 depicts a graphical overview of one method 3500 according to this disclosure. The method 3500 can include 3510 selectively positioning a diagnostic catheter at a treatment site in the vasculature; 3520 selectively positioning an ablation catheter system according to any previous claim at the treatment site; 3530 performing PVI by ablating tissue at the treatment site with the ablation catheter system; and 3540 clinically improving, by the ablation catheter system, safety and effectiveness for PAF with a contact force between the ablation catheter system and a target site working ranging between approximately 5-30 grams.

FIG. 36 depicts a graphical overview of one method 3600 according to this disclosure. The method 3600 can include 3610 inserting an ablation catheter system according to any preceding claim to a treatment site comprising cardiac tissue, the system comprising at least one electrode and at least one sensor into the body in proximity; 3620 ablating the cardiac tissue with the ablation catheter system; and 3630 achieving clinically improved safety and effectiveness for PAF with substantially shorter total procedure, ablation, fluoroscopy, and radiofrequency application times.

Figure 37:
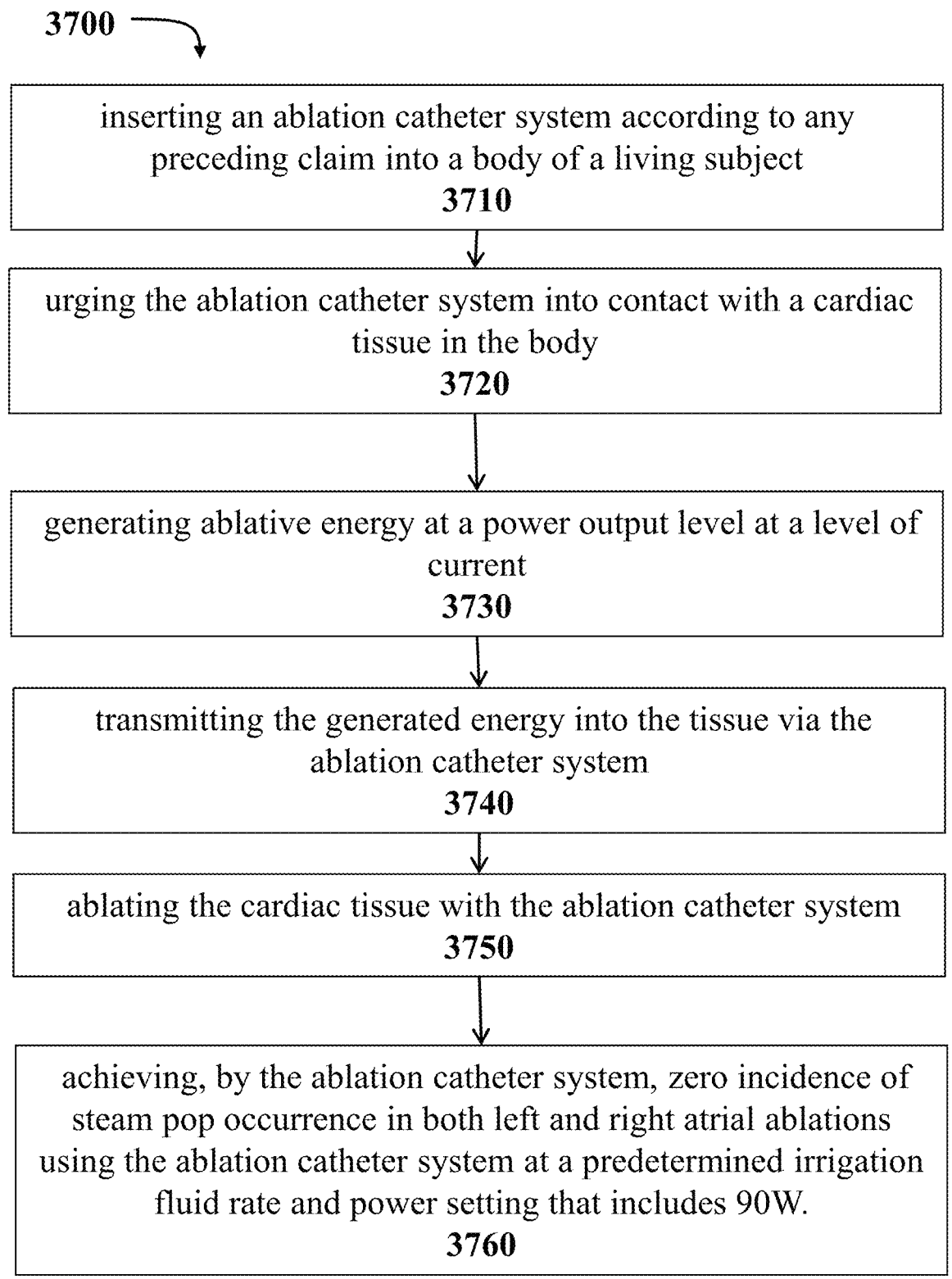
FIG. 37 depicts a graphical overview of one method or use according to this disclosure.

FIG. 37 depicts a graphical overview of one method 3700 according to this disclosure. The method 3700 can include 3710 inserting an ablation catheter system according to any preceding claim into a body of a living subject; 3720 urging the ablation catheter system into contact with a cardiac tissue in the body; 3730 generating ablative energy at a power output level at a level of current; 3740 transmitting the generated energy into the tissue via the ablation catheter system; 3750 ablating the cardiac tissue with the ablation catheter system; and 3760 achieving, by the ablation catheter system, zero incidence of steam pop occurrence in both left and right atrial ablations using the ablation catheter system at a predetermined irrigation fluid rate and power setting that includes 90 W.

Figure 38:
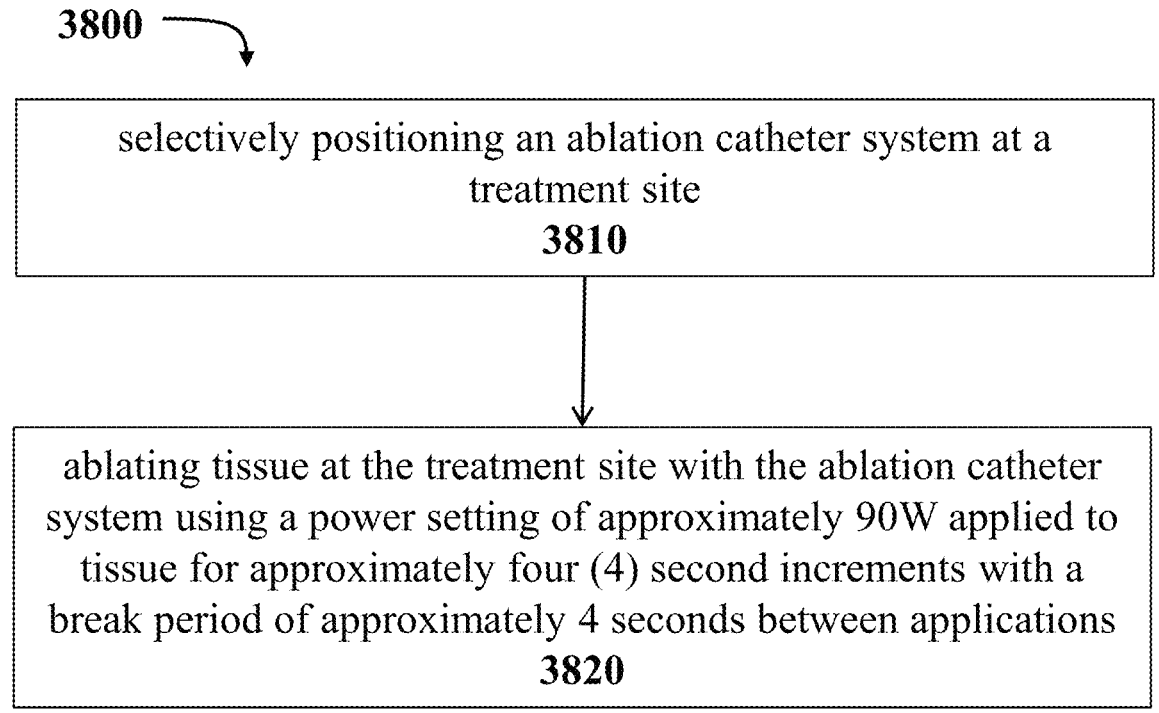
FIG. 38 depicts a graphical overview of one method or use according to this disclosure.

FIG. 38 depicts a graphical overview of one method 3800 according to this disclosure. The method 3800 can include method 3810 selectively positioning an ablation catheter system at a treatment site; 3820 ablating tissue at the treatment site with the ablation catheter system using a power setting of approximately 90 W applied to tissue for approximately four (4) second increments with a break period of approximately 4 seconds between applications.

FIG. 39 depicts a graphical overview of one method 3900 according to this disclosure. The method 3900 can include 3910 delivering an ablation catheter system to a treatment site comprising cardiac tissue, the system comprising at least one electrode and at least one sensor in proximity with the other; 3920 ablating cardiac tissue with the ablation catheter system at a predetermined irrigation fluid rate and power setting comprising approximately 90 W; and 3930 achieving approximately zero incidence of steam pop occurrence in both left and right atrial ablations and complete pulmonary vein isolation, by the ablation catheter system, for all patients of a predetermined patient population suffering from PAF.

The methods, systems, and devices of this disclosure demonstrated clinically effective and/or safe mapping catheter systems with for use with patients having certain conditions, such as PAF. The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

The invention claimed is:

1. A method or use, comprising:
   selectively positioning an ablation catheter system at a treatment site comprising cardiac tissue;
   ablating cardiac tissue at the treatment site with the ablation catheter system using a power setting of approximately 90W applied to tissue for a first ablation time of approximately four (4) seconds to achieve a first maximum tissue temperature;
   ceasing ablation for a break period of approximately 4 seconds immediately following the first ablation time;
   ablating, immediately after the break period of approximately 4 seconds and using the power setting of approximately 90W applied to the cardiac tissue for a second ablation time of approximately 4 seconds, the cardiac tissue at the treatment site with the ablation catheter system to achieve a second maximum tissue temperature; and
   achieving approximately zero incidence of steam pop occurrence in both left and right atrial ablations and complete pulmonary vein isolation, by the ablation catheter system, for all patients of a predetermined patient population suffering from PAF.

2. The method or use of claim 1, wherein the second maximum tissue temperature is approximately 76° C.

3. The method or use of claim 1, the step of ablating cardiac tissue further comprising increasing of temperature between first and second maximum tissue temperature by at least about 13% between first and second ablation applications.

4. The method or use of claim 1, the step of ablating tissue comprises a point-by-point "kissing" ablation approach causing a continuous and transmural linear lesion line at an atrial wall with minimal over-lapped lesions.

5. The method or use of claim 1, the step of ablating tissue comprising achieving a lesion depth approximately 40% deeper between first and second ablation applications, the method or use further comprising applying to the treatment site, by a distal end of the ablation catheter system, a contact force ranging between approximately 5-30 grams.

6. The method or use of claim 1, further comprising:
   delivering, by and through an elongated body of the ablation catheter system, a continuous infusion of approximately 8 milliliters/minute of treatment solution when not delivering radiofrequency energy during radiofrequency ablation.

7. The method or use of claim 1, further comprising:
   moving the ablation catheter system approximately 4 millimeter if clinically effective ablation is achieved within 20 seconds as determined by electrogram reduction and/or impedance drop.

8. A method or use for an ablation procedure, comprising:
   delivering an ablation catheter system to a treatment site comprising cardiac tissue, the system comprising at least one electrode and at least one sensor in proximity with the other;
   ablating cardiac tissue with the ablation catheter system at a predetermined irrigation fluid rate and power setting comprising approximately 90W;
   ceasing ablation for a break period of approximately 4 seconds immediately following the first ablation time;
   ablating, immediately after the break period of approximately 4 seconds for a second ablation time of approximately 4 seconds; and
   achieving approximately zero incidence of steam pop occurrence in both left and right atrial ablations and complete pulmonary vein isolation, by the ablation catheter system, for all patients of a predetermined patient population suffering from PAF.

9. The method or use of claim 8, the ablation catheter system comprising:
   an elongated body;
   an electrode assembly comprising a shell configured with an inner chamber and a wall; and
   a micro-element extending through the inner chamber between a proximal portion and a distal portion of the shell, the micro-element having a distal end received in at least one aperture in the wall, the distal end being at least coextensive with an outer surface of the wall.

10. The method or use of claim 8, the step of achieving complete pulmonary vein isolation further comprises applying an average force of approximately 7.5 grams by the ablation catheter system to the cardiac tissue during use and achieving a target temperature of approximately 50° C. and ablation duration of approximately 4 seconds.

11. The method or use of claim 8, the step of achieving complete pulmonary vein isolation further comprises applying an average force of approximately 9 grams by the ablation catheter system to the cardiac tissue during use and achieving a target temperature of approximately 55° C. and ablation duration of approximately 4 seconds.

12. The method or use of claim 8, the step of achieving complete pulmonary vein isolation further comprises applying an average force of approximately 17.7 grams by the ablation catheter system to the cardiac tissue during use and achieving a target temperature of approximately 60° C. and ablation duration of approximately 4 seconds.

13. The method or use of claim 8, the step of achieving complete pulmonary vein isolation further comprises applying an average force of approximately 13.6 grams by the ablation catheter system to the cardiac tissue during use and achieving a target temperature of approximately 60° C. and ablation duration of approximately 2 seconds.

14. The method or use of claim 8, further comprising: delivering, by the ablation catheter system, the predetermined irrigation flow rate of approximately 380 mL or less of treatment fluids to the treatment site during the ablation procedure.

15. The method or use of claim 8, the step of achieving complete pulmonary vein isolation further comprising a total ablation procedure time less than or equal to approximately 46 minutes.

16. The method or use of claim 8, the step of achieving complete pulmonary vein isolation further comprising a total fluoroscopy time of less than or equal to approximately 6.5 minutes or less.

17. The method or use of claim 8, the step of achieving complete pulmonary vein isolation further comprising a total radiofrequency application duration time of approximately 8 minutes or less.

18. The method or use of claim 8, the step of achieving complete pulmonary vein isolation further comprising a total radiofrequency application duration time of 30 seconds on a posterior wall of the treatment site.

19. The method or use of claim 8, the step of ablating the cardiac tissue comprises a point-by-point "kissing" ablation approach causing a continuous and transmural linear lesion line at an atrial wall with minimal over-lapped lesions.

* * * * *